(12) United States Patent
Wei

(10) Patent No.: US 12,137,682 B2
(45) Date of Patent: *Nov. 12, 2024

(54) COMPOSITIONS AND METHODS FOR REDUCING ICE CRYSTAL FORMATION

(71) Applicant: X-THERMA, INC., Richmond, CA (US)

(72) Inventor: Xiaoxi Wei, El Cerrito, CA (US)

(73) Assignee: X-Therma, Inc., Hercules, CA (US)

(*) Notice: Subject to any disclaimer, the term of this patent is extended or adjusted under 35 U.S.C. 154(b) by 178 days.

This patent is subject to a terminal disclaimer.

(21) Appl. No.: 17/974,202

(22) Filed: Oct. 26, 2022

(65) Prior Publication Data

US 2023/0276788 A1 Sep. 7, 2023

Related U.S. Application Data

(63) Continuation of application No. 16/881,794, filed on May 22, 2020, now Pat. No. 11,510,407, which is a continuation of application No. 15/969,256, filed on May 2, 2018, now Pat. No. 10,694,739, which is a continuation of application No. 15/486,522, filed on Apr. 13, 2017, now Pat. No. 9,986,733, which is a continuation of application No. PCT/US2016/056852, filed on Oct. 13, 2016.

(60) Provisional application No. 62/241,588, filed on Oct. 14, 2015.

(51) Int. Cl.
| | |
|---|---|
| *A01N 1/02* | (2006.01) |
| *A23B 4/20* | (2006.01) |
| *A23G 9/32* | (2006.01) |
| *A23G 9/38* | (2006.01) |
| *A23L 3/3526* | (2006.01) |
| *A23L 3/37* | (2006.01) |
| *A23L 13/40* | (2023.01) |
| *A23L 17/00* | (2016.01) |
| *A61K 8/64* | (2006.01) |
| *A61K 8/88* | (2006.01) |
| *A61Q 90/00* | (2009.01) |
| *C07K 7/06* | (2006.01) |
| *C07K 7/08* | (2006.01) |
| *C07K 14/00* | (2006.01) |
| *C08G 69/10* | (2006.01) |
| *C09K 3/18* | (2006.01) |

(52) U.S. Cl.
CPC ............ *A01N 1/0221* (2013.01); *A23B 4/20* (2013.01); *A23G 9/32* (2013.01); *A23G 9/38* (2013.01); *A23L 3/3526* (2013.01); *A23L 3/37* (2013.01); *A23L 13/42* (2016.08); *A23L 17/00* (2016.08); *A61K 8/64* (2013.01); *A61K 8/88* (2013.01); *A61Q 90/00* (2013.01); *C07K 7/06* (2013.01); *C07K 7/08* (2013.01); *C07K 14/001* (2013.01); *C08G 69/10* (2013.01); *C09K 3/18* (2013.01); *A23V 2002/00* (2013.01); *A61K 2800/54* (2013.01)

(58) Field of Classification Search
CPC .......... A01N 1/0221; A23B 4/20; A23G 9/32; A23G 9/38; A23L 3/3526; A23L 3/37; A23L 13/42; A23L 17/00; A61K 8/64; A61K 8/88; A61K 2800/54; A61Q 90/00; C07K 7/06; C07K 7/08; C07K 14/001; C08G 69/10; C09K 3/18; A23V 2002/00; C08K 5/20; C08L 77/04

See application file for complete search history.

(56) References Cited

U.S. PATENT DOCUMENTS

| | | | |
|---|---|---|---|
| 4,672,037 | A | 6/1987 | Daggett et al. |
| 5,071,741 | A | 12/1991 | Brockbank |
| 5,276,006 | A | 1/1994 | Shin et al. |
| 5,605,932 | A | 2/1997 | Ng et al. |
| 5,608,110 | A | 3/1997 | Ramalingam et al. |
| 5,627,286 | A | 5/1997 | Ramalingam et al. |
| 5,641,625 | A | 6/1997 | Ecker et al. |
| 5,656,254 | A | 8/1997 | Ramalingam et al. |
| 5,665,329 | A | 9/1997 | Ramalingam et al. |

(Continued)

FOREIGN PATENT DOCUMENTS

| | | |
|---|---|---|
| AU | 2016338410 B2 | 7/2021 |
| CN | 1426461 A | 6/2003 |

(Continued)

OTHER PUBLICATIONS

Fowler et al. Structure-Function relationships in peptoids: Recent advances toward deciphering the structural requirements for biological fucntion. Organic and Biomolecular Chemistry, 2009, vol. 7 pp. 1508-1524. (Year: 2009).*

(Continued)

*Primary Examiner* — Marcela M Cordero Garcia
(74) *Attorney, Agent, or Firm* — Kilpatrick Townsend & Stockton LLP

(57) ABSTRACT

The present invention provides peptoid polymers capable of reducing or inhibiting the formation of ice crystals at sub 0° C. temperatures. Also provided are peptoid-peptide hybrids comprising the peptoid polymers provided herein. The peptoid polymers and peptoid-peptide hybrids provided herein are useful for making cryoprotectant solutions. The peptoid polymers, peptoid-peptide hybrids, and cryoprotectant solutions provided herein are useful for making antifreeze solutions, frozen food products, and cosmetic care products. Also provided herein are methods for preserving a tissue, an organ, a cell, or a biological macromolecule using the compositions described herein.

13 Claims, 11 Drawing Sheets

(56) References Cited

U.S. PATENT DOCUMENTS

| | | |
|---|---|---|
| 5,686,625 A | 11/1997 | Kos |
| 5,696,231 A | 12/1997 | Abelman et al. |
| 5,700,779 A | 12/1997 | Goodfellow et al. |
| 5,714,331 A | 2/1998 | Buchardt et al. |
| 5,719,262 A | 2/1998 | Buchardt et al. |
| 5,721,213 A | 2/1998 | Sato et al. |
| 5,736,336 A | 4/1998 | Buchardt et al. |
| 5,741,912 A | 4/1998 | Ramalingam et al. |
| 5,766,855 A | 6/1998 | Buchardt et al. |
| 5,773,571 A | 6/1998 | Nielsen et al. |
| 5,786,461 A | 7/1998 | Buchardt et al. |
| 5,811,387 A | 9/1998 | Simon et al. |
| 5,831,005 A | 11/1998 | Zuckerman et al. |
| 5,840,485 A | 11/1998 | Lebl et al. |
| 5,877,278 A | 3/1999 | Zuckermann et al. |
| 5,932,707 A | 8/1999 | Archer et al. |
| 5,965,695 A | 10/1999 | Simon et al. |
| 5,977,296 A | 11/1999 | Nielsen et al. |
| 5,977,301 A | 11/1999 | Zuckerman et al. |
| 5,986,053 A | 11/1999 | Ecker et al. |
| 6,001,815 A | 12/1999 | Yanai et al. |
| 6,004,531 A | 12/1999 | Archer et al. |
| 6,025,472 A | 2/2000 | Abelman et al. |
| 6,033,631 A | 3/2000 | Zuckermann et al. |
| 6,075,121 A | 6/2000 | Simon et al. |
| 6,090,912 A | 7/2000 | Lebl et al. |
| 6,096,710 A | 8/2000 | Goodman et al. |
| 6,107,470 A | 8/2000 | Nielsen et al. |
| 6,153,590 A | 11/2000 | Andersen et al. |
| 6,169,073 B1 | 1/2001 | Halazonetis et al. |
| 6,201,103 B1 | 3/2001 | Nielsen et al. |
| 6,207,072 B1 | 3/2001 | Sayed et al. |
| 6,228,982 B1 | 5/2001 | Norden et al. |
| 6,232,494 B1 | 5/2001 | Morgenstern et al. |
| 6,239,108 B1 | 5/2001 | Lin et al. |
| 6,245,886 B1 | 6/2001 | Halazonetis et al. |
| 6,248,713 B1 | 6/2001 | Lin et al. |
| 6,251,433 B1 | 6/2001 | Zuckermann et al. |
| 6,255,285 B1 | 7/2001 | Kotake et al. |
| 6,270,533 B1 | 8/2001 | Genet et al. |
| 6,306,204 B1 | 10/2001 | Lin |
| 6,316,406 B1 | 11/2001 | Yanai et al. |
| 6,329,506 B1 | 12/2001 | Goodman et al. |
| 6,350,853 B1 | 2/2002 | Nielsen et al. |
| 6,357,163 B1 | 3/2002 | Buchardt et al. |
| 6,376,708 B1 | 4/2002 | Morgenstern et al. |
| 6,395,474 B1 | 5/2002 | Buchardt et al. |
| 6,414,112 B1 | 7/2002 | Buchardt et al. |
| 6,441,130 B1 | 8/2002 | Egholm et al. |
| 6,451,968 B1 | 9/2002 | Egholm et al. |
| 6,458,766 B1 | 10/2002 | Fenical et al. |
| 6,465,655 B1 | 10/2002 | Fitzpatrick et al. |
| 6,468,977 B1 | 10/2002 | Karimian et al. |
| 6,468,986 B1 | 10/2002 | Zuckermann et al. |
| 6,476,256 B1 | 11/2002 | Heise et al. |
| 6,596,687 B1 | 7/2003 | Lin et al. |
| 6,608,026 B1 | 8/2003 | Wang et al. |
| 6,610,650 B1 | 8/2003 | Norden et al. |
| 6,613,873 B1 | 9/2003 | Buchardt et al. |
| 6,632,950 B2 | 10/2003 | Phillion et al. |
| 6,677,359 B2 | 1/2004 | Lauffer et al. |
| 6,677,445 B1 | 1/2004 | Innis et al. |
| 6,686,442 B2 | 2/2004 | Neilsen et al. |
| 6,703,359 B1 | 3/2004 | Young et al. |
| 6,710,163 B1 | 3/2004 | Buchardt et al. |
| 6,710,164 B1 | 3/2004 | Nielsen et al. |
| 6,713,602 B1 | 3/2004 | Buchardt et al. |
| 6,770,738 B1 | 8/2004 | Ecker et al. |
| 6,783,929 B1 | 8/2004 | Zuckermann et al. |
| 6,811,977 B2 | 11/2004 | Wold et al. |
| 6,812,237 B2 | 11/2004 | Cowen et al. |
| 6,846,921 B2 | 1/2005 | Innis et al. |
| 6,858,576 B1 | 2/2005 | Young et al. |
| 6,870,028 B1 | 3/2005 | Andersen et al. |
| 6,887,845 B2 | 5/2005 | Barron et al. |
| 6,989,366 B2 | 1/2006 | Beeley et al. |
| 6,992,064 B2 | 1/2006 | Orts et al. |
| 7,026,166 B2 | 4/2006 | Suich et al. |
| 7,030,216 B2 | 4/2006 | Horn et al. |
| 7,041,784 B2 | 5/2006 | Wang et al. |
| 7,094,758 B2 | 8/2006 | Wang et al. |
| 7,115,569 B2 | 10/2006 | Beeley et al. |
| 7,126,024 B2 | 10/2006 | Morgenstern et al. |
| 7,138,375 B2 | 11/2006 | Beeley et al. |
| 7,148,058 B2 | 12/2006 | Charych et al. |
| 7,153,682 B2 | 12/2006 | Charych et al. |
| 7,220,721 B1 | 5/2007 | Beeley et al. |
| 7,223,833 B1 | 5/2007 | Nielsen et al. |
| 7,329,778 B2 | 2/2008 | Morgenstern et al. |
| 7,378,485 B2 | 5/2008 | Buchardt et al. |
| 7,408,023 B2 | 8/2008 | Horn et al. |
| 7,410,951 B2 | 8/2008 | Andersen et al. |
| 7,419,952 B2 | 9/2008 | Beeley et al. |
| 7,422,861 B2 | 9/2008 | Zuckermann et al. |
| 7,452,858 B2 | 11/2008 | Hiles et al. |
| 7,462,592 B2 | 12/2008 | Zuckermann et al. |
| 7,504,436 B2 | 3/2009 | Thormann et al. |
| 7,569,659 B1 | 8/2009 | Christensen et al. |
| 7,608,621 B2 | 10/2009 | Shaw et al. |
| 7,696,161 B2 | 4/2010 | Beeley et al. |
| 7,696,240 B2 | 4/2010 | Banner et al. |
| 7,700,549 B2 | 4/2010 | Beeley et al. |
| 7,704,756 B2 | 4/2010 | Suich et al. |
| 7,736,909 B2 | 6/2010 | Kodadek |
| 7,737,145 B2 | 6/2010 | Arnaiz et al. |
| 7,740,861 B2 | 6/2010 | Ostroff |
| 7,772,397 B2 | 8/2010 | Andersen et al. |
| 7,825,215 B1 | 11/2010 | Christensen et al. |
| 7,834,144 B2 | 11/2010 | Peretz et al. |
| 7,838,726 B2 | 11/2010 | Serbedzija et al. |
| 7,897,612 B2 | 3/2011 | Fitch et al. |
| 8,026,210 B2 | 9/2011 | Young et al. |
| 8,114,830 B2 | 2/2012 | Barron et al. |
| 8,163,567 B2 | 4/2012 | Kodadek |
| 8,263,550 B2 | 9/2012 | Beeley et al. |
| 8,280,405 B2 | 10/2012 | Sanz-Pastor et al. |
| 8,324,208 B2 | 12/2012 | Duffy et al. |
| 8,334,239 B2 | 12/2012 | Kodadek et al. |
| 8,445,632 B2 | 5/2013 | Barron et al. |
| 8,455,504 B2 | 6/2013 | Gram et al. |
| 8,461,300 B2 | 6/2013 | Robinson et al. |
| 8,486,370 B2 | 7/2013 | Carpenter et al. |
| 8,501,958 B2 | 8/2013 | Kim et al. |
| 8,524,663 B2 | 9/2013 | Kirshenbaum et al. |
| 8,557,834 B2 | 10/2013 | Fitch et al. |
| 8,569,303 B2 | 10/2013 | Arnaiz et al. |
| RE44,613 E | 11/2013 | Duffy et al. |
| 8,580,275 B2 | 11/2013 | Ostroff |
| 8,603,756 B2 | 12/2013 | Frost et al. |
| 8,673,842 B2 | 3/2014 | Barron et al. |
| 8,716,242 B2 | 5/2014 | Barthelemy et al. |
| 8,772,255 B2 | 7/2014 | Burkoth et al. |
| 8,815,884 B2 | 8/2014 | Fitch et al. |
| 8,828,413 B2 | 9/2014 | Kirshenbaum et al. |
| 8,895,695 B2 | 11/2014 | Zumbrunn et al. |
| 8,940,331 B2 | 1/2015 | Barron et al. |
| 8,946,149 B2 | 2/2015 | Anderson et al. |
| 8,951,962 B2 | 2/2015 | Prickett et al. |
| 8,952,127 B2 | 2/2015 | Chen et al. |
| 9,006,392 B2 | 4/2015 | Dawson et al. |
| 9,073,977 B2 | 7/2015 | Zuckermann et al. |
| 9,107,959 B2 | 8/2015 | Kirshenbaum et al. |
| 9,155,702 B2 | 10/2015 | Lee et al. |
| 9,233,162 B2 | 1/2016 | Kodadek et al. |
| 9,248,109 B2 | 2/2016 | Yu et al. |
| 9,315,509 B2 | 4/2016 | Arnaiz et al. |
| 9,315,548 B2 | 4/2016 | Kirshenbaum et al. |
| 9,346,821 B2 | 5/2016 | Suzuki et al. |
| 9,364,449 B2 | 6/2016 | Sadowski et al. |
| 9,376,381 B2 | 6/2016 | Yu |
| 9,458,199 B2 | 10/2016 | Frost et al. |
| 9,458,449 B2 | 10/2016 | Kirshenbaum et al. |
| 9,986,733 B2 | 6/2018 | Wei |
| 10,694,739 B2 | 6/2020 | Wei |

(56) References Cited

U.S. PATENT DOCUMENTS

| | | | |
|---|---|---|---|
| 11,510,407 B2 | 11/2022 | Wei | |
| 11,564,388 B2 * | 1/2023 | Wei | C07K 7/08 |
| 11,608,414 B2 * | 3/2023 | Wei | A61K 8/64 |
| 2001/0018536 A1 | 8/2001 | Morgenstern et al. | |
| 2001/0039020 A1 | 11/2001 | Zuckermann et al. | |
| 2002/0055125 A1 | 5/2002 | Charych et al. | |
| 2002/0077284 A1 | 6/2002 | Eckert et al. | |
| 2002/0115612 A1 | 8/2002 | Zuckermann et al. | |
| 2002/0146718 A1 | 10/2002 | Buchardt et al. | |
| 2002/0160383 A1 | 10/2002 | Buchardt et al. | |
| 2003/0013659 A1 | 1/2003 | Fenical et al. | |
| 2003/0105286 A1 | 6/2003 | Egholm et al. | |
| 2003/0124557 A1 | 7/2003 | Halazonetis et al. | |
| 2003/0162719 A1 | 8/2003 | Rothbard et al. | |
| 2003/0170826 A1 | 9/2003 | Rabinovich et al. | |
| 2003/0171537 A1 | 9/2003 | Halazonetis et al. | |
| 2003/0232355 A1 | 12/2003 | Norden et al. | |
| 2003/0235851 A1 | 12/2003 | Roberts et al. | |
| 2004/0005637 A1 | 1/2004 | Westman et al. | |
| 2004/0014984 A1 | 1/2004 | Phillion et al. | |
| 2004/0033958 A1 | 2/2004 | Ferrer Montiel et al. | |
| 2004/0038309 A1 | 2/2004 | Zuckermann et al. | |
| 2004/0059087 A1 | 3/2004 | Buchardt et al. | |
| 2004/0072821 A1 | 4/2004 | Lauffer et al. | |
| 2004/0143134 A1 | 7/2004 | Morgenstern | |
| 2004/0161798 A1 | 8/2004 | Kodadek | |
| 2004/0192564 A1 | 9/2004 | Balasubramaniam et al. | |
| 2004/0198775 A1 | 10/2004 | Fraser et al. | |
| 2004/0258750 A1 | 12/2004 | Alaux et al. | |
| 2004/0266692 A1 | 12/2004 | Young et al. | |
| 2005/0003558 A1 | 1/2005 | Zuckermann et al. | |
| 2005/0009041 A1 | 1/2005 | Buchardt et al. | |
| 2005/0048550 A1 | 3/2005 | Storkus et al. | |
| 2005/0048552 A1 | 3/2005 | Ecker et al. | |
| 2005/0054871 A1 | 3/2005 | Coleman et al. | |
| 2005/0118645 A1 | 6/2005 | Michelitsch et al. | |
| 2006/0019899 A1 | 1/2006 | Storkus et al. | |
| 2006/0019900 A1 | 1/2006 | Lam et al. | |
| 2006/0019912 A1 | 1/2006 | Burkoth et al. | |
| 2006/0035242 A1 | 2/2006 | Michelitsch et al. | |
| 2006/0041095 A1 | 2/2006 | Westman et al. | |
| 2006/0046255 A1 | 3/2006 | Buchardt et al. | |
| 2006/0111274 A1 | 5/2006 | Rothbard et al. | |
| 2006/0142319 A1 | 6/2006 | Chen et al. | |
| 2006/0147658 A1 | 7/2006 | Olijve et al. | |
| 2006/0159744 A1 | 7/2006 | Alaux et al. | |
| 2006/0160731 A1 | 7/2006 | Buchardt et al. | |
| 2006/0194713 A1 | 8/2006 | Belanoff | |
| 2006/0222787 A1 | 10/2006 | Olijve et al. | |
| 2006/0229255 A1 | 10/2006 | Tarrason et al. | |
| 2007/0010656 A1 | 1/2007 | Beeley et al. | |
| 2007/0042041 A1 | 2/2007 | Kim | |
| 2007/0042442 A1 | 2/2007 | Charych et al. | |
| 2007/0048806 A1 | 3/2007 | Charych et al. | |
| 2007/0054298 A1 | 3/2007 | Kirshenbaum et al. | |
| 2007/0149456 A1 | 6/2007 | Bruns et al. | |
| 2007/0155727 A1 | 7/2007 | Chen et al. | |
| 2007/0190517 A1 | 8/2007 | Fahy et al. | |
| 2007/0213335 A1 | 9/2007 | Fitch et al. | |
| 2008/0089938 A9 | 4/2008 | Zuckermann et al. | |
| 2008/0125353 A1 | 5/2008 | Hiles et al. | |
| 2008/0171756 A1 | 7/2008 | Shaw et al. | |
| 2008/0175910 A1 | 7/2008 | Andre et al. | |
| 2008/0234299 A1 | 9/2008 | Buchstaller et al. | |
| 2009/0011946 A1 | 1/2009 | Majumdar et al. | |
| 2009/0061462 A1 | 3/2009 | Michelitsch et al. | |
| 2009/0130774 A1 | 5/2009 | Peretz et al. | |
| 2009/0176825 A1 | 7/2009 | Fitch et al. | |
| 2009/0226528 A1 | 9/2009 | Czech et al. | |
| 2009/0239273 A1 | 9/2009 | Semba et al. | |
| 2009/0286435 A1 | 11/2009 | Badyal et al. | |
| 2009/0318667 A1 | 12/2009 | Kirshenbaum et al. | |
| 2010/0028719 A1 | 2/2010 | Messersmith et al. | |
| 2010/0069308 A1 | 3/2010 | Chorny et al. | |
| 2010/0105629 A1 | 4/2010 | Bachovchin et al. | |
| 2010/0105637 A1 | 4/2010 | Kim | |
| 2010/0172862 A1 | 7/2010 | Correia et al. | |
| 2010/0181250 A1 | 7/2010 | Kim et al. | |
| 2010/0216110 A1 | 8/2010 | Brockbank | |
| 2010/0222548 A1 | 9/2010 | Wessjohann et al. | |
| 2010/0303805 A1 | 12/2010 | Moola et al. | |
| 2010/0303835 A1 | 12/2010 | Gocke et al. | |
| 2010/0311036 A1 | 12/2010 | He | |
| 2011/0052735 A1 | 3/2011 | Zur Wiesche et al. | |
| 2011/0098324 A1 | 4/2011 | Brackley, III et al. | |
| 2011/0139170 A1 | 6/2011 | Hippe et al. | |
| 2011/0144167 A1 | 6/2011 | Tedesco | |
| 2011/0160227 A1 | 6/2011 | Shaw et al. | |
| 2011/0286973 A1 | 11/2011 | Serbedzija et al. | |
| 2011/0300053 A1 | 12/2011 | Chen et al. | |
| 2011/0304329 A1 | 12/2011 | Bulaj et al. | |
| 2012/0003387 A1 | 1/2012 | Kim et al. | |
| 2012/0004168 A1 | 1/2012 | Young et al. | |
| 2012/0021967 A1 | 1/2012 | Johnston et al. | |
| 2012/0027677 A1 | 2/2012 | Peretz et al. | |
| 2012/0065123 A1 | 3/2012 | Johnston et al. | |
| 2012/0115136 A1 | 5/2012 | Buchardt et al. | |
| 2012/0135942 A1 | 5/2012 | Obrecht et al. | |
| 2012/0196933 A1 | 8/2012 | Franklin et al. | |
| 2012/0220535 A1 | 8/2012 | Spaller et al. | |
| 2012/0269799 A1 | 10/2012 | Moola et al. | |
| 2012/0270741 A1 | 10/2012 | Moola et al. | |
| 2012/0295838 A1 | 11/2012 | Barron et al. | |
| 2013/0034532 A1 | 2/2013 | Cao et al. | |
| 2013/0065833 A1 | 3/2013 | Barron et al. | |
| 2013/0109627 A1 | 5/2013 | Barron et al. | |
| 2013/0123243 A1 | 5/2013 | Arnaiz et al. | |
| 2013/0165379 A1 | 6/2013 | Kolterman et al. | |
| 2013/0178835 A1 | 7/2013 | Gocke et al. | |
| 2013/0331322 A1 | 12/2013 | Young et al. | |
| 2013/0331424 A1 | 12/2013 | Weibel et al. | |
| 2014/0031523 A1 | 1/2014 | Barron et al. | |
| 2014/0100354 A1 | 4/2014 | Kirshenbaum et al. | |
| 2014/0256638 A1 | 9/2014 | Rabenstein et al. | |
| 2014/0274916 A1 | 9/2014 | Kirshenbaum et al. | |
| 2014/0315954 A1 | 10/2014 | Winters et al. | |
| 2014/0335047 A1 | 11/2014 | Ostroff | |
| 2014/0336383 A1 | 11/2014 | Fitch et al. | |
| 2014/0356268 A1 | 12/2014 | Schraven et al. | |
| 2014/0364583 A1 | 12/2014 | Obrecht et al. | |
| 2015/0031743 A1 | 1/2015 | Burkoth et al. | |
| 2015/0056142 A1 | 2/2015 | Tao et al. | |
| 2015/0057326 A1 | 2/2015 | Wu | |
| 2015/0080307 A1 | 3/2015 | Young et al. | |
| 2015/0080308 A1 | 3/2015 | Kolterman et al. | |
| 2015/0087577 A1 | 3/2015 | Zumbrunn et al. | |
| 2015/0126450 A1 | 5/2015 | Kirshenbaum et al. | |
| 2015/0174197 A1 | 6/2015 | Zuckermann et al. | |
| 2015/0257995 A1 | 9/2015 | Goutsis et al. | |
| 2015/0299254 A1 | 10/2015 | Kirshenbaum et al. | |
| 2015/0315157 A1 | 11/2015 | Fitch et al. | |
| 2016/0038606 A1 | 2/2016 | Winters et al. | |
| 2016/0045617 A1 | 2/2016 | Lee et al. | |
| 2016/0075734 A1 | 3/2016 | Menegatti | |
| 2016/0151284 A1 | 6/2016 | Heyes et al. | |
| 2016/0206679 A1 | 7/2016 | Baillie | |
| 2016/0215279 A1 | 7/2016 | Cao et al. | |
| 2016/0219880 A1 | 8/2016 | Kirshenbaum et al. | |
| 2016/0251387 A1 | 9/2016 | Jasper et al. | |
| 2016/0256567 A1 | 9/2016 | Heyes et al. | |
| 2016/0256568 A1 | 9/2016 | Heyes et al. | |
| 2016/0272649 A1 | 9/2016 | Arnaiz et al. | |
| 2016/0297772 A1 | 10/2016 | Fitch et al. | |
| 2016/0303186 A1 | 10/2016 | Spaller et al. | |
| 2017/0295777 A1 | 10/2017 | Wei | |
| 2019/0069537 A1 | 3/2019 | Wei | |
| 2021/0106506 A1 | 4/2021 | Schilling et al. | |
| 2021/0395302 A1 | 12/2021 | Yao et al. | |

FOREIGN PATENT DOCUMENTS

| | | |
|---|---|---|
| CN | 103724418 A | 4/2014 |
| CN | 104411714 A | 3/2015 |
| CN | 111789099 A | 10/2020 |

(56) References Cited

FOREIGN PATENT DOCUMENTS

| | | | |
|---|---|---|---|
| IN | 201817017550 A | | 8/2018 |
| WO | 2010014940 A2 | | 2/2010 |
| WO | 2010017412 A1 | | 2/2010 |
| WO | 2013043669 A1 | | 3/2013 |
| WO | 2013110374 A1 | | 8/2013 |
| WO | 2013158600 A1 | | 10/2013 |
| WO | 2013177241 A1 | | 11/2013 |
| WO | 2013185124 A1 | | 12/2013 |
| WO | 2014006041 A1 | | 1/2014 |
| WO | 2014057484 A1 | | 4/2014 |
| WO | 2014082948 A2 | | 6/2014 |
| WO | 2014144871 A1 | | 9/2014 |
| WO | 2014159937 A1 | | 10/2014 |
| WO | 2014169087 A2 | | 10/2014 |
| WO | 2014194073 A1 | | 12/2014 |
| WO | 2015011633 A1 | | 1/2015 |
| WO | 2015023715 A1 | | 2/2015 |
| WO | 2015044679 A1 | | 4/2015 |
| WO | 2015051921 A1 | | 4/2015 |
| WO | 2015096873 A1 | | 7/2015 |
| WO | 2015140807 A1 | | 9/2015 |
| WO | 2015153560 A1 | | 10/2015 |
| WO | 2016020437 A1 | | 2/2016 |
| WO | 2016059609 A1 | | 4/2016 |
| WO | 2017066454 A3 | | 6/2017 |

OTHER PUBLICATIONS

"Substituted Alkyl Definition," Available Online at: https://www.lawinsider.com/dictionary/substituted-alkyl, Mar. 28, 2022, 3 pages.

Bi et al., "Design and Synthesis of a Chemically Cleavable Fluorescent Nucleotide, 3'-O-Allyl-dGTP-allyl-Bodipy-FL-510, as a Reversible Terminator for DNA Sequencing by Synthesis," Journal of the American Chemical Society, vol. 128, No. 6, Mar. 1, 2006, pp. 2542-2543.

Application No. EP16856195.9, Extended European Search Report, Mailed On Oct. 2, 2019, 12 pages.

Hara et al., "Probing the Structural Requirements of Peptoids that Inhibit HDM2-p53 Interactions," Journal of the American Chemical Society Articles, vol. 128, No. 6, Jan. 19, 2006, pp. 1995-2004.

Huang et al., "Biomimetic Peptoid Oligomers as Dual-Action Antifreeze Agents," Proceedings of the National Academy of Sciences, vol. 109, No. 49, Dec. 4, 2012, pp. 19922-19927.

Lau et al., "Surface-Grafted Polysarcosine as a Peptoid Antifouling Polymer Brush," Langmuir, vol. 28, No. 46, Nov. 20, 2012, pp. 16099-16107.

Norgren et al., "On-Resin Click-Glycoconjugation of Peptoids," Synthesis, No. 3, Jan. 9, 2009, pp. 488-494.

Olsen, "Peptoid-Peptide Hybrid Backbone Architectures," Chembiochem, vol. 11, No. 2, Jan. 25, 2010, pp. 152-160.

Application No. PCT/US2016/056852, International Preliminary Report on Patentability, Mailed on Apr. 26, 2018, 9 pages.

Application No. PCT/US2016/056852, International Search Report and Written Opinion, Mailed on May 5, 2017, 14 pages.

Reyes et al., "First Investigation of the Kinetic Hydrate Inhibitor Performance of Poly(N-alkylglycine)s," Energy Fuels, American Chemical Society, vol. 28, Oct. 11, 2014, pp. 6889-6896.

Rosales et al., "Control of Crystallization and Melting Behavior in Sequence Specific Polypeptoids," Macromolecules, vol. 43, No. 13, Jun. 9, 2010, pp. 5627-5636.

Simon et al., "Peptoids: A Modular Approach to Drug Discovery," Proceedings of the National Academy of Sciences, vol. 89, No. 20, Oct. 15, 1992, pp. 9367-9371.

Simpson et al., "Selective Toxin Sequestrants for the Treatment of Bacterial Infections," Journal of the American Chemical Society, vol. 131, No. 16, Apr. 29, 2009, pp. 5760-5762.

Zimmermann et al., "Design of N-Substituted Peptomer Ligands for EVH1 Domains", The Journal of Biological Chemistry, vol. 278, No. 38, Sep. 19, 2003, pp. 36810-36818.

Jobin et al., "Preparation of N-Substituted N-Arylsulfonylglycines and Their Use in Peptoid Synthesis," Organic Letters, ACS Publications, 2015, DOI:10.1021/acs.orglett.5b02862, 4 pages, with Supporting Information (SI), 41 pages.

Vezina-Dawod et al., "N-Substituted Arylsulfonamide Building Blocks as Alternative Submonomers for Peptide Synthesis," Tetrahedron Letters 56 (2015) pp. 382-385, with Supporting Information (SI), 19 pages.

Ruijtenbeek et al., "Characterization of a Phosphorylated Peptide and Peptoid and Peptoid-Peptide Hybrids by Mass Spectrometry," J. Mass Spectrom. 2002; 37:47-55.

\* cited by examiner

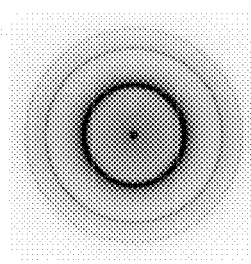
FIG. 3A Complete Vitrification
FIG. 3B Partial Vitrification with Presence of Cubic Ice
FIG. 3C Frozen: Cubic Ice Crystals
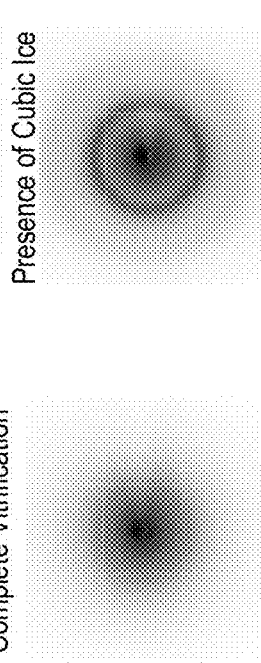
FIG. 3D
(d) X-ray diffraction of ice formation
| Solution | IceRing1 | IceRing2 |
|---|---|---|
| EG 15% | 7 | 8 |
| EG 17.5% | 7 | 8 |
| EG 20% | 7 | 8 |
| EG 22.5% | 7 | 5 |
| EG 25% (Standard) | 5 | 5 |
| EG 30% (Standard) | 3 | 2 |
| B (1 mg/ml) | 4 | 1 |
| B (5 mg/ml) EG 12.5% | 6 | 5 |
| D (1 mg/ml) | 4 | 5 |
| D (5 mg/ml) EG 17.5% | 0 | 0 |
| E (10 mg/ml) | 3 | 2 |
| E (5 mg/ml) EG 17.5% | 1 | 0 |
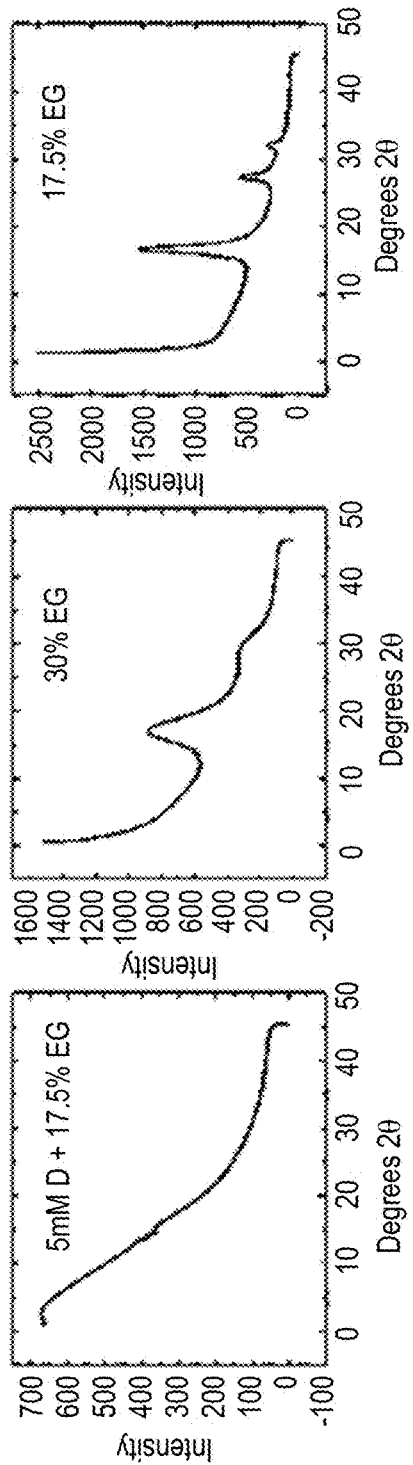

*Compound 10*
*5 mg/mL*

*Compound 12*
*5 mg/mL*

*Compound 8*
*5 mg/mL*

*Compound 13*
*5 mg/mL*

Compound 11
5 mg/mL

Compound 58
5 mg/mL

Control
15% EG

Compound 10
1 mg/mL

Compound 12
1 mg/mL

Compound 8
1 mg/mL

Compound 13
1 mg/mL

*Compound 11*
*1 mg/mL*

*Compound 58*
*1 mg/mL*

*Control*
*17.5% EG*

Control  Compound 12

Control  Compound 12

Control  Compound 12

COMPOSITIONS AND METHODS FOR REDUCING ICE CRYSTAL FORMATION

CROSS-REFERENCE TO RELATED APPLICATIONS

This application is a continuation of U.S. application Ser. No. 16/881,794 filed May 22, 2020, which is a continuation of U.S. application Ser. No. 15/969,256 filed May 2, 2018, now U.S. Pat. No. 10,694,739 issued Jun. 30, 2020, which is a continuation of U.S. application Ser. No. 15/486,522 filed Apr. 13, 2017, now U.S. Pat. No. 9,986,733 issued Jun. 5, 2018, which is a continuation of International Application No. PCT/US2016/056852 filed Oct. 13, 2016, which claims priority to U.S. Provisional Application No. 62/241,588 filed Oct. 14, 2015, the disclosures of which are hereby incorporated by reference in their entirety for all purposes.

STATEMENT AS TO RIGHTS TO INVENTIONS MADE UNDER FEDERALLY SPONSORED RESEARCH AND DEVELOPMENT

This invention was made with Government support under Contract No. W81XWH16C0066 awarded by the Department of Defense, Defense Health Agency. The Government has certain rights in the invention.

BACKGROUND OF THE INVENTION

Cryoprotective agents (CPAs) are compounds that when present in solution can reduce or inhibit ice crystal formation in solutions exposed to sub 0° C. temperatures. Current CPAs include small molecules (often referred to as penetrating CPAs), synthetic polymers, and antifreeze proteins.

Organ transplantation is currently the best treatment for end-stage organ failure in terms of survival, quality of life, and cost effectiveness. Unfortunately, a steep gap exists between supply and demand of organ transplants, and is one of the major medical obstacles that forces patients of debilitating disease to suffer low quality of life over a long period wait time. The apparent lack of organs is due to considerable waste from the absence of a reliable preservation method. In fact, over 50% of lungs, pancreas, and hearts remain unharvested from deceased donors.

In order to properly preserve organs, they have to be flushed with a preservation solution to remove blood and stabilize the organs. Even once stabilized in the preservation solution, there is only a limited time available for organ allocation, transportation, and transplantation after removal from the donor (~6-12 hours). This small timeframe results in most organs going to local patients because remote patient matches often cannot be confirmed in the limited time. As a result of this shortage and in spite of laws which exist in almost all countries prohibiting the sale of one's organs, illicit organ trade and human trafficking has risen to supply demand.

Current penetrating CPAs used in organ preservation include ethylene glycol, 1,2-propanediol, dimethyl sulfoxide, formamide, glycerol, sucrose, lactose, and D-mannitol, generally among others. In order to reduce or inhibit ice crystal growth at organ preservation temperatures, the effective concentration of the penetrating CPAs must be very high (≥60% is often required). At such high concentrations these compounds can be toxic to the tissues they are attempting to preserve, and the massive removal of CPAs upon warming before transplantation can lead to irreversible cell death.

Other CPAs used to reduce or inhibit ice crystal formation include synthetic polymers and antifreeze proteins. Similar to the penetrating CPAs, each of these have their drawbacks. Synthetic polymers, for example, are not capable of permeating the cellular membrane. As such, synthetic polymer CPAs can only control extracellular ice formation. In order to effectively preserve the biological sample, ice crystal formation must be controlled both inside and outside the cell. Naturally-occurring antifreeze proteins, such as those isolated from fish, plants, or insects, are highly effective at preventing ice formation, but current antifreeze proteins that are available are of low purity and are extremely expensive. Additionally, the use of antifreeze proteins to preserve a biological sample introduces a potential source of immunogenicity.

As such, there is a need in the art for novel non-toxic compounds to effectively reduce or inhibit ice crystal formation at sub 0° C. and cryogenic temperatures. The present disclosure satisfies this need and provides other advantages as well.

BRIEF SUMMARY OF THE INVENTION

In some aspects, provided herein is a peptoid polymer of formula (I):

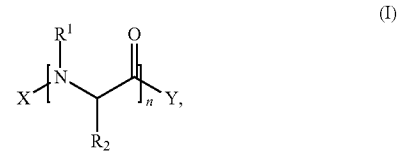

a tautomer thereof or stereoisomer thereof,
wherein:
each $R^1$ is independently selected from the group consisting of H, optionally substituted $C_{1-18}$ alkyl, optionally substituted $C_{2-18}$ alkenyl, optionally substituted $C_{2-18}$ alkynyl, optionally substituted $C_{1-18}$ hydroxyalkyl, optionally substituted alkoxy, optionally substituted $C_{1-18}$ alkylamino, optionally substituted $C_{1-18}$ alkylthio, optionally substituted carboxyalkyl, $C_{3-10}$ cycloalkyl, heterocycloalkyl, aryl, heteroaryl, ($C_{3-10}$ cycloalkyl)alkyl, (heterocycloalkyl)alkyl, arylalkyl, and heteroarylalkyl;
wherein at least one instance of $R^1$ is $C_{1-18}$ hydroxyalkyl, and
wherein any of the cycloalkyl, heterocycloalkyl, aryl, and heteroaryl groups is optionally and independently substituted with one or more $R^3$ groups;
each $R^2$ is independently selected from the group consisting of H, optionally substituted $C_{1-18}$ alkyl, optionally substituted $C_{2-18}$ alkenyl, optionally substituted $C_{2-18}$ alkynyl, optionally substituted $C_{1-18}$ hydroxyalkyl, optionally substituted $C_{1-18}$ alkylamino, optionally substituted $C_{1-18}$ alkylthio, and optionally substituted carboxyalkyl;
each $R^3$ is independently selected from the group consisting of halogen, oxo, thioxo, —OH, —SH, amino, $C_{1-8}$ alkyl, $C_{1-8}$ hydroxyalkyl, $C_{1-8}$ alkylamino, and $C_{1-8}$ alkylthio;
X and Y are independently selected from the group consisting of H, optionally substituted $C_{1-8}$ alkylamino, —OH, —SH, carboxy, optionally substituted $C_{1-8}$ hydroxyalkyl, optionally substituted $C_{1-8}$ alkylamino, optionally substituted $C_{2-8}$alkylthio, optionally substituted $C_{1-8}$ carboxyalkyl, and halogen; or alternatively X and Y are taken together to form a covalent bond; and the subscript n, representing the number of monomers in the polymer, is between 2 and 50;

provided that all instances of $R^1$ are not ethylhydroxy when n is between 3 and 7.

In some embodiments, each instance of $R^1$ in the peptoid polymer is selected from the group consisting of:

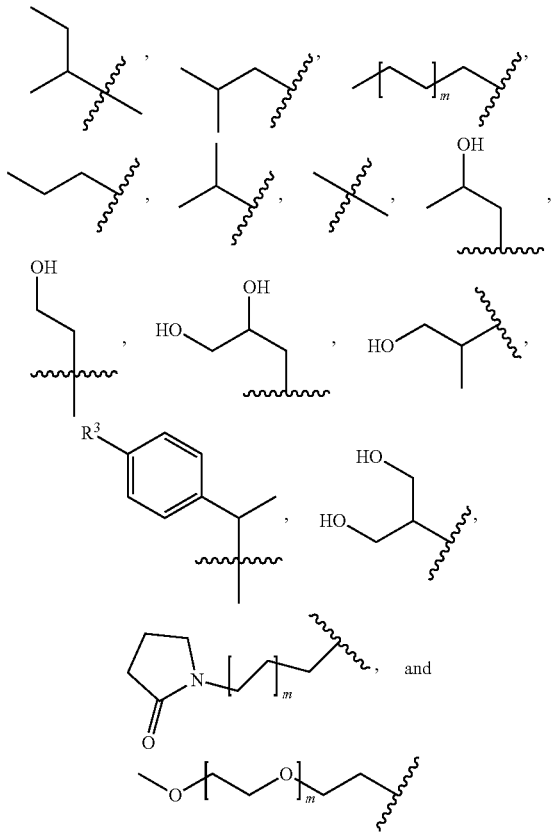

wherein:

m is between 1 and 8; and $R^3$ is selected from the group consisting of H, $C_{1-8}$ alkyl, hydroxyl, thiol, nitro, amine, oxo, and thioxo.

In some embodiments, each instance of $R^1$ in the peptoid polymer is selected from the group consisting of:

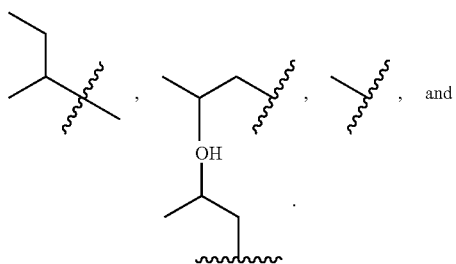

In some embodiments, each instance of $R^1$ in the peptoid polymer is a $C_{1-18}$ hydroxyalkyl group. In some embodiments, each instance of $R^1$ is a C1-6 hydroxyalkyl group. In some embodiments, each instance of $R^1$ is the same $C_{1-6}$ hydroxyalkyl group. In some embodiments, each instance of $R^1$ is:

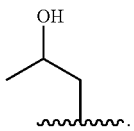 [SMILES: *CC(C)O]

In some embodiments, each instance of $R^2$ is H.

In some embodiments, the sequence length of the peptoid polymer, n, is between 3 and 25. In some embodiments, the sequence length of the peptoid polymer, n, is between 5 and 25. In some embodiments, the sequence length of the peptoid polymer, n, is between 8 and 50. In some embodiments, the sequence length of the peptoid polymer, n, is between 8 and 20.

In some embodiments, X and Y are H, optionally substituted $C_{1-8}$ alkylamino, —OH, —SH, carboxy, optionally substituted $C_{1-8}$ hydroxyalkyl, optionally substituted $C_{1-8}$ alkylamino, optionally substituted $C_{2-8}$alkylthio, optionally substituted $C_{1-8}$ carboxyalkyl, or halogen.

In some embodiments, X and Y of the peptoid polymer are taken together to form a covalent bond.

In some embodiments, the sequence length of the peptoid polymer, n, is 10, and the peptoid polymer comprises: 3 Nhp monomers and 7 Nsb monomers, 4 Nhp monomers and 6 Nsb monomers, 5 Nhp monomers and 5 Nsb monomers, 6 Nhp monomers and 4 Nsb monomers, 7 Nhp monomers and 3 Nsb monomers, 8 Nhp monomers and 2 Nsb monomers, or 10 Nhp monomers.

In some embodiments, the peptoid polymer has the sequence Nhp-Nhp-Nhp-Nhp-Nhp-Nhp-Nhp-Nhp-Nhp-Nhp (SEQ ID NO:2), and X is H or $C_{1-8}$ acyl and Y is —OH or —NH$_2$ or $C_{1-8}$ alkyl. In some embodiments, the peptoid polymer has the sequence Nsb-Nsb-Nhp-Nsb-Nsb-Nhp-Nsb-Nsb-Nhp-Nsb (SEQ ID NO: 1), and X is H or $C_{1-8}$ acyl and Y is —OH or —NH$_2$ or $C_{1-8}$ alkyl. In some embodiments, the peptoid polymer has the sequence Nsb-Nhp-Nhp-Nhp-Nsb-Nhp-Nhp-Nhp-Nsb-Nhp (SEQ ID NO:7), and X is H or $C_{1-8}$ acyl and Y is —OH or —NH$_2$ or $C_{1-8}$ alkyl. In some embodiments, the peptoid polymer has the sequence Nsb-Nsb-Nhp-Nhp-Nsb-Nsb-Nhp-Nhp-Nsb-Nsb (SEQ ID NO:8), and X is H or $C_{1-8}$ acyl and Y is —OH or —NH$_2$ or $C_{1-8}$ alkyl. In some embodiments, the peptoid polymer has the sequence Nsb-Nhp-Nhp-Nhp-Nhp-Nhp-Nsb-Nhp-Nhp-Nhp (SEQ ID NO:9), and X is H or $C_{1-8}$ acyl and Y is —OH or —NH$_2$ or $C_{1-8}$ alkyl.

In some embodiments, the sequence length of the peptoid polymer, n, is 10, and the peptoid polymer comprises: 3 Nhp monomers and 7 Nine monomers, 4 Nhp monomers and 6 Nine monomers, 5 Nhp monomers and 5 Nine monomers, 6 Nhp monomers and 4 Nine monomers, 7 Nhp monomers and 3 Nine monomers, or 8 Nhp monomers and 2 Nine monomers.

In some embodiments, the sequence length of the peptoid polymer, n, is 10, and the peptoid polymer comprises: 5 Nhe monomers and 5 Nsb monomers, or 5 Nhp monomers and 5 Nbu monomers.

In some embodiments, the sequence length of the peptoid polymer, n, is 10, and the peptoid polymer comprises: 4 Nhp monomers and 6 Nib monomers, 4 Nhp monomers and 6 Nbu monomers, 4 Nhp monomers and 6 Npr monomers, or 4 Nhp monomers and 6 Nip monomers.

In some embodiments, the sequence length of the peptoid polymer, n, is 14, and the peptoid polymer comprises: 6 Nhp monomers and 8 Nsb monomers, 7 Nhp monomers and 7 Nsb monomers, 8 Nhp monomers and 6 Nsb monomers, 10 Nhp monomers and 4 Nsb monomers, or 14 Nhp monomers.

In some embodiments, the sequence length of the peptoid polymer, n, is 14, and the peptoid polymer comprises: 6 Nhp monomers and 8 Nib monomers, 7 Nhp monomers and 7 Nib monomers, 8 Nhp monomers and 6 Nib monomers, 10 Nhp monomers and 4 Nib monomers, or 14 Nhp monomers.

In some embodiments, the sequence length of the peptoid polymer, n, is 16, and the peptoid polymer comprises: 5 Nhp monomers and 11 Nsb monomers, 7 Nhp monomers and 9 Nsb monomers, 8 Nhp monomers and 8 Nsb monomers, 10 Nhp monomers and 6 Nsb monomers, 12 Nhp monomers and 4 Nsb monomers, or 16 Nhp monomers.

In some embodiments, the sequence length of the peptoid polymer, n, is 22, and the peptoid polymer comprises: 7 Nhp monomers and 15 Nsb monomers, 10 Nhp monomers and 12 Nsb monomers, 11 Nhp monomers and 11 Nsb monomers, 14 Nhp monomers and 8 Nsb monomers, 17 Nhp monomers and 5 Nsb monomers, or 22 Nhp monomers.

In some embodiments, the polymer is selected from the group of polymers set forth in Table 2, Table 3, Table 4, Table 5, Table 6, Table 7, Table 8, or Table 9.

In some embodiments, the peptoid polymer described herein forms a helical structure.

In some embodiments, the peptoid polymer reduces or inhibits ice crystal formation at a temperature within about 0° C. to about −20° C. In other embodiments, the peptoid polymer reduces or inhibits ice crystal formation at a temperature within about −20° C. to about −40° C. In some embodiments, the peptoid polymer reduces or inhibits ice crystal formation at about −20° C. In other embodiments, the peptoid polymer reduces or inhibits ice crystal formation at a temperature within about −40° C. to about −200° C. (e.g., −196° C.). In certain embodiments, the concentration of the peptoid polymer (e.g., present in a composition, formulation, or product such as a cryoprotectant solution, antifreeze solution, frozen food product, or cosmetic care product) is between about 100 nM and about 100 mM. In particular embodiments, the concentration of the peptoid polymer is between about 1 and 10 mM (e.g., about 1, 2, 3, 4, 5, 6, 7, 8, 9, or 10 mM).

In another aspect, the present invention provides a peptoid-peptide hybrid comprising a peptoid polymer described herein and one or more amino acids, wherein the one or more amino acids are located at one or both ends of the peptoid polymer and/or between one or more peptoid monomers. In some embodiments, the one or more amino acids are selected from the group consisting of alanine, cysteine, aspartic acid, glutamic acid, phenylalanine, glycine, histidine, isoleucine, arginine, lysine, leucine, methionine, asparagine, proline, glutamine, serine, threonine, valine, tryptophan, tyrosine, and a combination thereof. In particular embodiments, the one or more amino acids are selected from the group consisting of isoleucine, leucine, serine, threonine, alanine, valine, arginine, and a combination thereof.

In another aspect, the present invention provides a cryoprotectant solution comprising a peptoid polymer described herein, a peptoid-peptide hybrid described herein, or a combination thereof. In some embodiments, the cryoprotectant solution further comprises a compound selected from the group consisting of an ionic species, a penetrating cryoprotectant, a non-penetrating cryoprotectant, an antioxidant, a cell membrane stabilizing compound, an aquaporin or other channel forming compound, an alcohol, a sugar, a sugar derivative, a nonionic surfactant, a protein, dimethyl sulfoxide (DMSO), polyethylene glycol (PEG), Ficoll®, polyvinylpyrrolidone, polyvinyl alcohol, hyaluronan, formamide, a natural or synthetic hydrogel, and a combination thereof.

In some instances, the cryoprotectant solution further comprises an alcohol selected from the group consisting of propylene glycol, ethylene glycol, glycerol, methanol, butylene glycol, adonitol, ethanol, trimethylene glycol, diethylene glycol, polyethylene oxide, erythritol, sorbitol, xythyritol, polypropylene glycol, 2-methyl-2,4-pentanediol (MPD), mannitol, inositol, dithioritol, 1,2-propanediol, and a combination thereof.

In some instances, the cryoprotectant solution further comprises a sugar that is selected from the group consisting of a monosaccharide, a disaccharide, a polysaccharide, and a combination thereof. In some instances, the sugar is a monosaccharide selected from the group consisting of glucose, galactose, arabinose, fructose, xylose, mannose, 3-O-Methyl-D-glucopyranose, and a combination thereof. In other instances, the sugar is a disaccharide selected from the group consisting of sucrose, trehalose, lactose, maltose, and a combination thereof. In still other instances, the sugar is a polysaccharide selected from the group consisting of raffinose, dextran, and a combination thereof.

In other instances, the cryoprotectant solution further comprises a PEG that has an average molecular weight less than about 1,000 g/mol. In particular instances, the PEG has an average molecular weight between about 200 and 400 g/mol.

In some instances, the cryoprotectant solution further comprises a protein selected from the group consisting of bovine serum albumin, human serum albumin, gelatin, and a combination thereof. In other instances, the cryoprotectant solution further comprises a natural or synthetic hydrogel that comprises chitosan, hyaluronic acid, or a combination thereof. In yet other instances, the cryoprotectant solution further comprises a nonionic surfactant selected from the group consisting of polyoxyethylene lauryl ether, polysorbate 80, and a combination thereof.

In another aspect, provided herein is a method for preserving a tissue, organ, or cell. The method comprises contacting the tissue, organ, or cell with a peptoid polymer described herein, a peptoid-peptide hybrid described herein, a cryoprotectant solution described herein, or a combination thereof. In some embodiments, the tissue is a bioengineered tissue. In some embodiments, the tissue, organ, or cell is selected from the group consisting of heart, liver, lung, kidney, pancreas, intestine, thymus, cornea, nerve cells, blood platelets, sperm cells, oocytes, embryonic cells, stem cells (e.g., human pluripotent stem cells, hematopoietic stem cells), lymphocytes, granulocytes, immune system cells, bone cells, organoids, and a combination thereof.

In some embodiments, the peptoid polymer, peptoid-peptide hybrid, cryoprotectant solution, or combination thereof is present in an amount sufficient to reduce or inhibit ice crystal formation at a temperature within about 0° C. to about −20° C. In other embodiments, the peptoid polymer, peptoid-peptide hybrid, cryoprotectant solution, or combination thereof is present in an amount sufficient to reduce or inhibit ice crystal formation at a temperature within about −20° C. to about −40° C. In some embodiments, the peptoid polymer, peptoid-peptide hybrid, cryoprotectant solution, or combination thereof is present in an amount sufficient to reduce or inhibit ice crystal formation at about −20° C. In other embodiments, the peptoid polymer, peptoid-peptide hybrid, cryoprotectant solution, or combination thereof is present in an amount sufficient to reduce or inhibit ice crystal formation at a temperature within about −40° C. to about −200° C. (e.g., −196° C.). In certain embodiments, the concentration of the peptoid polymer and/or peptoid-peptide hybrid in the cryoprotectant solution is between about 100 nM and about 100 mM. In particular embodiments, the concentration of the peptoid polymer and/or peptoid-peptide hybrid in the cryoprotectant solution is between about 1 and 10 mM (e.g., about 1, 2, 3, 4, 5, 6, 7, 8, 9, or 10 mM).

In yet another aspect, provided herein is a method for preserving a biological macromolecule. The method comprises contacting the biological macromolecule with a peptoid polymer described herein, a peptoid-peptide hybrid described herein, a cryoprotectant solution described herein, or a combination thereof. In some embodiments, the biological macromolecule is selected from the group consisting of a nucleic acid, an amino acid, a protein, an isolated protein, a peptide, a lipid, a composite structure, and a combination thereof.

In another aspect, the present invention provides a cosmetic care product comprising a peptoid polymer described herein, a peptoid-peptide hybrid described herein, a cryoprotectant solution described herein, or a combination thereof.

In another aspect, the present invention provides an antifreeze product such as a deicing or ice-inhibiting product comprising a peptoid polymer described herein, a peptoid-peptide hybrid described herein, a cryoprotectant solution described herein, or a combination thereof. In some embodiments, the antifreeze product is used to prevent, inhibit, or delay the formation of ice on objects including, but not limited to, aircrafts or parts thereof, gas pipelines, windows, electrical equipment, drones, cables (e.g., power lines), mechanical equipment (e.g., car engines, gear systems, brake systems, etc.), and the like.

In still another aspect, the present invention provides a frozen food product comprising a peptoid polymer described herein, a peptoid-peptide hybrid described herein, a cryoprotectant solution described herein, or a combination thereof. In some embodiments, the frozen food product is selected from the group consisting of ice cream, yogurt, seafood, fruit, and meat products.

Other objects, features, and advantages of the present invention will be apparent to one of skill in the art from the following detailed description and figures.

BRIEF DESCRIPTION OF THE DRAWINGS

FIG. 2A illustrates the assay in which Compounds 1 (1 eq.) and 10 (1 eq.) were dissolved in MilliQ water and subjected to subzero temperatures. Comparison was made to water alone and a solution of ethylene glycol (EG) (18 eq.). FIG. 2B displays normalized results of the assay depicted in FIG. 2A.

FIGS. 3A-3D show x-ray diffraction (XRD) crystallography data. FIG. 3A shows XRD data for a solution containing 5 mM Compound 12 and 17.5% (v/v) ethylene glycol (EG). FIG. 3B shows XRD data for a solution containing 30% (v/v) EG. FIG. 3C shows XRD data for a solution containing 17.5% (v/v) EG. FIG. 3D shows ice ring scores for a number of solutions containing EG, Compound 2 (labeled as "B"; SEQ ID NO:10), Compound 12 (labeled as "D"; SEQ ID NO:8), and/or Compound 8 (labeled as "E"; SEQ ID NO:9). For each different solution, two separate ice ring scores were determined.

FIG. 4A: Compound 10 XRD crystallography pattern (left) and spectrum plot (right). FIG. 4B: Compound 12 XRD crystallography pattern (left) and spectrum plot (right). FIG. 4C: Compound 8 XRD crystallography pattern (left) and spectrum plot (right). FIG. 4D: Compound 13 XRD crystallography pattern (left) and spectrum plot (right). FIG. 4E: Compound 11 XRD crystallography pattern (left) and spectrum plot (right). FIG. 4F: Compound 58 XRD crystallography pattern (left) and spectrum plot (right). FIG. 4G: EG control XRD crystallography pattern (left) and spectrum plot (right). For XRD spectrum plots, intensity was plotted as a function of angle (2θ degrees).

FIG. 5A: Compound 10 XRD crystallography pattern (left) and spectrum plot (right). FIG. 5B: Compound 12 XRD crystallography pattern (left) and spectrum plot (right). FIG. 5C: Compound 8 XRD crystallography pattern (left) and spectrum plot (right). FIG. 5D: Compound 13 XRD crystallography pattern (left) and spectrum plot (right). FIG. 5E: Compound 11 XRD crystallography pattern (left) and spectrum plot (right). FIG. 5F: Compound 58 XRD crystallography pattern (left) and spectrum plot (right). FIG. 5G: EG control XRD crystallography pattern (left) and spectrum plot (right). For XRD spectrum plots, intensity was plotted as a function of angle (2θ degrees).

FIG. 6A shows that during rapid freezing in liquid nitrogen, the solution containing Compound 12 vitrified while the control solution completely froze. FIG. 6B shows that during rewarming at 37° C., the solution containing Compound 12 unfroze (within two seconds) while the control stayed frozen. FIG. 6C shows that after overnight in a −20° C. freezer, the Compound 12 solution remained unfrozen, unlike the control.

DETAILED DESCRIPTION OF THE INVENTION

I. Introduction

Figure 1:
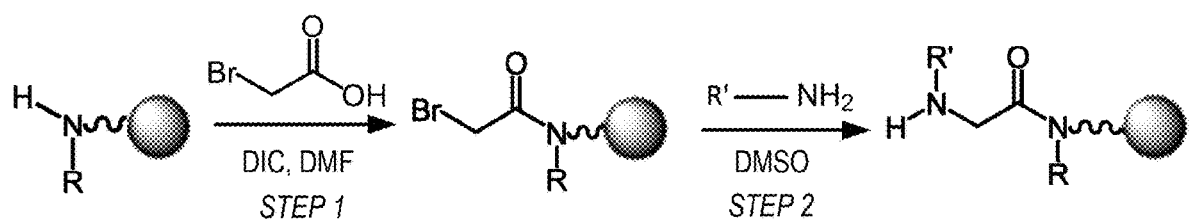
FIG. 1 illustrates a general protocol for the synthesis of peptoid oligomers using the "submonomer" approach.

The banking of cells and tissues at low temperatures using cryopreservation is critical for many biological products and applications, but remains a significant problem that has yet to allow the successful full recovery or viable therapeutic cells, tissues, and organs. Cryopreservation is typically performed with cryoprotective agents (CPAs), which are critical chemical additives such as dimethyl sulfoxide (DMSO), bovine serum albumin (BSA), and others. The CPAs are used to improve the post-thaw viability of cryopreserved biological systems by preventing ice crystal nucleation and growth. However, these agents exhibit various levels of cytotoxicity at their effective concentrations and thus limit the success of cryopreservation, biobanking, and advanced regenerative medicine. This lack of an effective and safe CPA contributes to the widespread use of toxic CPAs. Beyond biological products and applications, preventing ice formation remains a physical and chemical problem for a wide variety of industries and technology sectors.

The present invention is based, in part, on the surprising discovery that N-substituted biomimetic amino acid polymers (peptoids) and peptoid-peptide hybrids have ice crystallization inhibition properties. Provided herein are polymers for reducing or inhibiting ice crystal formation at sub 0° C. and cryogenic temperatures. These polymers are useful in making cryoprotectant solutions. Also provided herein are methods for preserving a tissue, organ, or cell using cryoprotectant solutions comprising the peptoid polymers described herein. Additionally, cosmetic care, deicing, and frozen food products with antifreeze properties comprising the peptoid polymers described herein are provided. Upon reading the detailed description, a person of ordinary skill in the art will recognize there are other advantages that flow from the teachings provided herein.

II. Abbreviations and Definitions

The abbreviations used herein are conventional, unless otherwise defined. The following abbreviations are used to refer to the monomer units of the peptoid polymer: Nsb (2-(sec-butylamino)acetic acid), Nib (2-(isobutylamino)acetic acid), Nbu (2-butylamino)acetic acid), Npr (2-propylamino)acetic acid), Nip (2-(isopropylamino)acetic acid), Nine (2-(methylamino)acetic acid), Nhp (2-((2-hydroxypropyl)amino)acetic acid), Nhe (2-((2-hydroxyethyl)amino) acetic acid), Ndp (2-((2,3-dihydroxypropryl)amino)acetic acid, Nyp (2-((1-hydroxypropan-2-yl)amino) acetic acid), Nep (2-((1-(4-hydroxyphenyl)ethyl)amino) acetic acid, Ndh (2-((1,3,-dihydrooxypropan-2-yl)amino)acetic acid, and Nop (2-((3-(2-oxopyrrolindin-1-yl)propyl)amino)acetic acid. The following abbreviations are used to refer to chemical compounds: DMF (N, N'-dimethylformamide), DIEA (diisopropylethylamine, DIC (N, N'-diisopropylcarbodiimide), ACN (acetonitrile), DCM (methylene chloride), HFIP (hexafluoroisopropyl alcohol); Fmoc (9-fluorenylmethoxycarbonyl).

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The term "about" as used herein to modify a numerical value indicates a defined range around that value. If "X" were the value, "about X" would indicate a value from 0.9X to 1.1X, and more preferably, a value from 0.95X to 1.05X. Any reference to "about X" specifically indicates at least the values X, 0.95X, 0.96X, 0.97X, 0.98X, 0.99X, 1.01X, 1.02X, 1.03X, 1.04X, and 1.05X. Thus, "about X" is intended to teach and provide written description support for a claim limitation of, e.g., "0.98X."

"Alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 30 carbons atoms, such as, but not limited to heptyl, octyl, nonyl, decyl, etc. Alkyl groups can be substituted or unsubstituted. Alkyl groups can be optionally substituted with one or more moieties selected from halo, hydroxy, amino, thiol, alkylamino, alkoxy, haloalkyl, carboxy, amido, nitro, oxo, thioxo, and cyano.

"Alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can be substituted or unsubstituted. Alkenyl groups can be optionally substituted with one or more moieties selected from halo, hydroxy, amino, thiol, alkylamino, alkoxy, haloalkyl, carboxy, amido, nitro, oxo, thioxo, and cyano.

"Alkynyl" refers to either a straight chain or branched hydrocarbon having at least 2 carbon atoms and at least one triple bond. Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can be substituted or unsubstituted. Alkynyl groups can be optionally substituted with one or more moieties selected from halo, hydroxy, amino, thiol, alkylamino, alkoxy, haloalkyl, carboxy, amido, nitro, oxo, thioxo, and cyano.

"Alkylene" refers to a straight or branched, saturated, aliphatic radical having the number of carbon atoms indicated, and linking at least two other groups, i.e., a divalent hydrocarbon radical. The two moieties linked to the alkylene can be linked to the same atom or different atoms of the alkylene group. For instance, a straight chain alkylene can be the bivalent radical of $-(CH_2)_n-$, where n is any number of suitable carbon atoms. Representative alkylene groups include, but are not limited to, methylene, ethylene, propylene, isopropylene, butylene, isobutylene, sec-butylene, pentylene and hexylene. Alkylene groups can be substituted or unsubstituted. Alkylene groups can be optionally substituted with one or more moieties selected from halo, hydroxy, amino, thiol, alkylamino, alkoxy, haloalkyl, carboxy, amido, nitro, oxo, thioxo, and cyano.

"Alkenylene" refers to an alkenyl group, as defined above, linking at least two other groups, i.e., a divalent hydrocarbon radical. The two moieties linked to the alkenylene can be linked to the same atom or different atoms of the alkenylene. Alkenylene groups include, but are not limited to, ethenylene, propenylene, isopropenylene, butenylene, isobutenylene, sec-butenylene, pentenylene and hexenylene. Alkenylen groups can be substituted or unsubstituted. Alkenylene groups can be optionally substituted with one or more moieties selected from halo, hydroxy, amino, thiol, alkylamino, alkoxy, haloalkyl, carboxy, amido, nitro, oxo, thioxo, and cyano.

"Alkynylene" refers to an alkynyl group, as defined above, linking at least two other groups, i.e., a divalent hydrocarbon radical. The two moieties linked to the alkynylene can be linked to the same atom or different atoms of the alkynylene. Alkynylene groups include, but are not limited to, ethynylene, propynylene, isopropynylene, butynylene, sec-butynylene, pentynylene and hexynylene. Alkynylene groups can be substituted or unsubstituted. Alkynylene groups can be optionally substituted with one or more moieties selected from halo, hydroxy, amino, thiol, alkylamino, alkoxy, haloalkyl, carboxy, amido, nitro, oxo, thioxo, and cyano.

"Halogen" or "halo" refers to fluorine, chlorine, bromine and iodine.

"Amine" or "amino" refers to an —$N(R)_2$ group where the R groups can be hydrogen, alkyl, alkenyl, alkynyl, cycloalkyl, heterocycloalkyl, aryl, or heteroaryl, among others. The R groups can be the same or different. The amino groups can be primary (each R is hydrogen), secondary (one R is hydrogen) or tertiary (each R is other than hydrogen). The alkyl, alkenyl, alkynyl, cycloalkyl, heterocycloalkyl, aryl, or heteroaryl groups can be optionally substituted with one or more moieties selected from halo, hydroxy, amino, thiol, alkylamino, alkoxy, haloalkyl, carboxy, amido, nitro, oxo, thioxo, and cyano.

"Hydroxyl" or "hydroxy" refers to an —OH group. The hydroxyl can be at any suitable carbon atom.

"Thiol" refers to an —SH group. The thiol group can be at any suitable carbon atom.

"Oxo" refers to a double bonded O group (=O, —C(O)—). The oxo group can be at any suitable carbon atom.

"Thioxo" refers to a double bonded S group (=S). The thioxo group can be at any suitable carbon atom.

"Nitro" refers to a —$NO_2$ group. The nitro group can be at any suitable carbon atom.

"Carboxy" refers to a carboxylic acid group of the formula —C(O)OH or —$CO_2H$.

"Cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl. Cycloalkyl groups can be substituted or unsubstituted. Cycloalkyl groups can be optionally substituted with one or more moieties selected from alkyl, alkenyl, alkynyl, halo, hydroxy, amino, alkylamino, alkoxy, haloalkyl, carboxy, amido, thiol, nitro, oxo, thioxo, and cyano. For example, cycloalkyl groups can be substituted with $C_{1-6}$ alkyl or oxo (=O), among many others.

"Heterocycloalkyl" refers to a saturated ring system having from 3 to 12 ring members and from 1 to 4 heteroatoms of N, O and S. Additional heteroatoms can also be useful, including, but not limited to, B, Al, Si and P. The heteroatoms can also be oxidized, such as, but not limited to, —S(O)— and —$S(O)_2$—. Heterocycloalkyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. The heterocycloalkyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline. Heterocycloalkyl groups can be unsubstituted or substituted. Heterocycloalkyl groups can be optionally substituted with one or more moieties selected from alkyl, alkenyl, alkynyl, halo, hydroxy, amino, thiol, alkylamino, alkoxy, haloalkyl, carboxy, amido, nitro, oxo, thioxo, and cyano. For example, heterocycloalkyl groups can be substituted with $C_{1-6}$ alkyl or oxo (=O), among many others.

The heterocycloalkyl groups can be linked via any position on the ring. For example, aziridine can be 1- or 2-aziridine, azetidine can be 1- or 2-azetidine, pyrrolidine can be 1-, 2- or 3-pyrrolidine, piperidine can be 1-, 2-, 3- or 4-piperidine, pyrazolidine can be 1-, 2-, 3-, or 4-pyrazolidine, imidazolidine can be 1-, 2-, 3- or 4-imidazolidine, piperazine can be 1-, 2-, 3- or 4-piperazine, tetrahydrofuran can be 1- or 2-tetrahydrofuran, oxazolidine can be 2-, 3-, 4- or 5-oxazolidine, isoxazolidine can be 2-, 3-, 4- or 5-isoxazolidine, thiazolidine can be 2-, 3-, 4- or 5-thiazolidine, isothiazolidine can be 2-, 3-, 4- or 5-isothiazolidine, and morpholine can be 2-, 3- or 4-morpholine.

When heterocycloalkyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxazolidine, thiazolidine, isothiazolidine, morpholine, thiomorpholine, dioxane and dithiane. Heterocycloalkyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

"Aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted. Aryl groups can be optionally substituted with one or more moieties selected from alkyl, alkenyl, alkynyl, halo, hydroxy, amino, thiol, alkylamino, alkoxy, haloalkyl, carboxy, amido, nitro, oxo, thioxo, and cyano.

"Heteroaryl" refers to a monocyclic or fused bicyclic or tricyclic aromatic ring assembly containing 5 to 16 ring atoms, where from 1 to 5 of the ring atoms are a heteroatom such as N, O or S. Additional heteroatoms can also be useful, including, but not limited to, B, Al, Si and P. The heteroatoms can also be oxidized, such as, but not limited to, —S(O)— and —S(O)$_2$—. Heteroaryl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted. Heteroaryl groups can be optionally substituted with one or more moieties selected from alkyl, alkenyl, alkynyl, halo, hydroxy, amino, thiol, alkylamino, alkoxy, haloalkyl, carboxy, amido, nitro, oxo, thioxo, and cyano.

The heteroaryl groups can be linked via any position on the ring. For example, pyrrole includes 1-, 2- and 3-pyrrole, pyridine includes 2-, 3- and 4-pyridine, imidazole includes 1-, 2-, 4- and 5-imidazole, pyrazole includes 1-, 3-, 4- and 5-pyrazole, triazole includes 1-, 4- and 5-triazole, tetrazole includes 1- and 5-tetrazole, pyrimidine includes 2-, 4-, 5- and 6-pyrimidine, pyridazine includes 3- and 4-pyridazine, 1,2,3-triazine includes 4- and 5-triazine, 1,2,4-triazine includes 3-, 5- and 6-triazine, 1,3,5-triazine includes 2-triazine, thiophene includes 2- and 3-thiophene, furan includes 2- and 3-furan, thiazole includes 2-, 4- and 5-thiazole, isothiazole includes 3-, 4- and 5-isothiazole, oxazole includes 2-, 4- and 5-oxazole, isoxazole includes 3-, 4- and 5-isoxazole, indole includes 1-, 2- and 3-indole, isoindole includes 1- and 2-isoindole, quinoline includes 2-, 3- and 4-quinoline, isoquinoline includes 1-, 3- and 4-isoquinoline, quinazoline includes 2- and 4-quinoazoline, cinnoline includes 3- and 4-cinnoline, benzothiophene includes 2- and 3-benzothiophene, and benzofuran includes 2- and 3-benzofuran.

Some heteroaryl groups include those having from 5 to 10 ring members and from 1 to 3 ring atoms including N, O or S, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, isoxazole, indole, isoindole, quinoline, isoquinoline, quinoxaline, quinazoline, phthalazine, cinnoline, benzothiophene, and benzofuran. Other heteroaryl groups include those having from 5 to 8 ring members and from 1 to 3 heteroatoms, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, and isoxazole. Some other heteroaryl groups include those having from 9 to 12 ring members and from 1 to 3 heteroatoms, such as indole, isoindole, quinoline, isoquinoline, quinoxaline, quinazoline, phthalazine, cinnoline, benzothiophene, benzofuran and bipyridine. Still other heteroaryl groups include those having from 5 to 6 ring members and from 1 to 2 ring atoms including N, O or S, such as pyrrole, pyridine, imidazole, pyrazole, pyrazine, pyrimidine, pyridazine, thiophene, furan, thiazole, isothiazole, oxazole, and isoxazole.

"(Cycloalkyl)alkyl" refers to a radical having an alkyl component and a cycloalkyl component, where the alkyl component links the cycloalkyl component to the point of attachment. The alkyl component is as defined above, except that the alkyl component is at least divalent, an alkylene, to link to the cycloalkyl component and to the point of attachment. The alkyl component can include any number of carbons, such as $C_{1-6}$, $C_{1-2}$, $C_{1-3}$, $C_{1-4}$, $C_{1-5}$, $C_{2-3}$, $C_{2-4}$, $C_{2-8}$, $C_{2-6}$, $C_{3-4}$, $C_{3-8}$, $C_{3-6}$, $C_{4-8}$, $C_{4-6}$ and $C_{5-6}$. The cycloalkyl component is as defined within. Exemplary (cycloalkyl)alkyl groups include, but are not limited to, methyl-cyclopropyl, methyl-cyclobutyl, methyl-cyclopentyl and methyl-cyclohexyl.

"(Heterocycloalkyl)alkyl" refers to a radical having an alkyl component and a heterocycloalkyl component, where the alkyl component links the heterocycloalkyl component to the point of attachment. The alkyl component is as defined above, except that the alkyl component is at least divalent, an alkylene, to link to the heterocycloalkyl component and to the point of attachment. The alkyl component can include any number of carbons, such as $C_{0-6}$, $C_{1-2}$, $C_{1-3}$, $C_{1-4}$, $C_{1-8}$, $C_{1-6}$, $C_{2-3}$, $C_{2-4}$, $C_{2-8}$, $C_{2-6}$, $C_{3-4}$, $C_{3-8}$, $C_{3-6}$, $C_{4-8}$, $C_{4-6}$ and $C_{5-6}$. The heterocycloalkyl component is as defined above. (Heterocycloalkyl)alkyl groups can be substituted or unsubstituted.

"Arylalkyl" refers to a radical having an alkyl component and an aryl component, where the alkyl component links the aryl component to the point of attachment. The alkyl component is as defined above, except that the alkyl component is at least divalent, an alkylene, to link to the aryl component and to the point of attachment. The alkyl component can include any number of carbons, such as $C_{0-6}$, $C_{1-2}$, $C_{1-3}$, $C_{1-4}$, $C_{1-8}$, $C_{1-6}$, $C_{2-3}$, $C_{2-4}$, $C_{2-8}$, $C_{2-6}$, $C_{3-4}$, $C_{3-8}$, $C_{3-6}$, $C_{4-8}$, $C_{4-6}$ and $C_{5-6}$. The aryl component is as defined above. Examples of arylalkyl groups include, but are not limited to, benzyl and ethyl-benzene. Arylalkyl groups can be substituted or unsubstituted.

"Heteroarylalkyl" refers to a radical having an alkyl component and a heteroaryl component, where the alkyl component links the heteroaryl component to the point of attachment. The alkyl component is as defined above, except that the alkyl component is at least divalent, an alkylene, to link to the heteroaryl component and to the point of attachment. The alkyl component can include any number of carbons, such as $C_{0-6}$, $C_{1-2}$, $C_{1-3}$, $C_{1-4}$, $C_{1-5}$, $C_{1-6}$, $C_{2-3}$, $C_{2-4}$, $C_{2-8}$, $C_{2-6}$, $C_{3-4}$, $C_{3-8}$, $C_{3-6}$, $C_{4-8}$, $C_{4-6}$ and $C_{5-6}$. The heteroaryl component is as defined within. Heteroarylalkyl groups can be substituted or unsubstituted.

"Carboxyalkyl" refers to a carboxy group linked to an alkyl, as described above, and generally having the formula —$C_{1-8}$ alkyl-C(O)OH. Any suitable alkyl chain is useful. Carboxyalkyl groups can be optionally substituted with one or more moieties selected from halo, hydroxy, amino, thiol, alkylamino, alkoxy, haloalkyl, carboxy, amido, nitro, oxo, thioxo, and cyano.

"Acyl" refers to an alkyl that contains an oxo substituted carbon at the point of attachment (—C(O)—$C_{1-8}$ alkyl). Any suitable alkyl chain is useful. Acyl groups can be optionally substituted with one or more moieties selected from halo, hydroxy, amino, thiol, alkylamino, alkoxy, haloalkyl, carboxy, amido, nitro, oxo, thioxo, and cyano.

"Hydroxyalkyl" refers to an alkyl group, as defined above, where at least one of the hydrogen atoms is replaced with a hydroxy group. As for the alkyl group, hydroxyalkyl groups can have any suitable number of carbon atoms, such as $C_{1-6}$. Exemplary hydroxyalkyl groups include, but are not limited to, hydroxy-methyl, hydroxyethyl (where the hydroxy is in the 1- or 2-position), hydroxypropyl (where the hydroxy is in the 1-, 2- or 3-position), hydroxybutyl (where the hydroxy is in the 1-, 2-, 3- or 4-position), hydroxypentyl (where the hydroxy is in the 1-, 2-, 3-, 4- or 5-position), hydroxyhexyl (where the hydroxy is in the 1-, 2-, 3-, 4-, 5- or 6-position), 1,2-dihydroxyethyl, and the like. Hydroxyalkyl groups can be optionally substituted with one or more moieties selected from halo, thiol, amino, alkylamino, alkoxy, haloalkyl, carboxy, amido, nitro, oxo, thioxo, and cyano. One of skill in the art will appreciate that other hydroxyalkyl groups are useful in the present invention.

"Alkoxy" refers to an alkyl group having at least one bridging oxygen atom. The bridging oxygen atom can be anywhere within the alkyl chain (alkyl-O-alkyl) or the bridging oxygen atom can connect the alkyl group to the point of attachment (alkyl-O—). In some instances, the alkoxy contains 1, 2, 3, 4, or 5 bridging oxygen atoms. As for alkyl group, alkoxy groups can have any suitable number of carbon atoms, such as $C_{1-2}$, $C_{1-4}$, and $C_{1-6}$. Alkoxy groups include, for example, methoxy, ethoxy, propoxy, iso-propoxy, methyloxy-ethyloxy-ethyl ($C_1$—O—$C_2$—O—$C_2$—), etc. One example of an alkoxy group is polyethylene glycol (PEG) wherein the polyethylene glycol chain can include between 2 to 20 ethylene glycol monomers. Alkoxy groups can be optionally substituted with one or more moieties selected from halo, hydroxy, amino, thiol, alkylamino, haloalkyl, carboxy, amido, nitro, oxo, thioxo, and cyano. Alkoxy groups can be substituted or unsubstituted.

"Alkylamino" refers to an alkyl group as defined within, having one or more amino groups. The amino groups can be primary, secondary or tertiary. Alkylamino groups useful in the present invention include, but are not limited to, ethyl amine, propyl amine, isopropyl amine, ethylene diamine and ethanolamine. The amino group can link the alkylamino to the point of attachment with the rest of the compound, be at any position of the alkyl group, or link together at least two carbon atoms of the alkyl group. Alkylamino groups can be optionally substituted with one or more moieties selected from halo, hydroxy, thiol, alkylamino, alkoxy, haloalkyl, carboxy, amido, nitro, oxo, thioxo, and cyano. One of skill in the art will appreciate that other alkylaminos are useful in the present invention.

"Alkylthio" refers to an alkyl group as defined within, having one or more thiol groups. Alkylthio groups useful in the present invention include, but are not limited to, ethyl thiol, propyl thiol, and isopropyl thiol. The thiol group can link the alkylthio to the point of attachment with the rest of the compound, be at any position of the alkyl group, or link together at least two carbon atoms of the alkyl group. Alkylthio groups can be optionally substituted with one or more moieties selected from halo, hydroxy, amino, alkylamino, alkoxy, haloalkyl, carboxy, amido, nitro, oxo, thioxo, and cyano. One of skill in the art will appreciate that other alkylthio are useful in the present invention.

The term "wavy line" signifies the point of attachment of the substituent to the remainder of the molecule. When the wavy line is not depicted as being specifically appended to a specific ring atom, the point of attachment can be to any suitable atom of the substituent. For example, the wavy line in the following structure:

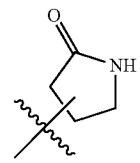

is intended to include, as the point of attachment, any of the substitutable atoms.

The term "regenerative medicine" refers to a branch of medicine that deals with the process of replacing, engineering or regenerating human cells, tissues, or organs to restore or establish normal function. In some embodiments, regenerative medicine includes growing tissues and organs in the laboratory and safely implanting them when the body cannot heal itself.

The term "bioengineered tissue" refers to one or more synthetically created cells, tissues, or organs created for the purposes of regenerative medicine. In some embodiments, bioengineered tissue refers to cells, tissues, or organs that were developed in the laboratory. In some embodiments, bioengineered tissues refers to laboratory derived heart, liver, lung, kidney, pancreas, intestine, thymus, cornea, stem cells (e.g., human pluripotent stem cells, hematopoietic stem cells), lymphocytes, granulocytes, immune system cells, bone cells, organoids, embryonic cells, oocytes, sperm cells, blood platelets, nerve cells, or a combination thereof.

The term "cryoprotectant solution" refers to a solution used to reduce or prevent freezing damage caused by ice crystal formation. In some embodiments, the cryoprotectant solution comprises one or more peptoid polymers described herein. In other embodiments, the cryoprotectant solution comprises one or more peptoid polymers and one or more peptoid-peptide hybrids described herein. In some embodiments, the cryoprotectant solution protects a biological sample from freezing damage. In some embodiments, the cryoprotectant solution protects a non-biological sample from ice crystal formation. In some embodiments, the cryoprotectant solution preserves a biological sample for an amount of time longer than if the biological sample were not exposed to reduced temperatures.

The terms "vitrify" and "vitrification" mean the transformation of a substance into a glass (i.e., non-crystalline amorphous solid). In the context of water, vitrification refers to the transformation of water into a glass without the formation of ice crystals, as opposed to ordinary freezing, which results in ice crystal formation. Vitrification is often achieved through very rapid cooling and/or the introduction of agents that suppress ice crystal formation. On the other hand, "devitrify" and "devitrification" refer to the process of crystallization in a previously crystal-free (amorphous) glass. In the context of water ice, devitrification can mean the formation of ice crystals as the previously non-crystalline amorphous solid undergoes melting.

The term "peptoid" refers to a polyamide of between about 2 and 1,000 (e.g., between about 2 and 1,000, 2 and 950, 2 and 900, 2 and 850, 2 and 800, 2 and 750, 2 and 700, 2 and 650, 2 and 600, 2 and 550, 2 and 500, 2 and 450, 2 and 400, 2 and 350, 2 and 300, 2 and 250, 2 and 200, 2 and 150, 2 and 100, 2 and 90, 2 and 80, 2 and 70, 2 and 60, 2 and 50, 2 and 40, 2 and 30, 2 and 20, 2 and 10, 2 and 9, 2 and 8, 2 and 7, 2 and 6, 2 and 5, 2 and 4, or 2 and 3) units having substituents "$R^1$" on the amide nitrogen atoms. Optionally, a second, independently selected, substituent "$R^2$" can be attached to the carbon atom that is α- to the carbonyl group (i.e., attached to the α-carbon atom). $R^2$ can be, but is not limited to, H. In particular instances, a peptoid is a synthetic analog of a peptide wherein the side chains that would otherwise be attached to the α-carbon atoms are instead attached to the amide nitrogen atoms. Peptoids are synthetic polymers with controlled sequences and lengths that can be made by automated solid-phase organic synthesis to include a wide variety of side-chains having different chemical functions. $R^1$ groups bonded to the amide nitrogen atoms in the peptoids can include, but are not limited to, H, optionally substituted $C_{1-18}$ alkyl, optionally substituted $C_{2-18}$ alkenyl, optionally substituted $C_{2-18}$ alkynyl, optionally substituted $C_{1-18}$ hydroxyalkyl, optionally substituted alkoxy, optionally substituted $C_{1-18}$ alkylamino, optionally substituted $C_{1-18}$ alkylthio, optionally substituted carboxyalkyl, $C_{3-10}$ cycloalkyl, heterocycloalkyl, aryl, heteroaryl, ($C_{3-10}$ cycloalkyl)alkyl, (heterocycloalkyl)alkyl, arylalkyl, and heteroarylalkyl groups, wherein any of the cycloalkyl, heterocycloalkyl, aryl, or heteroaryl groups is optionally and independently substituted with one or more "$R^3$" groups. Each $R^3$ group can be independently selected from halogen, oxo, thioxo, —OH, —SH, amino, $C_{1-8}$ alkyl, $C_{1-8}$ hydroxyalkyl, $C_{1-8}$ alkylamino, or $C_{1-8}$ alkylthio groups. Furthermore, $R^1$ groups can comprise the side chain of any of the amino acids alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), or tyrosine (Tyr).

The term "peptoid-peptide hybrid" refers to an oligomer that is composed of both peptoid monomer units and alpha amino acids (i.e., peptide units).

The terms "polypeptide," "peptide," and "protein" are used interchangeably herein to refer to a polymer of amino acid residues, or an assembly of multiple polymers of amino acid residues.

The term "amino acid" includes but is not limited to naturally-occurring α-amino acids and their stereoisomers. "Stereoisomers" of amino acids refers to mirror image isomers of the amino acids, such as L-amino acids or D-amino acids. For example, a stereoisomer of a naturally-occurring amino acid refers to the mirror image isomer of the naturally-occurring amino acid (i.e., the D-amino acid).

Naturally-occurring amino acids are those encoded by the genetic code, as well as those amino acids that are later modified (e.g., hydroxyproline, γ-carboxyglutamate, and O-phosphoserine). Naturally-occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of a naturally-occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

Amino acids may be referred to herein by either their commonly known three letter symbols or by the one-letter symbols recommended by the IUPAC-IUB Biochemical Nomenclature Commission. For example, an L-amino acid may be represented herein by its commonly known three letter symbol (e.g., Arg for L-arginine) or by an upper-case one-letter amino acid symbol (e.g., R for L-arginine). A D-amino acid may be represented herein by its commonly known three letter symbol (e.g., D-Arg for D-arginine) or by a lower-case one-letter amino acid symbol (e.g., r for D-arginine).

III-Detailed Description of the Embodiments

Provided herein are peptoid polymers and methods for reducing or inhibiting ice crystal formation at sub 0° C. temperatures and cryogenic temperatures.

A. Peptoid Polymers

In some aspects, provided herein is a peptoid polymer of formula (I):

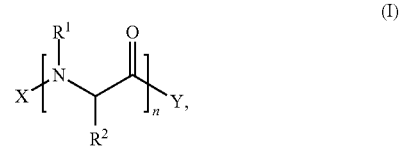

(I)

a tautomer thereof or stereoisomer thereof,
wherein:
each $R^1$ is independently selected from the group consisting of H, optionally substituted $C_{1-18}$ alkyl, optionally substituted $C_{2-18}$ alkenyl, optionally substituted $C_{2-18}$ alkynyl, optionally substituted $C_{1-18}$ hydroxyalkyl, optionally substituted alkoxy, optionally substituted $C_{1-18}$ alkylamino, optionally substituted $C_{1-18}$ alkylthio, optionally substituted carboxyalkyl, $C_{3-10}$ cycloalkyl, heterocycloalkyl, aryl, heteroaryl, ($C_{3-10}$ cycloalkyl)alkyl, (heterocycloalkyl)alkyl, arylalkyl, and heteroarylalkyl, wherein at least one instance of $R^1$ is $C_{1-18}$ hydroxyalkyl, and wherein any of the cycloalkyl, heterocycloalkyl, aryl, and heteroaryl groups is optionally and independently substituted with one or more $R^3$ groups;

each $R^2$ is independently selected from the group consisting of H, optionally substituted $C_{1-18}$ alkyl, optionally substituted $C_{2-18}$ alkenyl, optionally substituted $C_{2-18}$ alkynyl, optionally substituted $C_{1-18}$ hydroxyalkyl, optionally substituted $C_{1-18}$ alkylamino, optionally substituted $C_{1-18}$ alkylthio, and optionally substituted carboxyalkyl;

each $R^3$ is independently selected from the group consisting of halogen, oxo, thioxo, —OH, —SH, amino, $C_{1-8}$ alkyl, $C_{1-8}$ hydroxyalkyl, $C_{1-8}$ alkylamino, and $C_{1-8}$ alkylthio;

X and Y are independently selected from the group consisting of H, optionally substituted $C_{1-8}$ alkyl, optionally substituted $C_{1-8}$ acyl, optionally substituted $C_{1-8}$ alkylamino, —OH, —SH, —NH$_2$, carboxy, optionally substituted $C_{1-8}$ hydroxyalkyl, optionally substituted $C_{1-8}$ alkylamino, optionally substituted $C_{2-8}$alkylthio, optionally substituted $C_{1-8}$ carboxyalkyl, and halogen, or alternatively X and Y are taken together to form a covalent bond; and the subscript n, representing the number of monomers in the polymer, is between 2 and 50;

provided that all instances of $R^1$ are not hydroxyethyl when n is between 3 and 7.

In some embodiments, each instance of $R^1$ in the peptoid polymer is selected from the group consisting of:

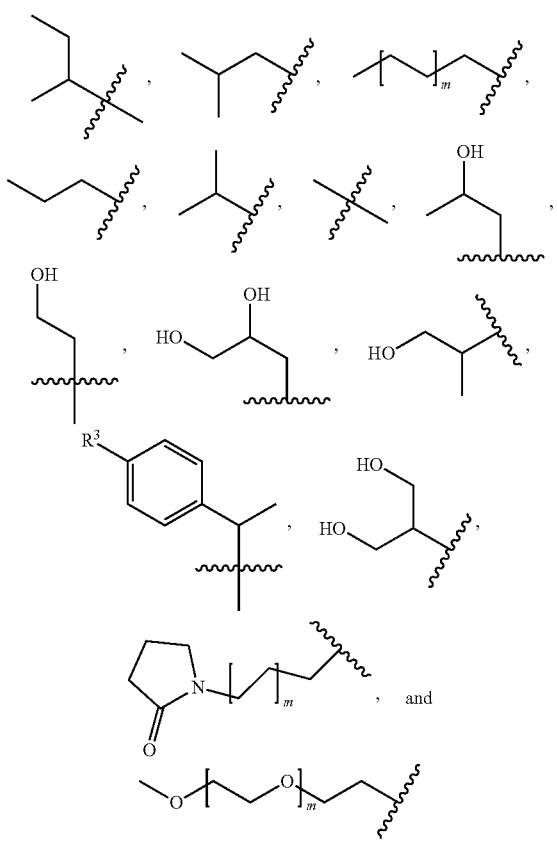

wherein: m is between 1 and 8; and $R^3$ is selected from the group consisting of H, $C_{1-8}$ alkyl, hydroxyl, thiol, nitro, amine, oxo, and thioxo. In some embodiments, the repeating unit, m, can be between 1 and 2, 1 and 3, 1 and 4, 1 and 5, 1 and 6, or 1 and 7. In some embodiments, the repeating unit, m, is 1, 2, 3, 4, 5, 6, 7, or 8.

In some embodiments, one or more $R^1$ monomers has a structure according to $R^{1a}$:

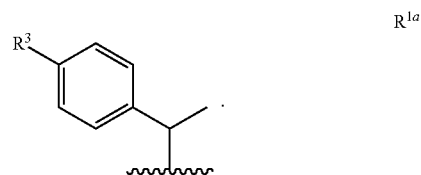

In some embodiments, each $R^{1a}$ group is independently selected from

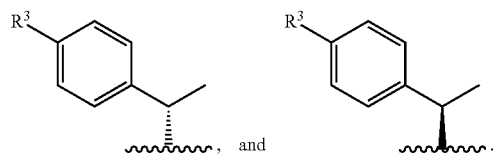

In some embodiments, a mixture of the two stereoisomers are chosen. In some embodiments, only the R stereoisomer of the monomer is chosen. In some embodiments, only the S stereoisomer of this monomer is chosen.

In some embodiments, one or more $R^1$ monomers has a structure according to $R^{1b}$:

In some embodiments, each $R^{1b}$ group is independently selected from

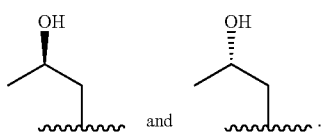

In some embodiments, a mixture of the two stereoisomers are chosen. In some embodiments, only the R stereoisomer of the monomer is chosen. In some embodiments, only the S stereoisomer of this monomer is chosen.

In some embodiments, one or more $R^1$ monomers has a structure according to $R^{1c}$:

$R^{1c}$

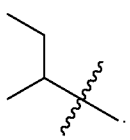

In some embodiments, each $R^{1c}$ group is independently selected from

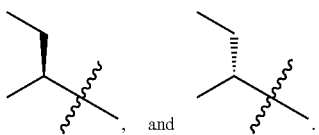

In some embodiments, a mixture of the two stereoisomers are chosen. In some embodiments, only the R stereoisomer of the monomer is chosen. In some embodiments, only the S stereoisomer of this monomer is chosen.

In some embodiments, one or more $R^1$ monomers has a structure according to Rid:

$R^{1d}$

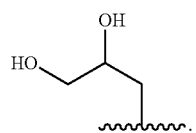

In some embodiments, each $R^{1d}$ group is independently selected from

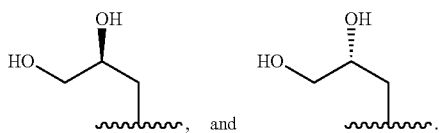

In some embodiments, a mixture of the two stereoisomers are chosen. In some embodiments, only the R stereoisomer of the monomer is chosen. In some embodiments, only the S stereoisomer of this monomer is chosen.

In some embodiments, one or more $R^1$ monomers has a structure according to $R^{ie}$:

$R^{1e}$

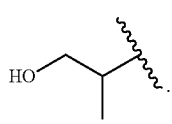

In some embodiments, each $R^{1e}$ group is independently selected from

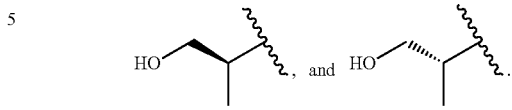

In some embodiments, a mixture of the two stereoisomers are chosen. In some embodiments, only the R stereoisomer of the monomer is chosen. In some embodiments, only the S stereoisomer of this monomer is chosen.

Whenever any monomer herein does not indicate stereochemistry, any stereoisomer may be used. In some embodiments, a mixture of the two stereoisomers are chosen. In embodiments comprising a mixture of stereoisomers, the ratio of R to S stereoisomer of the monomer in the peptoid polymer can range from about 95:5 to about 90:10, from about 90:10 to about 85:15, from about 85:15 to about 80:20, from about 80:20 to about 75:25, from about 75:25 to about 70:30, from about 70:30 to about 65:35, from about 65:35 to about 60:40, from about 60:40 to about 55:45, from about 55:45 to about 50:50, from about 50:50 to about 45:55, from about 45:55 to about 40:60, from about 40:60 to about 35:65, from about 35:65 to about 30:70, from about 30:70 to about 25:75, from about 25:75 to about 20:80, from about 20:80 to about 15:85, from about 15:85 to about 10:90, or from about 10:90 to about 5:95. In some embodiments, only the R stereoisomer of the monomer is chosen. In some embodiments, only the S stereoisomer of the monomer is chosen.

Whenever a particular stereochemistry is shown with a wedge or a dashed line, the monomer is substantially free of other stereoisomers. In some embodiments, substantially free means at least 70% pure. In some embodiments, substantially free means at least 80% pure. In some embodiments, substantially free means at least 90% pure. In some embodiments, substantially free means at least 95% pure. In some embodiments, substantially free means at least 99% pure. In some embodiments, substantially free means at least 99.9% pure.

In some embodiments, each instance of $R^1$ in the peptoid polymer is selected from the group consisting of:

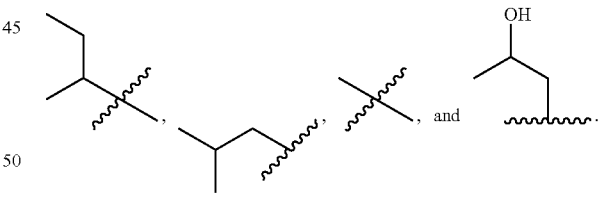

In some embodiments, at least 2, 3, 4, 5, 6, 7, 8, 9, 10, 11, 12, 13, 14, 15, 16, 17, 18, 19, 20, or more instances of $R^1$ in the peptoid polymer are independently selected $C_{1-18}$ hydroxyalkyl groups (e.g., independently selected $C_{1-6}$ hydroxyalkyl groups). In some embodiments, each instance of $R^1$ in the peptoid polymer is a $C_{1-18}$ hydroxyalkyl group. In some embodiments, each instance of $R^1$ is a $C_{1-6}$ hydroxyalkyl group. In some embodiments, each instance of $R^1$ is the same $C_{1-6}$ hydroxyalkyl group. In some embodiments, each instance of $R^1$ is an hydroxyalkyl group where the length of the alkyl in each hydroxyalkyl group is selected from 1, 2, 3, 4, 5, 6, 7, 8, 9, 10, 11, 12, 13, 14, 15, 16, 17, 18 or more carbon atoms. In some embodiments the hydroxyalkyl group contains 1, 2, 3, 4, 5, 6, 7, or 8 hydroxy substitutions. In some embodiments, each instance of $R^1$ is:

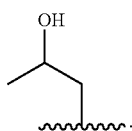

In some embodiments, each instance of $R^2$ is H. In some embodiments at least one $R^2$ is a halogen.

In some embodiments, the sequence length of the peptoid polymer, n, is between 3 and 25. In some embodiments, the sequence length of the peptoid polymer, n, is between 5 and 25. In some embodiments, the sequence length of the peptoid polymer, n, is between 8 and 50. In some embodiments, the sequence length of the peptoid polymer, n, is between 8 and 25. In some embodiments, the sequence length of the peptoid polymer, n, is between 8 and 20. In some embodiments, the sequence length of the peptoid polymer, n, can be between from about 10 to about 28, from about 12 to about 26, from about 14 to about 24, from about 16 to about 22, or from about 18 to about 20. In some embodiments, the sequence length of the peptoid polymer, n, can be between from about 8 to about 50, from about 8 to about 45, from about 8 to about 40, from about 8 to about 35, from about 8 to about 30, from about 10 to about 25, from about 10 to about 20, or from about 10 to about 15. In some embodiments, the sequence length of the peptoid polymer, n, can be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

In some embodiments, X and Y are H, optionally substituted $C_{1-8}$ alkylamino, —OH, —SH, carboxy, optionally substituted $C_{1-8}$ hydroxyalkyl, optionally substituted $C_{1-8}$ alkylamino, optionally substituted $C_{2-8}$ alkylthio, optionally substituted $C_{1-8}$ carboxyalkyl, or halogen.

In some embodiments, X and Y of the peptoid polymer are taken together to form a covalent bond. The formation of a covalent bond between X and Y results in a circularized form of the peptoid polymer in which the terminal $NR^1$ group and the terminal C=O group are linked, as shown below.

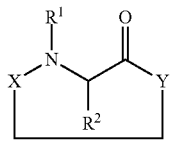

In some embodiments, the peptoid polymer consists of monomer units selected from the group of monomers set forth in Table 1. A person of skill in the art will recognize that the bounds of this invention are not limited to the monomers listed in Table 1, and that any useful N-substituted substituent can be used as an N-substituted peptoid monomer. In some embodiments, the N-substituted substituent on the N-substituted peptoid monomer is any of the side chains of the amino acids alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), or tyrosine (Tyr).

TABLE 1

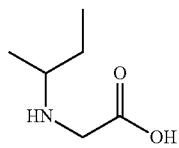

2-(sec-butylamino)acetic acid
Nsb

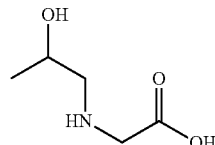

2-((2-hydroxypropyl)amino)acetic acid
Nhp

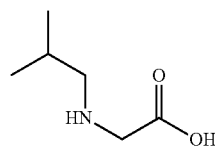

2-(isobutylamino)acetic acid
Nib

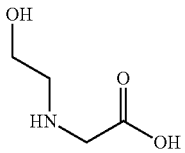

2-((2-hydroxyethyl)amino)acetic acid
Nhe

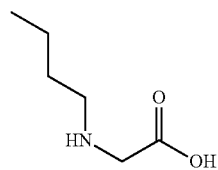

2-(butylamino)acetic acid
Nbu

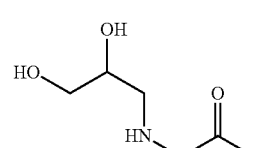

2-((2,3-dihydroxypropyl)amino)acetic acid
Ndp

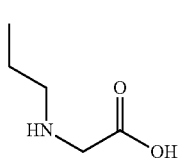

2-(propylamino)acetic acid
Npr

TABLE 1-continued

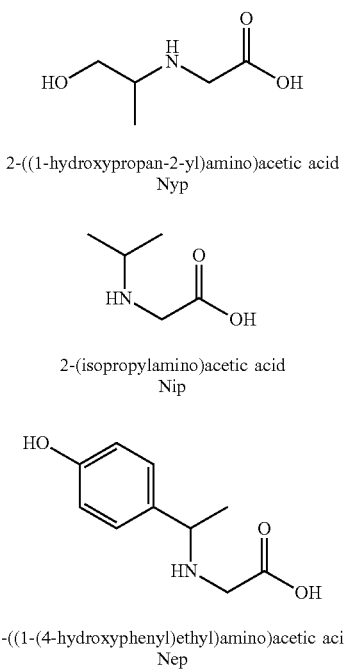

2-((1-hydroxypropan-2-yl)amino)acetic acid
Nyp 2-(isopropylamino)acetic acid
Nip 2-((1-(4-hydroxyphenyl)ethyl)amino)acetic acid
Nep

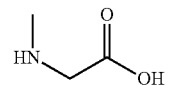

2-(methylamino)acetic acid
Nme

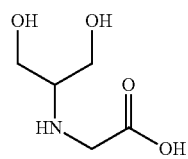

2-((1,3-dihydroxypropan-2-yl)amino)acetic acid
Ndh

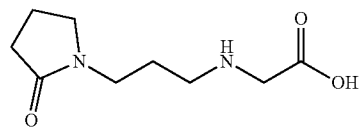 [SMILES: O=C(O)CNCCCN1CCCC1=O]

2-((3-(2-oxopyrrolidin-1-yl)propyl)amino)acetic acid
Nop

In some embodiments, the peptoid polymer is selected from the group of peptoid polymers set forth in Table 2, Table 3, Table 4, Table 5, Table 6, Table 7, Table 8, or Table 9.

TABLE 2

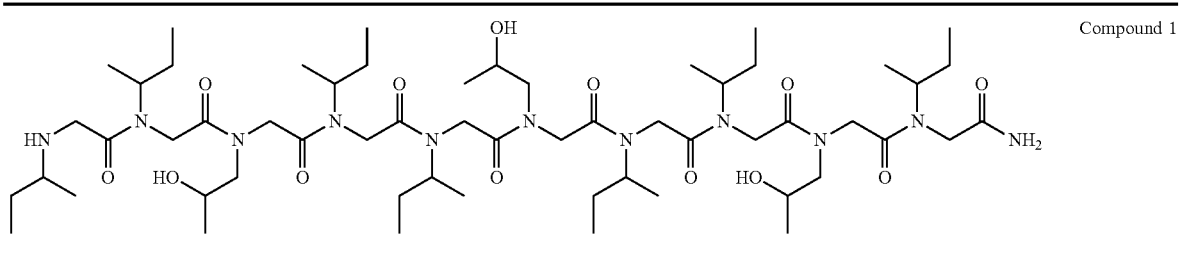
Compound 1

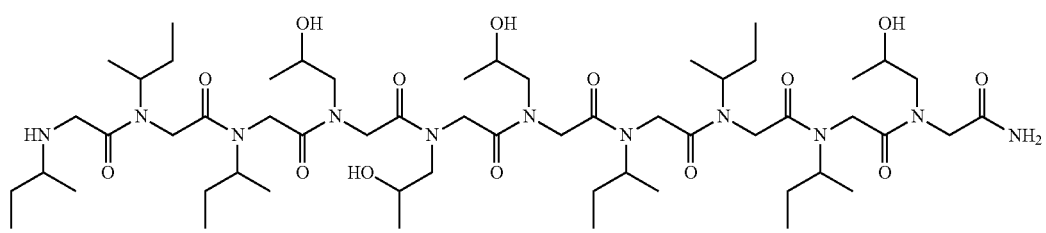 [SMILES: CCC(C)NCC(=O)N(CC(=O)N(CC(=O)N(CC(=O)N(CC(=O)N(CC(=O)N(CC(=O)N(CC(=O)N(CC(=O)N(CC(N)=O)CC(C)O)C(C)CC)C(C)CC)C(C)CC)CC(C)O)CC(C)O)CC(C)O)C(C)CC)C(C)CC]
Compound 2

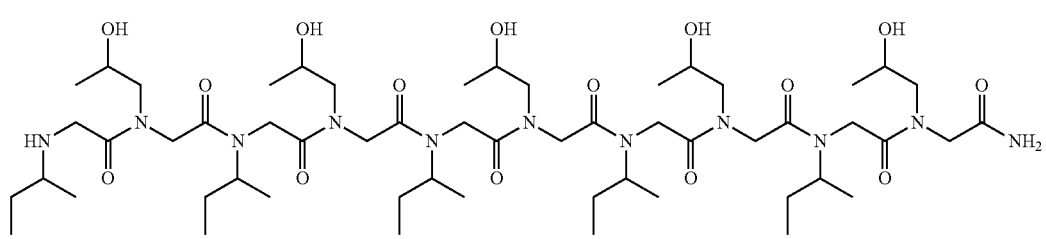 [SMILES: CCC(C)NCC(=O)N(CC(=O)N(CC(=O)N(CC(=O)N(CC(=O)N(CC(=O)N(CC(=O)N(CC(=O)N(CC(=O)N(CC(N)=O)CC(C)O)C(C)CC)CC(C)O)C(C)CC)CC(C)O)C(C)CC)CC(C)O)C(C)CC)CC(C)O]
Compound 3

TABLE 2-continued
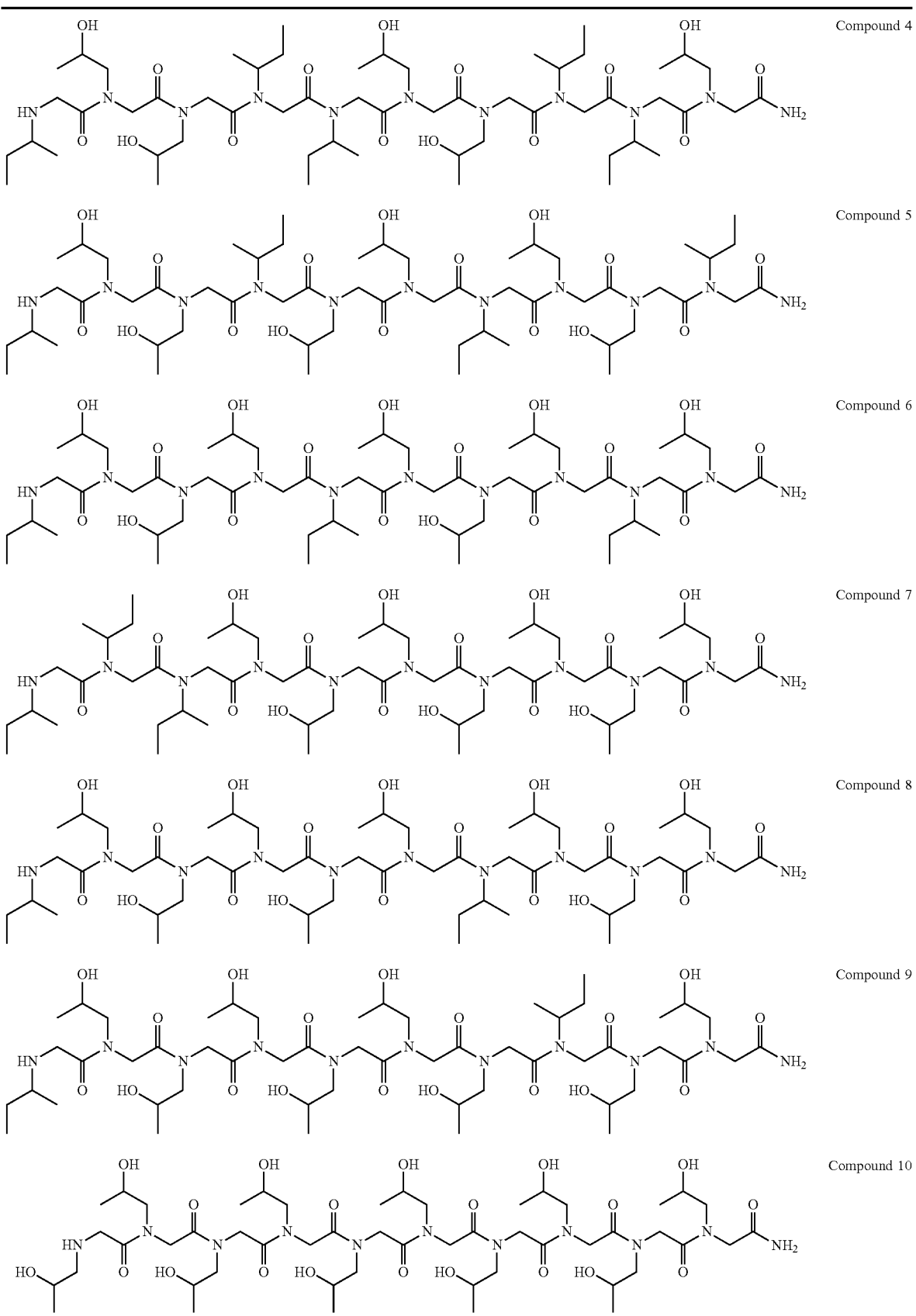

TABLE 2-continued
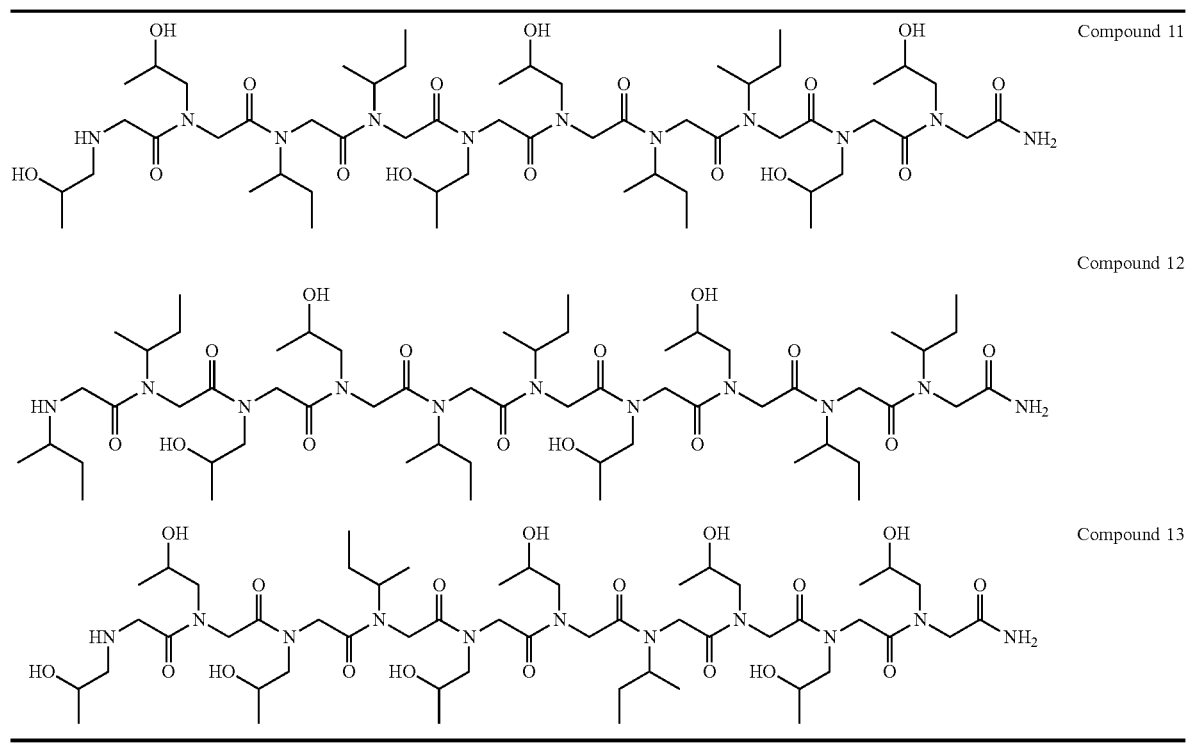
Compound 11
Compound 12
Compound 13
TABLE 3
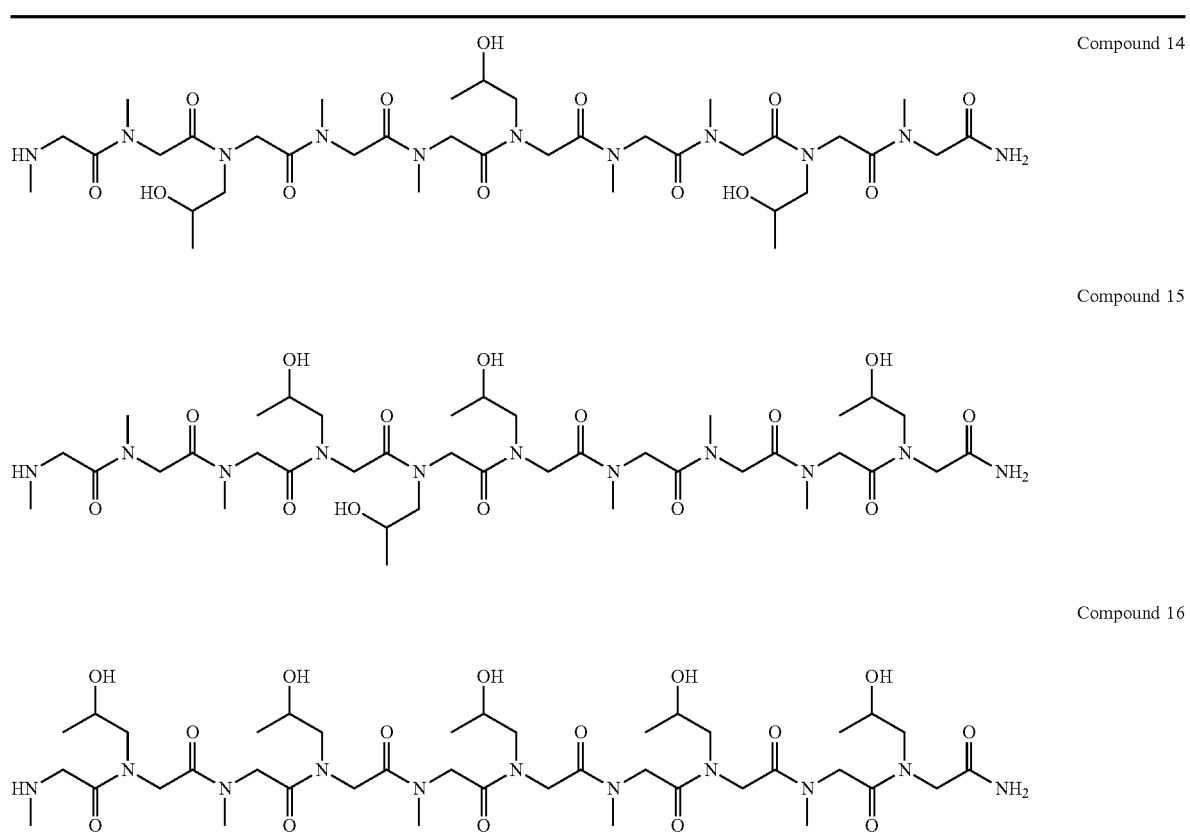
Compound 14
Compound 15
Compound 16

TABLE 3-continued
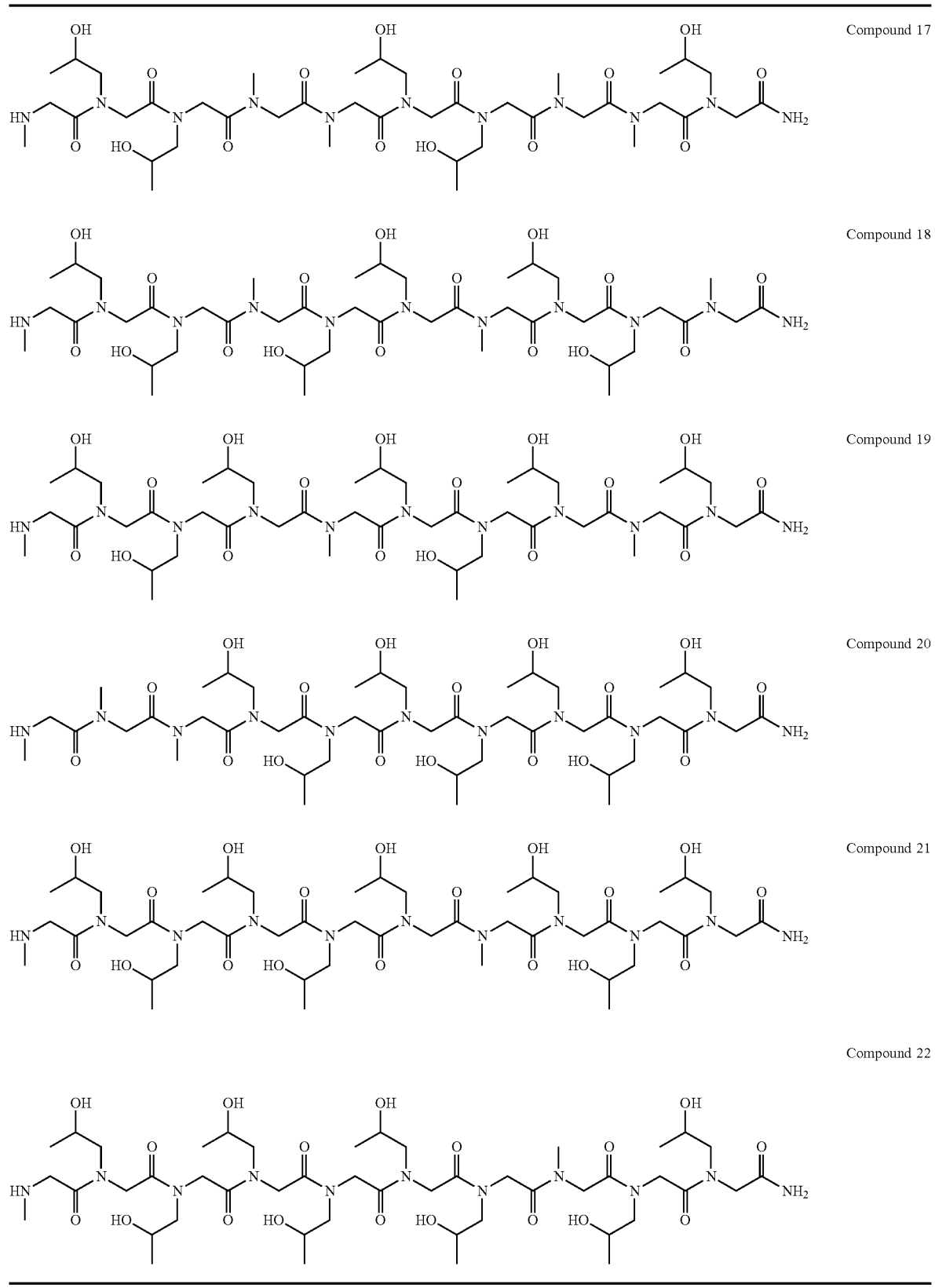

TABLE 4
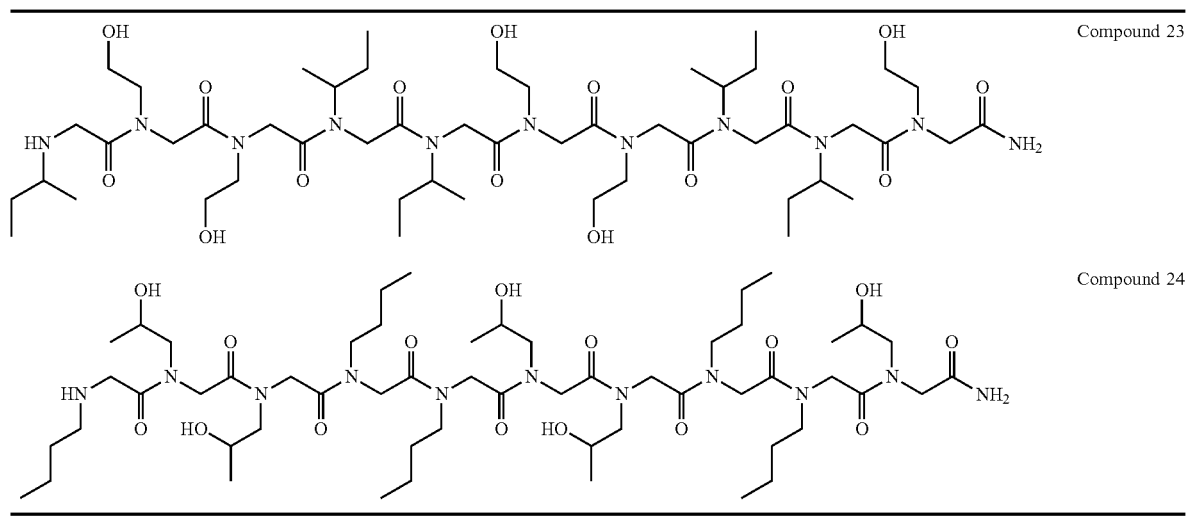
TABLE 5
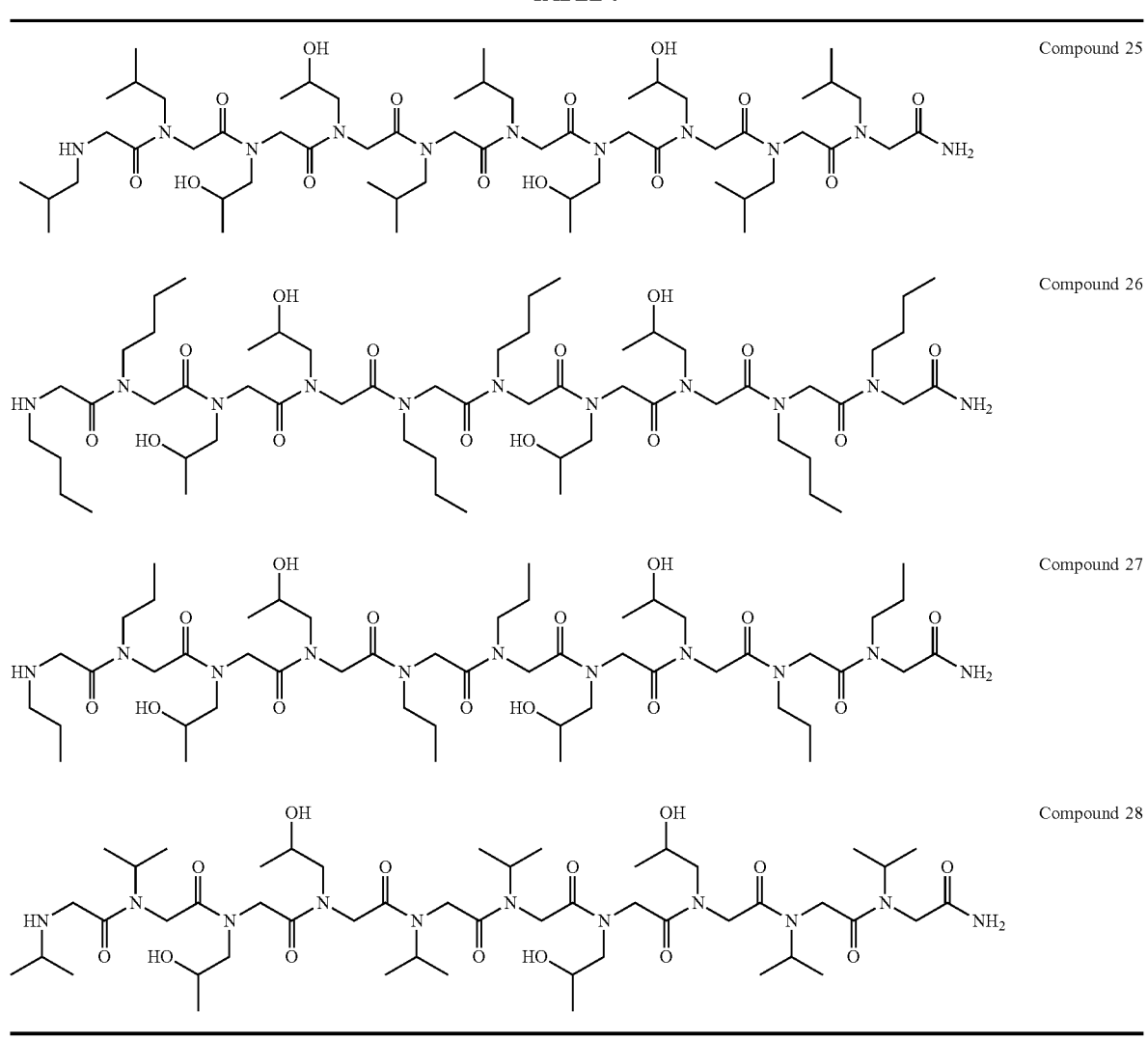

TABLE 6
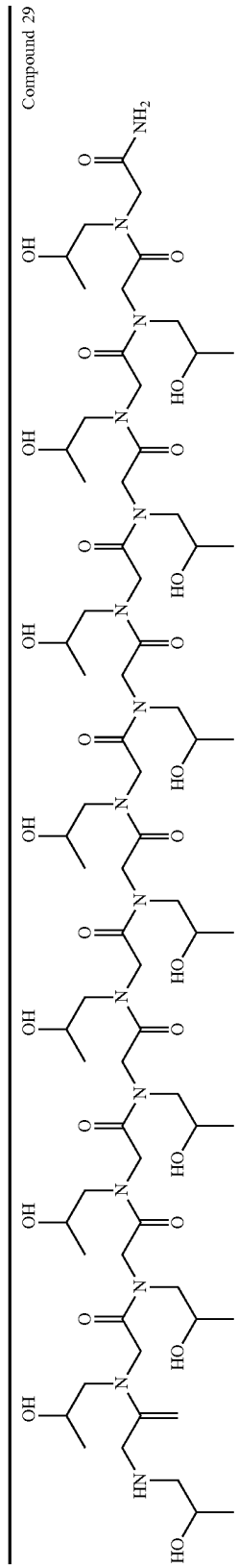
Compound 29
Compound 30
Compound 31

TABLE 6-continued
Compound 32
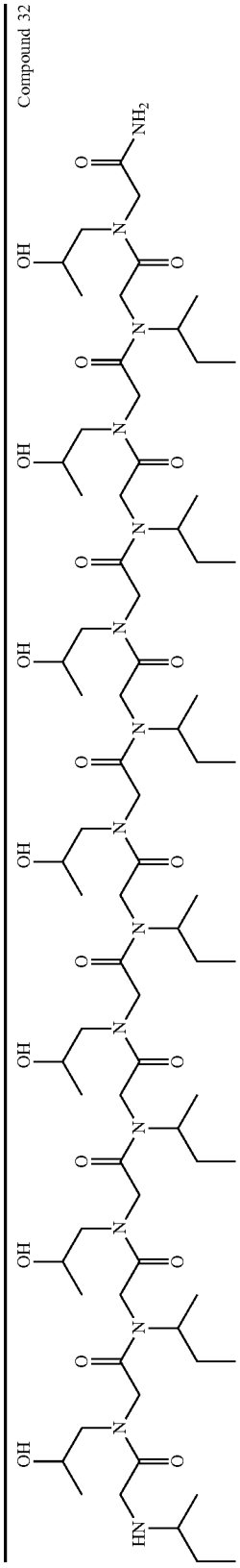
Compound 33
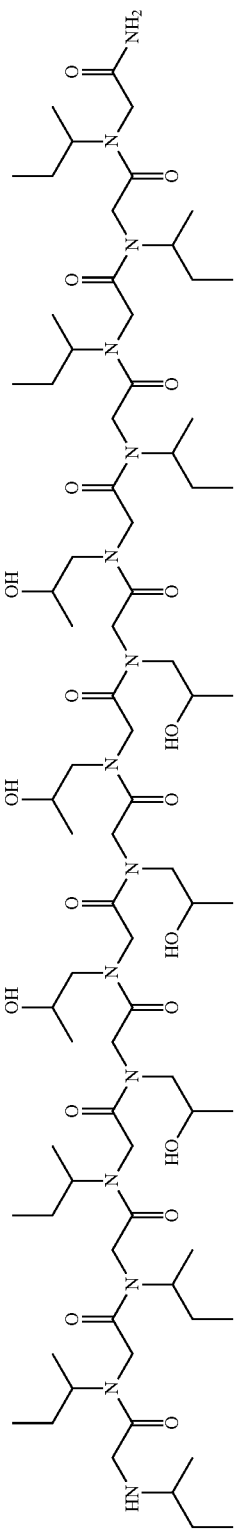
Compound 34
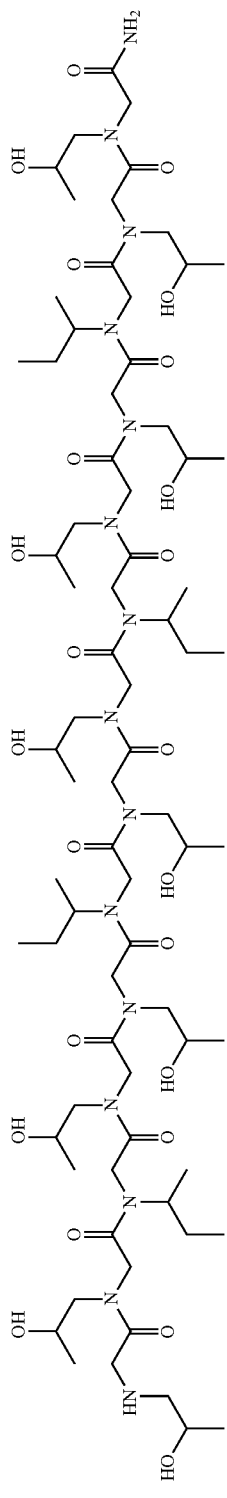

TABLE 7

Compound 35, Compound 36, Compound 37

TABLE 7-continued
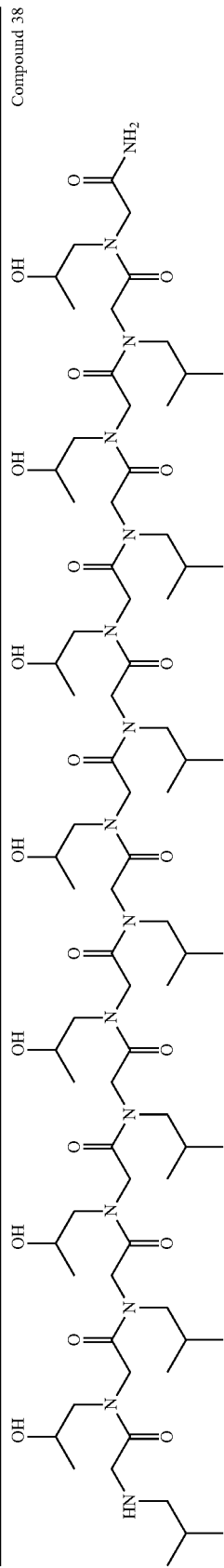
Compound 38
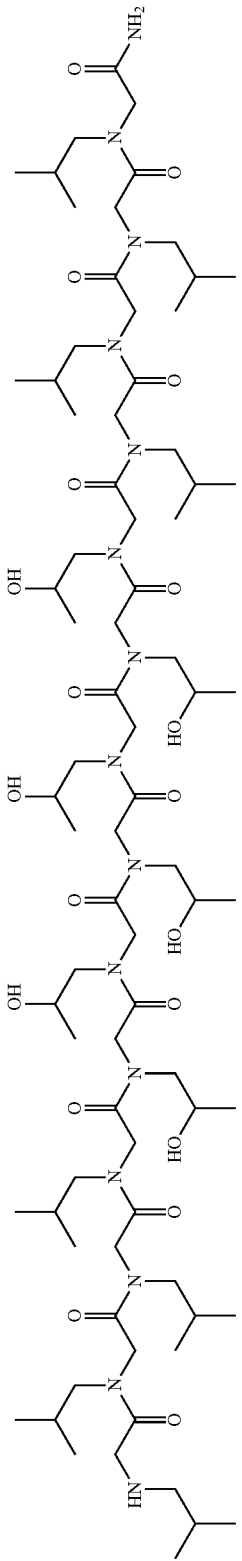
Compound 39
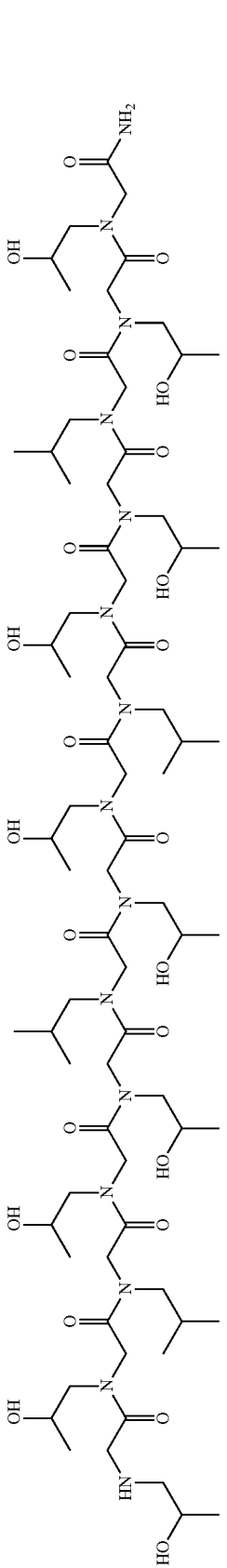
Compound 40

TABLE 8

Compound 41, Compound 42, Compound 43, Compound 44

TABLE 8-continued
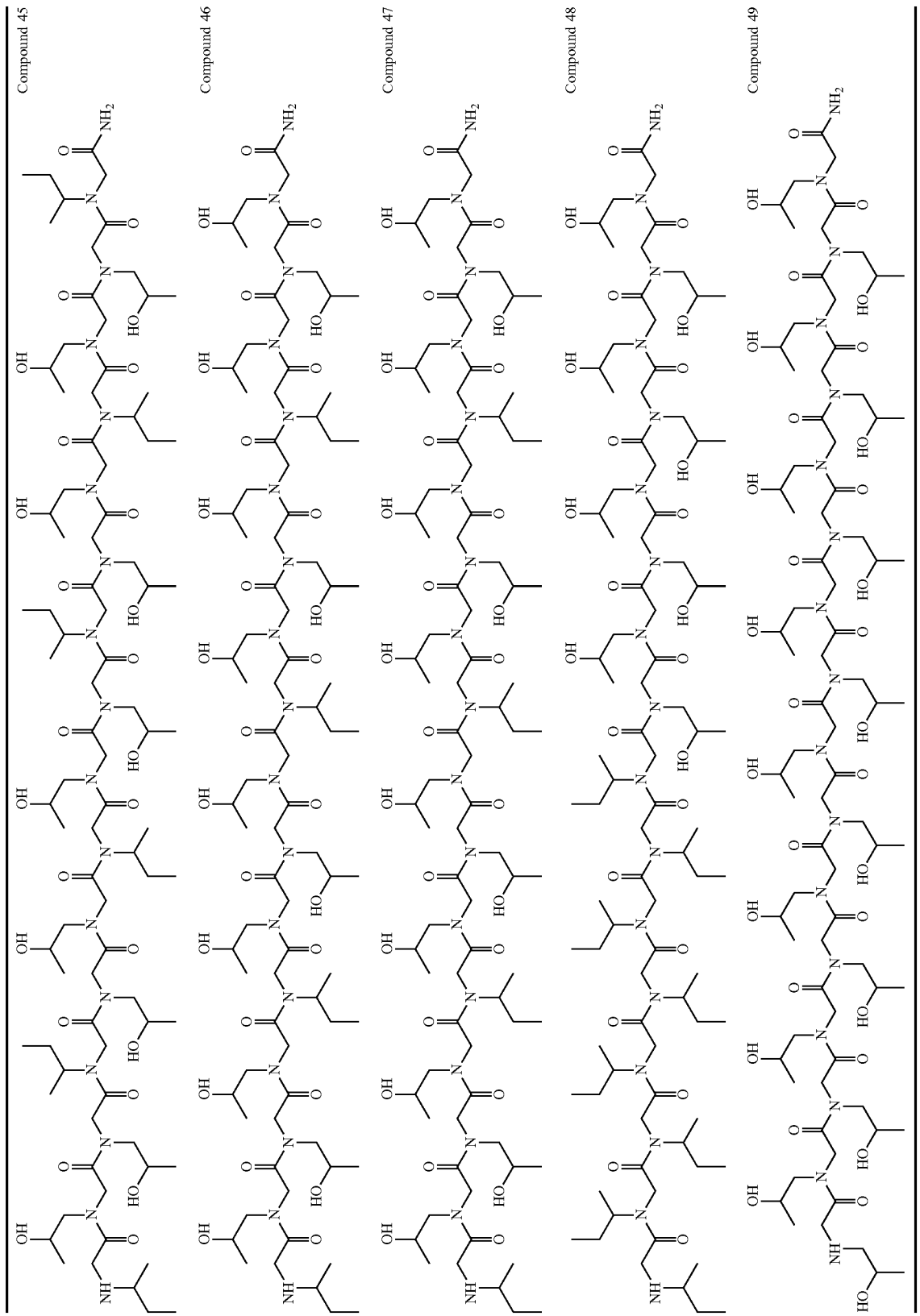

TABLE 9
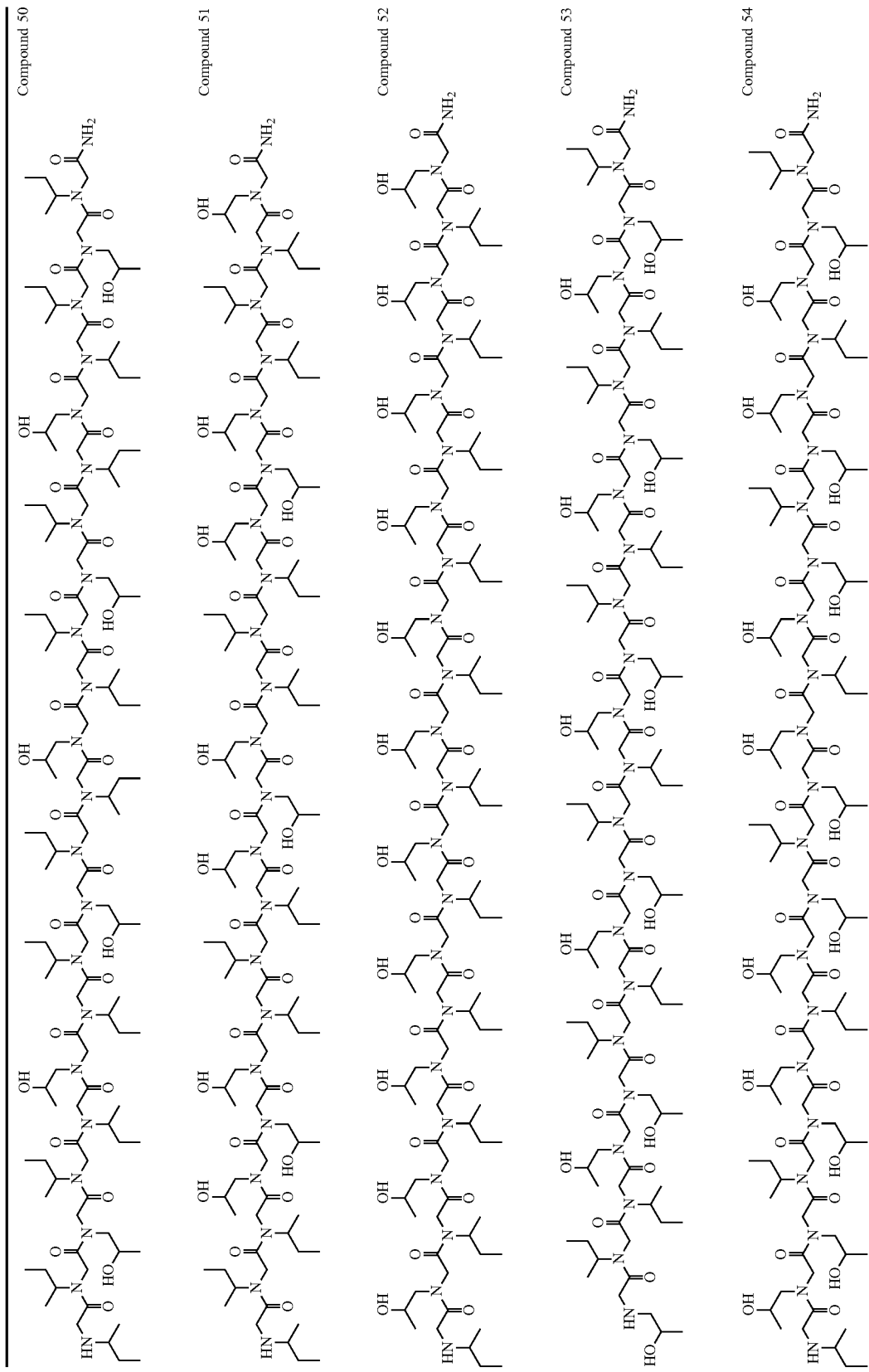

TABLE 9-continued
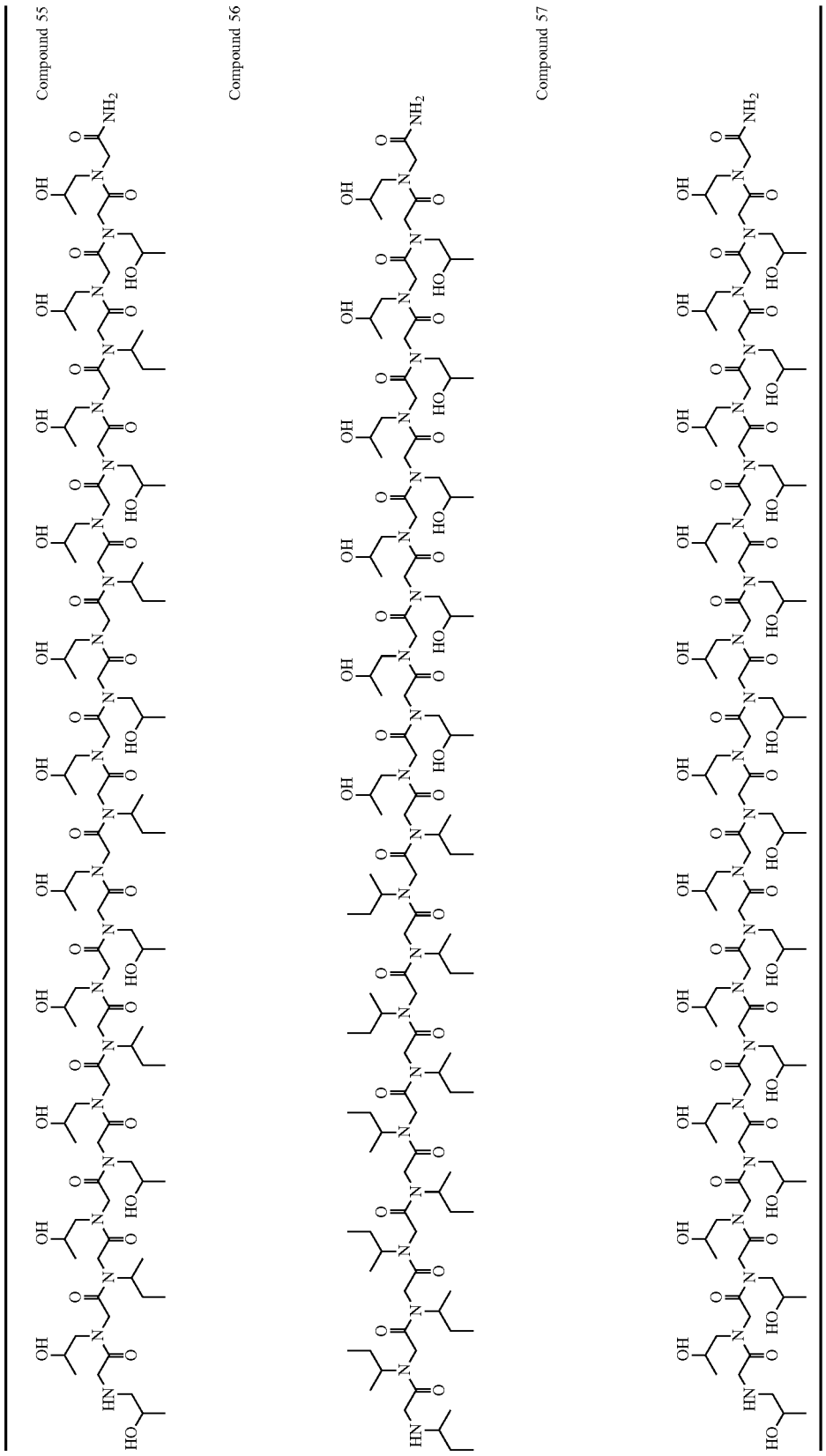

In some embodiments, the sequence length of the peptoid polymer, n, is 10, and the peptoid polymer comprises: 10 Nsb monomers, 1 Nhp monomer and 9 Nsb monomers, 2 Nhp monomers and 8 Nsb monomers, 3 Nhp monomers and 7 Nsb monomers, 4 Nhp monomers and 6 Nsb monomers, 5 Nhp monomers and 5 Nsb monomers, 6 Nhp monomers and 4 Nsb monomers, 7 Nhp monomers and 3 Nsb monomers, 8 Nhp monomers and 2 Nsb monomers, 9 Nhp monomers and 1 Nsb monomer, or 10 Nhp monomers.

In some embodiments, the peptoid polymer has the sequence Nhp-Nhp-Nhp-Nhp-Nhp-Nhp-Nhp-Nhp-Nhp-Nhp (SEQ ID NO:2), wherein X is H or $C_{1-8}$ acyl and Y is —OH or —NH$_2$ or $C_{1-8}$ alkyl. In some embodiments, the peptoid polymer has the sequence Nsb-Nsb-Nhp-Nsb-Nsb-Nhp-Nsb-Nsb-Nhp-Nsb (SEQ ID NO:1), wherein X is H or $C_{1-8}$ acyl and Y is —OH or —NH$_2$ or $C_{1-8}$ alkyl. In some embodiments, the peptoid polymer has the sequence Nsb-Nhp-Nhp-Nhp-Nsb-Nhp-Nhp-Nhp-Nsb-Nhp (SEQ ID NO:7), wherein X is H or $C_{1-8}$ acyl and Y is —OH or —NH$_2$ or $C_{1-8}$ alkyl. In some embodiments, the peptoid polymer has the sequence Nsb-Nsb-Nhp-Nhp-Nsb-Nsb-Nhp-Nhp-Nsb-Nsb (SEQ ID NO:8), wherein X is H or $C_{1-8}$ acyl and Y is —OH or —NH$_2$ or $C_{1-8}$ alkyl. In some embodiments, the peptoid polymer has the sequence Nsb-Nhp-Nhp-Nhp-Nhp-Nhp-Nsb-Nhp-Nhp-Nhp (SEQ ID NO:9), wherein X is H or $C_{1-8}$ acyl and Y is —OH or —NH$_2$ or $C_{1-8}$ alkyl. In some embodiments, Y is a secondary amine or a tertiary amine.

In some embodiments, the sequence length of the peptoid polymer, n, is 10, and the peptoid polymer comprises: 10 Nine monomers, 1 Nhp monomer and 9 Nine monomers, 2 Nhp monomers and 8 Nine monomers, 3 Nhp monomers and 7 Nine monomers, 4 Nhp monomers and 6 Nine monomers, 5 Nhp monomers and 5 Nine monomers, 6 Nhp monomers and 4 Nine monomers, 7 Nhp monomers and 3 Nine monomers, and 8 Nhp monomers and 2 Nine monomers, or 9 Nhp monomers and 1 Nine monomer.

In some embodiments, the sequence length of the peptoid polymer, n, is 10, and the peptoid polymer comprises: 1 Nhe monomers and 9 Nsb monomers, 2 Nhe monomers and 8 Nsb monomers, 3 Nhe monomers and 7 Nsb monomers, 4 Nhe monomers and 6 Nsb monomers, 5 Nhe monomers and 5 Nsb monomers, 6 Nhe monomers and 4 Nsb monomers, 7 Nhe monomers and 3 Nsb monomers, 8 Nhe monomers and 2 Nsb monomers, 9 Nhe monomers and 1 Nsb monomers, or 10 Nhe monomers.

In some embodiments, the sequence length of the peptoid polymer, n, is 10, and the peptoid polymer comprises: 10 Nbu monomers, 1 Nhp monomer and 9 Nbu monomers, 2 Nhp monomers and 8 Nbu monomers, 3 Nhp monomers and 7 Nbu monomers, 4 Nhp monomers and 6 Nbu monomers, 5 Nhp monomers and 5 Nbu monomers 6 Nhp monomers and 4 Nbu monomers, 7 Nhp monomers and 3 Nbu monomers, 8 Nhp monomers and 2 Nbu monomers, or 9 Nhp monomers and 1 Nbu monomer.

In some embodiments, the sequence length of the peptoid polymer, n, is 10, and the peptoid polymer comprises: 10 Nib monomers, 1 Nhp monomer and 9 Nib monomers, 2 Nhp monomers and 8 Nib monomers, 3 Nhp monomers and 7 Nib monomers, 4 Nhp monomers and 6 Nib monomers, 5 Nhp monomers and 5 Nib monomers, 6 Nhp monomers and 4 Nib monomers, 7 Nhp monomers and 3 Nib monomers, 8 Nhp monomers and 2 Nib monomers, or 9 Nhp monomers and 1 Nib monomer.

In some embodiments, the sequence length of the peptoid polymer, n, is 10, and the peptoid polymer comprises: 10 Npr monomers, 1 Nhp monomer and 9 Npr monomers, 2 Nhp monomers and 8 Npr monomers, 3 Nhp monomers and 7 Npr monomers, 4 Nhp monomers and 6 Npr monomers, 5 Nhp monomers and 5 Npr monomers, 6 Nhp monomers and 4 Npr monomers, 7 Nhp monomers and 3 Npr monomers, 8 Nhp monomers and 2 Npr monomers, or 9 Nhp monomers and 1 Npr monomer.

In some embodiments, the sequence length of the peptoid polymer, n, is 10, and the peptoid polymer comprises: 10 Nip monomers, 1 Nhp monomer and 9 Nip monomers, 2 Nhp monomers and 8 Nip monomers, 3 Nhp monomers and 7 Nip monomers, 4 Nhp monomers and 6 Nip monomers, 5 Nhp monomers and 5 Nip monomers, 6 Nhp monomers and 4 Nip monomers, 7 Nhp monomers and 3 Nip monomers, 8 Nhp monomers and 2 Nip monomers, or 9 Nhp monomers and 1 Nip monomer.

In some embodiments, the sequence length of the peptoid polymer, n, is 14, and the peptoid polymer comprises: 6 Nhp monomers and 8 Nsb monomers, 7 Nhp monomers and 7 Nsb monomers, 8 Nhp monomers and 6 Nsb monomers, 10 Nhp monomers and 4 Nsb monomers, or 14 Nhp monomers.

In some embodiments, the sequence length of the peptoid polymer, n, is 14, and the peptoid polymer comprises: 6 Nhp monomers and 8 Nib monomers, 7 Nhp monomers and 7 Nib monomers, 8 Nhp monomers and 6 Nib monomers, 10 Nhp monomers and 4 Nib monomers, or 14 Nhp monomers.

In some embodiments, the sequence length of the peptoid polymer, n, is 16, and the peptoid polymer comprises: 5 Nhp monomers and 11 Nsb monomers, 7 Nhp monomers and 9 Nsb monomers, 8 Nhp monomers and 8 Nsb monomers, 10 Nhp monomers and 6 Nsb monomers, 12 Nhp monomers and 4 Nsb monomers, or 16 Nhp monomers.

In some embodiments, the sequence length of the peptoid polymer, n, is 22, and the peptoid polymer comprises: 7 Nhp monomers and 15 Nsb monomers, 10 Nhp monomers and 12 Nsb monomers, 11 Nhp monomers and 11 Nsb monomers, 14 Nhp monomers and 8 Nsb monomers, 17 Nhp monomers and 5 Nsb monomers, or 22 Nhp monomers.

In some embodiments, the peptoid polymer described herein forms a helical structure. In some embodiments, the helical structure adopts a structure analogous to a polyproline helix. In certain instances, the peptoid polymer forms a polyproline I helix. In certain other instances, the peptoid polymer forms a polyproline II helix. In some embodiments, a helical structure is adopted when the peptoid polymer comprises at least one N-Aryl side chain. In some embodiments, the N-Aryl side chain is a Nep monomer.

In some embodiments, the peptoid polymer reduces or inhibits ice crystal formation at a temperature within about 0° C. to about −20° C. In other embodiments, the peptoid polymer reduces or inhibits ice crystal formation at a temperature within about −20° C. to about −40° C. In certain embodiments, the peptoid polymer reduces or inhibits ice crystal formation at about −20° C. In certain other embodiments, the peptoid polymer reduces or inhibits ice crystal formation at a temperature within about −40° C. to about −200° C. (e.g., about −196° C.).

In some embodiments, the peptoid polymer reduces or inhibits ice crystal formation at a temperature within about 0° C. to about −200° C., within about −10° C. to about −190° C., within about −20° C. to about −180° C., within about −30° C. to about −170° C., within about −40° C. to about −160° C., within about −50° C. to about −150° C., within about −60° C. to about −140° C., within about −70° C. to about −140° C., within about −80° C. to about −130° C., within about −90° C. to about −120° C., or within about −100° C. to about −110° C.

In other embodiments, the peptoid polymer reduces or inhibits ice crystal formation at or about −10° C., at or about −15° C., at or about −25° C., at or about −30° C., at or about −35° C., at or about −40° C., at or about −45° C., at or about −50° C., at or about −55° C., at or about −60° C., at or about −65° C., at or about −70° C., at or about −75° C., at or about −80° C., at or about −85° C., at or about −90° C., at or about −95° C., at or about −100° C., at or about −105° C., at or about −110° C., at or about −115° C., at or about −120° C., at or about −125° C., at or about −130° C., at or about −135° C., at or about −140° C., at or about −145° C., at or about −150° C., at or about −155° C., at or about −160° C., at or about −165° C., at or about −170° C., at or about −175° C., at or about −180° C., at or about −185° C., at or about −190° C., at or about −195° C., at or about −196° C., or at or about −200° C.

In some embodiments, the concentration of the peptoid polymer (e.g., present in a composition, formulation, or product such as a cryoprotectant solution, antifreeze solution, frozen food product, or cosmetic care product) is between about 100 nM and about 100 mM. In certain embodiments, the concentration of the peptoid polymer (e.g., present in a composition, formulation, or product such as a cryoprotectant solution, antifreeze solution, frozen food product, or cosmetic care product) is between about 100 nM and about 250 nM, between about 250 nM and about 500 nM, between about 500 nM and about 750 nM, between about 750 nM and about 1 µM, between about 1 µM and about 5 µM, between about 5 µM and about 25 µM, between about 25 µM and about 50 µM, between about 50 µM and about 100 µM, between about 100 µM and about 250 µM, between about 250 µM and about 500 µM, between about 500 µM and about 750 µM, between about 750 µM and about 1 mM, between about 1 mM and about 10 mM, between about 10 mM and about 50 mM, or between about 50 mM and about 100 mM. In other embodiments, the concentration of the peptoid polymer (e.g., present in a composition, formulation, or product such as a cryoprotectant solution, antifreeze solution, frozen food product, or cosmetic care product) is about 100 nM, about 1 µM, about 10 µM, about 100 µM, about 1 mM, about 10 mM, or about 100 mM. In particular embodiments, the concentration of the peptoid polymer is about 1, 2, 3, 4, 5, 6, 7, 8, 9, or 10 mM.

B. Peptoid-Peptide Hybrids

In another aspect, the invention provides a peptoid-peptide hybrid. In some embodiments, the peptoid-peptide hybrid comprises a peptoid polymer described herein and one or more amino acids. The amino acids can be naturally-occurring amino acids or variants thereof. In some embodiments, the peptoid-peptide hybrid comprises between about 1 and 10 amino acids (e.g., about 1, 2, 3, 4, 5, 6, 7, 8, 9, or 10 amino acids). In other embodiments, the peptoid-peptide hybrid comprises between about 10 and 100 amino acids (e.g., about 10, 15, 20, 25, 30, 35, 40, 45, 50, 55, 60, 65, 70, 75, 80, 85, 90, 95, or 100 amino acids). In some embodiments, the peptoid-peptide hybrid comprises more than about 100 amino acids. In other embodiments, the peptoid-peptide hybrid comprises between 2 and 50 peptoid monomers (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 44, 45, 46, 47, 48, 49, or 50 peptoid monomers) and at least between about 1 and 100 amino acids (e.g., at least about 1, 2, 3, 4, 5, 6, 7, 8, 9, 10, 15, 20, 25, 30, 35, 40, 45, 50, 55, 60, 65, 70, 75, 80, 85, 90, 95, or 100 amino acids).

The amino acids can be located at any position within the polymer, including at the N- and C-terminal ends and/or in between any of the peptoid monomers. In instances where the peptoid-peptide hybrid comprises two or more amino acids, the amino acids may all be contiguous, or only a portion of them may be contiguous. Alternatively, all of the amino acids may be separated by one or more peptoid monomers.

In some embodiments, the amino acids are D-amino acids. In other embodiments, the amino acids are L-amino acids. In some other embodiments, the peptoid-peptide hybrid comprises a combination of D- and L-amino acids. In some embodiments, the one or more amino acids are selected from the group consisting of alanine, cysteine, aspartic acid, glutamic acid, phenylalanine, glycine, histidine, isoleucine, arginine, lysine, leucine, methionine, asparagine, proline, glutamine, serine, threonine, valine, tryptophan, tyrosine, and a combination thereof. In some instances, the one or more amino acids are selected from the group consisting of isoleucine, threonine, alanine, and a combination thereof.

In some embodiments, one or more Nsb peptoid monomers in a peptoid polymer are replaced with one or more isoleucine amino acid residues to create a peptoid-peptide hybrid. The one or more isoleucine amino acids can be D-amino acids, L-amino acids, or a combination thereof. In other embodiments, one or more Nhp peptoid monomers in a peptoid polymer are replaced with one or more threonine amino acid residues to create a peptoid-peptide hybrid. The one or more threonine amino acids can be D-amino acids, L-amino acids, or a combination thereof. In some other embodiments, one or more Nine peptoid monomers in a peptoid polymer are replaced with one or more alanine amino acid residues to create a peptoid-peptide hybrid. The one or more alanine amino acids can be D-amino acids, L-amino acids, or a combination thereof.

In some embodiments, the peptoid-peptide hybrid comprises the sequence:

(SEQ ID NO: 3)
Nep-Nep-Xaa-Xaa-Xaa-Xaa-Nep-Nep-Nep-Nep-Nme-Nme;

wherein the Xaa amino acid residues are independently selected amino acids such as D-amino acids, L-amino acids, or a combination thereof. As a non-limiting example, all instances of Xaa are Arg, Ala, Val, and/or Ser amino acid residues.

In other embodiments, the peptoid-peptide hybrid comprises the sequence:

(SEQ ID NO: 4)
Nme-Nme-Xaa-Nme-Nme-Nme-Nme-Nhp-Nhp-Nsb-Xaa-Nme-

Nme-Xaa-Nme-Nme-Nme;

wherein the Xaa amino acid residues are independently selected amino acids such as D-amino acids, L-amino acids, or a combination thereof. As a non-limiting example, all instances of Xaa are Arg, Ala, Val, and/or Ile amino acid residues.

In yet other embodiments, the peptoid-peptide hybrid comprises the sequence:

(SEQ ID NO: 5)
Nme-Nme-Xaa-Nme-Nme-Nme-Nme-Nme-Nme-Nme-Xaa-Xaa;

wherein the Xaa amino acid residues are independently selected amino acids such as D-amino acids, L-amino acids, or a combination thereof. As a non-limiting example, all instances of Xaa are Arg, Ala, Val, and/or Leu amino acid residues.

In some embodiments, the peptoid-peptide hybrid comprises the sequence:

(SEQ ID NO: 6)
Arg-Nsb-Nsb-Nhp-Nhp-Nsb-Nsb-Nhp-Nhp-Nsb-Nsb;

wherein the Arg amino acid residue is a D-amino acid or an L-amino acid. In some embodiments, the peptoid-peptide hybrid comprises the structure set forth in Table 10.

TABLE 10

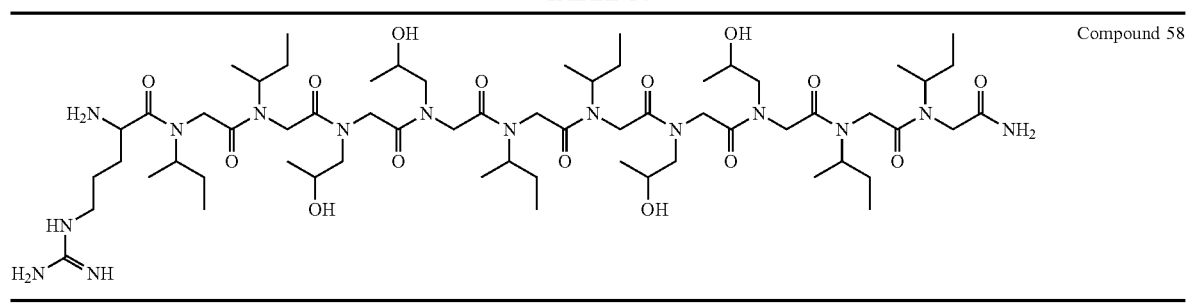

Compound 58

C. Methods of Synthesis

In another aspect, the invention herein provides a method of synthesizing a peptoid polymer or a peptoid-peptide hybrid. The peptoid polymers and peptoid-peptide hybrids of the invention can be prepared from readily available starting materials using the general methods and procedures described herein. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

The peptoid polymers and peptoid-peptide hybrids of the invention may be prepared from known or commercially available starting materials and reagents by one skilled in the art of organic synthesis. Solvents and reagents are purchased from commercial sources and used without further purification.

In some embodiments, the submonomer approach (FIG. 1) is used for peptoid synthesis, where each N-substituted glycine monomer is assembled from two readily available "submonomers." The synthesis of oligomeric peptoids is based on the robust chemistry of standard solid-phase methods, analogous to peptide synthesis. Each cycle of monomer addition consists of two steps, an acylation step and a nucleophilic displacement step. In some embodiments, solid-phase assembly eliminates the need for N-protected monomers because there are no reactive side chain functionalities that need to be protected. One of skill in the art will recognize there are many solid-phase synthesis methods, including automated, robotic synthesizers. In some embodiments, the synthesizer used is the Symphony© X Multiplex Peptide Synthesizer made by Protein Technologies, Inc. In some embodiments, the synthesizer used is the Overture Peptide Synthesizer made by Protein Technologies, Inc. In other embodiments, the peptoids are synthesized manually using traditional organic chemistry methods known in the art. By providing the appropriate amino acids in place of peptoid monomers at the appropriate times during synthesis, the same techniques or techniques similar to those described above can be applied to the synthesis of peptoid-peptide oligomers.

As a non-limiting example, peptoid polymers can be synthesized on 100 mg of Rink amide resin (NovaBiochem; 0.49 mmol/g). Rink amide resin (100 mg) can be washed twice in 1.5 mL of DCM, followed by swelling in 1.5 mL of DMF. The swelling step can be performed twice. The Fmoc protecting group can be removed from the resin by addition of 20% piperidine/DMF. The mixture can be agitated for 10 minutes, drained, and the piperidine treatment repeated, followed by extensive washes with DMF (five times with 1.5 mL). The first monomer can be added manually by reacting 37 mg of bromoacetic acid (0.27 mmol; Sigma-Aldrich) and 189 μL of DIEA (1.08 mmol; Chem Impex International) in 2 mL of DCM on a shaker platform for 30 minutes at room temperature, followed by extensive washes with DCM (five times with 2 mL) and DMF (five times with 2 mL). Bromoacylated resin can be incubated with 2 mL of 1 M amine submonomer in DMF on a shaker platform for 30 minutes at room temperature, followed by extensive washes with DMF (five times with 2 mL). After initial manual loading of bromoacetic acid, the first submonomer displacement step and all subsequent bromo acetylation and amine displacement steps can be performed by a robotic synthesizer until the desired oligomer length is obtained. The automated bromoacetylation step can be performed by adding 1660 μL of 1.2 M bromoacetic acid in DMF and 400 μL of DIC (Chem Impex International). The mixture can be agitated for 20 min, drained, and washed with DMF (three times with 2 mL). Next, 2 mL of a 1 M solution of submonomer (2 mmol) in DMF can be added to introduce the side chain by nucleophilic displacement of bromide. The mixture can be agitated for 20 min, drained, washed with DMF (three times with 2 mL) and washed with DCM (three times with 2 mL). The peptoid-resin can be cleaved in 2 mL of 20% HFIP (Alfa Aesar) in DCM (v/v) at room temperature. The cleavage can be conducted in a glass tube with constant agitation for 30 minutes. HFIP/DCM can be evaporated under a stream of nitrogen gas. The final product can be dissolved in 5 mL of 50% ACN in HPLC grade $H_2O$ and filtered with a 0.5 pm stainless steel fritted syringe tip filter (Upchurch Scientific). Peptoid oligomers can be analyzed on a $C_{18}$ reversed-phase analytical HPLC column at room temperature (Peeke Scientific, 5 pm, 120 Å., 2.0×50 mm) using a Beckman Coulter System Gold instrument. A linear gradient of 5-95% acetonitrile/water (0.1% TFA, Acros Organics) over 20 min can be used with a flow rate of 0.7 mL/min. In order to remove any traces of HFIP in the sample solution, linear precursors dissolved in 50% ACN/$H_2O$ can be freeze-dried overnight.

Peptoid polymers and peptoid-peptide hybrids can be analyzed by electrospray ionization (ESI) mass spectrometry. Generally, 0.5-2 mL of 1-5 μM of peptoid polymer or peptoid-peptide hybrid to be analyzed is prepared in a 50% deionized $H_2O$/50% HPLC grade ACN with 1% of an organic acid such as trifluoroacetic acid. Prepared samples are ionized by bombardment with electrons causing the molecules to break into charged fragments. The ions are then separated according to their mass-to-charge ratio by accelerating the fragments and exposing them to an electrical or magnetic field. The ions are detected by a mechanism capable of detecting charged particles, such as an electron multiplier. Peptoids and peptoid-peptide hybrids are identified by correlating masses to the identified masses or through a characteristic fragmentation pattern.

D. Methods of Use

In some aspects, the present invention provides a cryoprotectant solution. In some embodiments, the cryoprotectant solution comprises a peptoid polymer described herein, a peptoid-peptide hybrid described herein, or a combination thereof. In other embodiments, the cryoprotectant solution further comprises a compound selected from the group consisting of an ionic species, a penetrating cryoprotectant, a non-penetrating cryoprotectant, an antioxidant, a cell membrane stabilizing compound, an aquaporin or other channel forming compound, an alcohol, a sugar, a sugar derivative, a nonionic surfactant, a protein, dimethyl sulfoxide (DMSO), polyethylene glycol (PEG), Ficoll®, polyvinylpyrrolidone, polyvinyl alcohol, hyaluronan, formamide, a natural or synthetic hydrogel, and a combination thereof. In particular embodiments, the penetrating cryoprotectant penetrates the cell membrane and reduces the intracellular water concentration, thereby reducing the amount of ice formed at any temperature. In other particular embodiments, the non-penetrating cryoprotectant induces changes in colloidal osmotic pressure and modifies cell membrane associations with extracellular water by induced ionic interaction.

In some instances, the cryoprotectant solution further comprises an alcohol that is selected from the group consisting of propylene glycol, ethylene glycol, glycerol, methanol, butylene glycol, adonitol, ethanol, trimethylene glycol, diethylene glycol, polyethylene oxide, erythritol, sorbitol, xythyritol, polypropylene glycol, 2-methyl-2,4-pentanediol (MPD), mannitol, inositol, dithioritol, 1,2-propanediol, and a combination thereof.

In other instances, the cryoprotectant solution further comprises a sugar that is selected from the group consisting of a monosaccharide, a disaccharide, a polysaccharide, and a combination thereof. In particular instances, the sugar is selected from the group consisting of glucose, 3-O-Methyl-D-glucopyranose, galactose, arabinose, fructose, xylose, mannose, sucrose, trehalose, lactose, maltose, raffinose, dextran, and a combination thereof.

In other instances, the cryoprotectant solution further comprises PEG or a plurality of different PEG compounds. In some other instances, at least one of the PEG compounds has an average molecular weight less than about 1,000 g/mol (e.g., less than about 1,000 950, 900, 850, 800, 750, 700, 650, 600, 550, 500, 450, 400, 350, 300, 250, 200, 150, or 100 g/mol). In particular instances, a least one of the PEG compounds has an average molecular weight between about 200 and 400 g/mol (e.g., about 200, 210, 220, 230, 240, 250, 260, 270, 280, 290, 300, 310, 320, 330, 340, 350, 360, 370, 380, 390, or 400 g/mol). In some instances, the cryoprotectant solution comprises PEG or a plurality of PEG compounds selected from the group consisting of PEG 200, PEG 300, PEG 400, and a combination thereof.

In other instances, the cryoprotectant solution further comprises a protein that is selected from the group consisting of egg albumin, bovine serum albumin, human serum albumin, gelatin, and a combination thereof. In still other instances, the cryoprotectant solution further comprises a natural or synthetic hydrogel, wherein the natural or synthetic hydrogel comprises chitosan, hyaluronic acid, or a combination thereof.

Non-limiting examples of various properties of the cryoprotectant solution such as effective concentration, viscosity, water solubility, and/or membrane permeability can be assessed using a model cell or tissue including, but not limited to, stem cells, liver tissue or hepatocytes, kidney, intestine, heart, pancreas, bone marrow, organoids, and other biological tissues for cryopreservation.

In some embodiments, the cryoprotectant solution reduces or inhibits ice crystal formation at a temperature within about 0° C. to about −20° C. In other embodiments, the cryoprotectant solution reduces or inhibits ice crystal formation at a temperature within about −20° C. to about −40° C. In certain embodiments, the cryoprotectant solution reduces or inhibits ice crystal formation at about −20° C. In certain other embodiments, the cryoprotectant solution reduces or inhibits ice crystal formation at a temperature within about −40° C. to about −200° C. (e.g., about −196° C.).

In some embodiments, the cryoprotectant solution reduces or inhibits ice crystal formation at a temperature within about 0° C. to about −200° C., within about −10° C. to about −190° C., within about −20° C. to about −180° C., within about −30° C. to about −170° C., within about −40° C. to about −160° C., within about −50° C. to about −150° C., within about −60° C. to about −140° C., within about −70° C. to about −140° C., within about −80° C. to about −130° C., within about −90° C. to about −120° C., or within about −100° C. to about −110° C.

In other embodiments, the cryoprotectant solution reduces or inhibits ice crystal formation at or about −10° C., at or about −15° C., at or about −25° C., at or about −30° C., at or about −35° C., at or about −40° C., at or about −45° C., at or about −50° C., at or about −55° C., at or about −60° C., at or about −65° C., at or about −70° C., at or about −75° C., at or about −80° C., at or about −85° C., at or about −90° C., at or about −95° C., at or about −100° C., at or about −105° C., at or about −110° C., at or about −115° C., at or about −120° C., at or about −125° C., at or about −130° C., at or about −135° C., at or about −140° C., at or about −145° C., at or about −150° C., at or about −155° C., at or about −160° C., at or about −165° C., at or about −170° C., at or about −175° C., at or about −180° C., at or about −185° C., at or about −190° C., at or about −195° C., at or about −196° C., or at or about −200° C.

In some embodiments, the concentration of the peptoid polymer and/or peptoid-peptide hybrid in the cryoprotectant solution is between about 100 nM and about 100 mM. In some embodiments, the concentration of peptoid polymer and/or peptoid-peptide hybrid in the cryoprotectant solution is between about 100 nM and about 250 nM, between about 250 nM and about 500 nM, between about 500 nM and about 750 nM, between about 750 nM and about 1 µM, between about 1 µM and about 5 µM, between about 5 µM and about 25 µM, between about 25 µM and about 50 µM, between about 50 µM and about 100 µM, between about 100 µM and about 250 µM, between about 250 µM and about 500 µM, between about 500 µM and about 750 µM, between about 750 µM and about 1 mM, between about 1 mM and about 10 mM, between about 10 mM and about 50 mM, or between about 50 mM and about 100 mM. In some embodiments, the concentration of the peptoid polymer and/or peptoid-peptide hybrid in the cryoprotectant solution is about 100 nM, about 1 µM, about 10 µM, about 100 µM, about 1 mM, about 10 mM, or about 100 mM. In particular embodiments, the concentration of the peptoid polymer and/or peptoid-peptide hybrid in the cryoprotectant solution is about 1, 2, 3, 4, 5, 6, 7, 8, 9, or 10 mM.

In other aspects, provided herein is a method for preserving a biological sample. In particular embodiments, the biological sample possesses cellular composition. In some embodiments, the biological sample is a tissue. In other embodiments, the biological sample is an organ. In still other embodiments, the biological sample is a cell. In particular embodiments, the biological sample comprises one or more tissues, organs, or cells, or a combination thereof. In some embodiments, the method comprises contacting the biological sample with a peptoid polymer described herein, a peptoid-peptide hybrid described herein, a cryoprotectant solution described herein, or a combination thereof. In some instances, when a combination of compositions or solutions is used, contacting the biological sample with the compositions or solutions can be accomplished in multiple steps. As a non-limiting example, a biological sample can first be contacted with a peptoid polymer described herein, and then at a later point the biological sample can be contacted with a cryoprotection solution described herein.

In particular instances, the tissue is a bioengineered tissue. In some instances, the biological sample is selected from the group consisting of heart, liver, lung, kidney, pancreas, intestine, thymus, cornea, nerve cells, blood platelets, sperm cells, oocytes, embryonic cells, stem cells, bone cells, and a combination thereof.

Cryoprotection of biological samples is useful for any number of purposes. Non-limiting examples include organoid preservation, stem cell preservation (e.g., hematopoietic stem cells, embryonic stem (ES) cells, pluripotent stem cells (PSCs), and induced pluripotent stem cells (iPSCs)), preservation of adult cells and cell lines (e.g., lymphocytes, granulocytes, immune system cells, bone cells), preservation of embryos, sperm, and oocytes, tissue preservation, and organ preservation. Preservation of tissues, organs, and other biological samples and structures is especially useful, for example, in the field of organ transplantation. Other useful applications of the present invention to biological sample cryoprotection will readily be known to one of skill in the art.

In yet other aspects, provided herein is a method for preserving one or more biological macromolecules. Said biological macromolecules can be naturally or unnaturally occurring. Non-limiting examples of biological macromolecules that are suitable for cryoprotection by compositions and methods of the present invention include nucleic acids (e.g., DNA, RNA), amino acids, proteins, peptides, lipids, and composite structures (e.g., liposomes). In some embodiments, the method comprises contacting the biological macromolecule with a peptoid polymer described herein, a peptoid-peptide hybrid described herein, a cryoprotectant solution described herein, or a combination thereof. In some instances, the biological macromolecule is an isolated protein. In particular instances, the isolated protein is a protease protein. In some instances, when a combination of compositions or solutions is used, contacting the one or more biological macromolecules with the compositions or solutions can be accomplished in multiple steps. As a non-limiting example, the one or more biological macromolecules can first be contacted with a peptoid polymer described herein, and then at a later point the biological sample can be contacted with a cryoprotection solution described herein.

Cryoprotection of biological macromolecules using compositions and methods of the present invention is useful for any number of purposes. Non-limiting examples of such purposes include the preservation of DNA (e.g., genomic DNA) and RNA samples, the preservation of stem cell growth factors, and the preservation of antibodies. Other useful purposes and applications appropriate for compositions and methods of the present invention will be readily known by one of skill in the art.

In particular embodiments, the isolated protein has been crystallized. Crystal cryoprotection has become an essential tool in the repertoire of crystallographic methods for studying biological macromolecules (e.g., proteins and peptides). In many cases, cryoprotection and subsequent data collection at cryogenic temperature are essential for obtaining a complete data set by overcoming the problem of radiation damage from the x-ray beam line. Moreover, cryomethods allow crystallographers to work with small crystals, and such methods have become an ideal method to perform long term storage of the crystals without losing diffraction quality. Cryoprotectants provide a means to protect macromolecular crystals from the damaging effects of ice formation during the cryocooling process. Cryoprotection usually involves immersing the crystal in a solution that forms an amorphous glass (i.e., vitrification) while being flash cooled in liquid nitrogen. The ideal cryoprotectants for crystallography should be hypereffective (i.e., the cryoprotectants achieve an effective result at a low concentration). Currently available cryoprotectants are not hypereffective. Therefore, if the cryoprotectant concentration is too low, crystalline ice will form during the experiment which leads to background interference. If the cryoprotectant concentration is too high, the immediate melting down of the crystal structure can result from beam energy, resulting in low quality data affecting subsequent structure analysis. For example, current state of the art cryoprotectant solutions used in x-ray crystallography applications require the use of 20% ethylene glycol to prevent ice crystal formation at crystalized protein storage temperatures. During x-ray data collection, the ethylene glycol heats and dissolves the crystals preventing further data collection. For additional information, see, e.g., Garman et al. *J. Appl. Cryst.* 30:211 (1997).

In some embodiments, the peptoid polymer, peptoid-peptide hybrid, or cryoprotectant solution described herein, or a combination thereof, decreases crystal dissolving during x-ray data collection. In some embodiments, the peptoid polymer, peptoid-peptide hybrid, cryoprotectant solution described herein, or a combination thereof, lowers background scattering.

Biological samples and macromolecules that are suitable for cryoprotection according to the compositions and methods of the present invention can come from any biological kingdom (e.g., Animalia (including but not limited to humans and livestock animals), Plantae, Fungi (including but not limited to mushrooms), Protista, Archaea/Archaeabacteria, and Bacteria/Eubacteria).

In another aspect, the present invention provides a cosmetic care product. In some embodiments, the cosmetic care product comprises a peptoid polymer described herein, a peptoid-peptide hybrid described herein, a cryoprotection solution described herein, or a combination thereof. In some embodiments, the cosmetic care product is a skin care product. In some embodiments the skin care product is topically applied. Typical formulations for topical products include creams, serums, ointments, sprays, lotions, and patches.

In another aspect, the present invention provides an antifreeze product such as a deicing or ice inhibiting product. In some embodiments, the antifreeze product comprises a peptoid polymer described herein, a peptoid-peptide hybrid described herein, a cryoprotection solution described herein, or a combination thereof. In some embodiments, the antifreeze product is used to prevent, inhibit, or delay the formation of ice on objects including, but not limited to, general mechanical and electrical equipment. In some embodiments, the antifreeze product prevents, inhibits, or delays the formation of ice on aircraft or parts thereof, drones, automobiles or parts thereof, including car engines, gear systems, brake systems, windows, sprinkler systems, gas pipelines, or electrical cables, including powerlines. In other instances, the antifreeze product acts as a kinetic hydrate inhibitor. In some embodiments the antifreeze product further comprises ethylene glycol, methanol, propylene glycol, glycerol, or combinations thereof.

In another aspect, the present invention provides a frozen food product. In some embodiments the frozen food product comprises a peptoid polymer described herein, a peptoid-peptide hybrid described herein, a cryoprotection solution described herein, or a combination thereof. In some embodiments, the frozen food product is selected from the group consisting of ice cream, yogurt, seafood, fruit, and meat products. In some embodiments the frozen food product further comprises propylene glycol.

E. Cryopreservation Protocols

The compositions and methods described herein are suitable for use in any number of cryopreservation protocols. As a non-limiting example, compositions and methods of the present invention are useful for cryopreservation during supercooling to high sub-zero temperatures (e.g., 0° C. to −20° C.). In the field of organ transplantation, organs are typically cooled on ice (e.g., to 0-4° C.), which limits the transplantation window to about ten hours. By using ex vivo machine perfusion with cryoprotectants containing standard small molecule CPAs, it has been possible to preserve organs for up to 96 hours at a temperature of −6° C. While it is desirable to further reduce the cryopreservation temperature below −6° C., which would extend the possible cryopreservation time, it has not been possible to do so because the high concentrations of standard CPAs necessary to further reduce the temperature result in irreversible organ damage owing to CPA-related toxicity. For more information, see, e.g., Uygun K, et. al. *Nat. Protoc.* 10(3):484-94 (2015). Employing ex vivo perfusion methods or otherwise contacting biological samples (e.g., organs and tissues) or macromolecules with peptoid polymers, peptoid-peptide hybrids, and/or cryoprotectant solutions described herein is useful for supercooling to high sub-zero temperatures, allowing cryopreservation for longer periods of time and at lower temperatures than is currently feasible. Other suitable applications of the present invention to high sub-zero temperature supercooling will readily be known to one of skill in the art.

As another non-limiting example, compositions and methods of the present invention are useful for cryopreservation during freezing protocols (e.g., −20° C. to −196° C.). Freezing protocols are typically performed at a controlled rate (sometimes referred to as slow freezing) during at least part of the temperature reduction. For example, a biological sample or macromolecule can be contacted with a peptoid polymer, peptoid-peptide hybrid, and/or cryoprotectant solution described herein, and the temperature can be reduced at a controlled rate (e.g., lowered at a rate of 1° C. per minute) until the desired temperature is reached. Alternatively, the temperature can be reduced at a controlled rate until a desired temperature is reached (e.g., between −80° C. and −180° C.), and then the sample or macromolecule can be flash frozen (e.g., by immersing the sample or macromolecule in liquid nitrogen or placing the sample or macromolecule above liquid nitrogen). The peptoid polymer, peptoid-peptide hybrid, or cryoprotectant solution can be contacted with the sample or macromolecule being cryopreserved at any point during the protocol, as long as it is before the formation of ice crystals that damage the sample or macromolecule being preserved.

As yet another non-limiting example, compositions and methods of the present invention are useful for cryogenic freezing protocols (e.g., −90° C. to −196° C.). For example, a biological sample or macromolecule can be contacted with a peptoid polymer, peptoid-peptide hybrid, or cryoprotectant solution described herein, then plunged into liquid nitrogen or a stream of liquid nitrogen vapor in order to quickly freeze the sample without the formation of ice crystals. No ice lattice exists and so the water within the sample or macromolecule is in an amorphous or glass-like state. Therefore, damaging ice is not formed.

One of skill in the art will readily appreciate that the concentrations and compositions of the peptoid polymers, peptoid-peptide hybrids, and cryoprotectant solutions described herein can be modified depending on the particular biological sample and/or macromolecule being cryopreserved and the particular cryopreservation protocol being employed.

F. Methods of Screening

In a related aspect, the present invention provides methods for screening peptoid polymers, peptoid-peptide hybrids, and/or cryoprotectant solutions for activity.

In one embodiment, the peptoid polymer, peptoid-peptide hybrid, and/or cryoprotectant solution is screened for lowering the freezing point of water using a polarized light microscope to detect ice crystal formation. Polarized light microscopy is an optical microscopy technique that uses polarized light as the light source. Image contrast arises from the interaction of plane-polarized light with a birefringent (or doubly-refracting) species to produce two individual wave components that are each polarized in mutually perpendicular planes. The velocities of these components, which are termed the ordinary and the extraordinary wavefronts, are different and vary with the propagation direction through the specimen. After exiting the specimen, the light components become out of phase, but are recombined with constructive and destructive interference when they pass through the analyzer. This interference creates a detectable contrast in the sample. Ice crystal formation is easily detected using this technique because ice crystals are birefringent species. In a standard experiment, samples comprising the peptoid polymer, peptoid-peptide hybrid, and/or cryoprotectant solution are cooled to a desired temperature for a desired amount of time. One or more samples, while at the desired temperature, are placed under the polarized light microscope and visually inspected for formation of ice crystals.

In one embodiment, the peptoid polymer, peptoid-peptide hybrid, and/or cryoprotectant solution is screened for lowering the freezing point of an aqueous solution using differential scanning calorimetry to quantitate thermal hysteresis activity. Differential scanning calorimetry is a thermoanalytical technique in which the difference in the amount of heat required to increase the temperature of a sample and reference is measured as a function of temperature. When a physical transformation such as phase transition occurs, more or less heat will need to flow to the sample than the reference to maintain both at the same temperature. The difference in temperature between the phase transition of the reference and the sample reports on the sample's ability to reduce or inhibit ice crystal formation at sub 0° C. temperatures. In a standard experiment, a sample comprising the peptoid polymer, peptoid-peptide hybrid, and/or cryoprotectant solution is compared to a reference that lacks the peptoid polymer, peptoid-peptide hybrid, and/or cryoprotectant solution.

G. Cell Viability Assays to Test for Activity

In a related aspect, the present invention provides cell viability assays to test for the ability of the peptoid polymer, peptoid-peptide hybrid, and/or cryoprotectant solution to maintain cell viability at reduced temperatures.

In some embodiments, cell viability is tested using the alamarBlue® Cell Viability Assay Protocol provided by Thermo Fisher Scientific, Inc. Briefly, alamarBlue® is the trade name of resazurin (7-Hydroxy-3H-phenoxazin-3-one 10-oxide) which is a non-toxic cell permeable compound that is blue in color and virtually non-fluorescent. Upon entering cells, resazurin is reduced to resorufin, a compound that is red in color and highly fluorescent. Viable cells continuously convert resazurin to resorufin, increasing the overall fluorescence and color of the media surrounding cells. Non-viable cells do not convert resazurin to resorufin, thus the overall fluorescence and color of the media surrounding the cells is an indication of the relative amount of viable cells in the sample. In a standard experiment, cells and the peptoid polymer, peptoid-peptide hybrid, and/or cryoprotectant solution are mixed in any suitable container. The mixture is then cooled to the desired sub 0° C. temperature and held for the desired amount of time. Cells are then returned to ambient temperatures and the almarBlue® reagent is added, incubated, and measured following the Thermo Fisher protocol. Typically, direct readout of cell viability is determined by measuring the relative fluorescence of the samples at the wavelengths $\lambda_{Ex}$~560 nm/$\lambda_{Em}$~590 nm.

In some embodiments, cell viability is tested using the LIVE/DEAD® Viability/Cytotoxicity Kit, for mammal cells provided by Thermo Fisher Scientific, Inc. This kit uses two indicator molecules: calcein AM and Ethidium homodoimer-1 (EthD-1). Live cells are distinguished by the presence of ubiquitous intracellular esterase activity, determined by the enzymatic conversion of the virtually nonfluorescent cell-permeant calcein AM to the intensely fluorescent calcein. The polyanionic dye calcein is well retained within live cells, producing an intense uniform green fluorescence in live cells ($\lambda_{EX}$~495 nm/$\lambda_{Ex}$~515 nm). Conversely, EthD-1 enters cells with damaged membranes and undergoes a 40-fold enhancement of fluorescence upon binding to nucleic acids, thereby producing a bright red fluorescence in dead cells ($\lambda_{EX}$~495 nm/$\lambda_{Em}$~635 nm). Notably, EthD-1 is excluded by the intact plasma membrane of live cells, so the determination of live and dead cells is easily distinguishable. Calcein and EthD-1 can be viewed simultaneously with a conventional fluorescein longpass filter. Alternatively, the fluorescence from these dyes may also be observed separately; calcein can be viewed with a standard fluorescein bandpass filter, and EthD-1 can be viewed with filters for propidium iodide or Texas Red® dye. In a standard experiment, cells and the peptoid polymer, peptoid-peptide hybrid, and/or cryoprotectant solution are mixed in any suitable container. The mixture is then cooled to the desired sub 0° C. temperature, held at that temperature for the desired amount of time, and then returned to ambient temperatures. Subsequent steps involving the addition of the calcein AM and EthD-1 reagents and measuring the assay results are performed as described in the Thermo Fisher protocol. Typically, direct readout of cell viability is determined by measuring the relative fluorescence at the above indicated wavelengths for both reagents.

In some embodiments, cell viability is tested using the MTT assay. The MTT assay is a colorimetric cell viability and proliferation assay that relies upon the reduction of yellow tetrazolium MTT (3-(4,5-dimethylthiazolyl-2)-2,5-diphenyltetrazolium bromide) to the insoluble formazan, which has a purple color. Tetrazolium dye reduction is dependent on NAD(P)H-dependent oxidoreductase enzymes, primarily located in the cytosolic compartment of metabolically active cells. The MTT assay is available, for example, from ATCC (www.atcc.org) or Sigma-Aldrich (www.sigmaaldrich.com). In a standard experiment, cells and the peptoid polymer, peptoid-peptide hybrid, and/or cryoprotectant solution are mixed in any suitable container. The mixture is then cooled to the desired sub 0° C. temperature and held for the desired amount of time. Cells are then returned to ambient temperatures and the MTT reagent is added, incubated, and measured following the ATCC or Sigma-Aldrich protocol. Typically, absorbance of converted dye is measured at a wavelength of 570 nm with background subtraction at 630-690 nm.

IV. Examples

The following examples are offered to illustrate, but not to limit, the claimed invention.

Example 1. Peptoid-Mediated Inhibition of Ice Crystal Formation

This example illustrates the ice crystal inhibition properties of N-substituted peptoid polymers and peptoid-peptide hybrids at sub 0° C. temperatures.

Capillary Tube Assays

In this experiment, four water-based samples were prepared in capillary tubes containing MilliQ purified water. One sample contained only water, and another sample contained 160 mM ethylene glycol (EG). The other two samples each contained a peptoid polymer at 9 mM. One of the peptoid polymer samples contained the peptoid polymer called "Compound 1," while the other sample contained the peptoid polymer called "Compound 10." The sequences of the peptoid polymers are as follows:

```
Compound 1:
                                        (SEQ ID NO: 1)
Nsb-Nsb-Nhp-Nsb-Nsb-Nhp-Nsb-Nsb-Nhp-Nsb;

Compound 10:
                                        (SEQ ID NO: 2)
Nhp-Nhp-Nhp-Nhp-Nhp-Nhp-Nhp-Nhp-Nhp.
```

The chemical structures for these compounds are provided in Table 2.

Figure 2A:
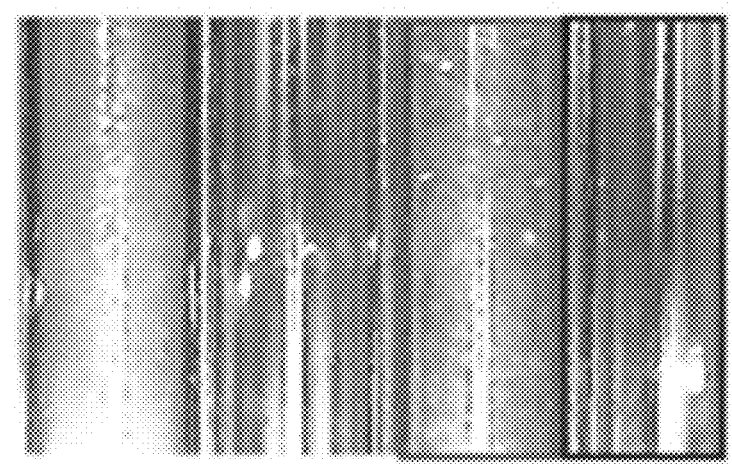
FIGS. 2A and 2B show the results of a capillary tube freeze assay that was performed at −20° C.
Figure 2B:
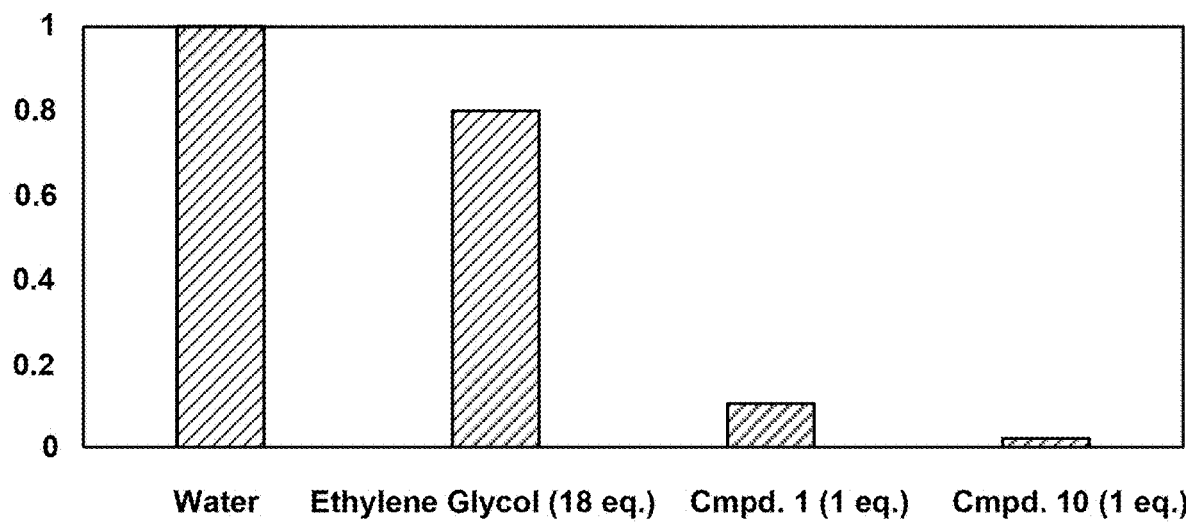
Figure 4A:
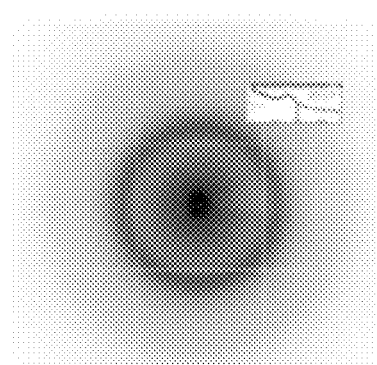
FIGS. 4A-4G show x-ray diffraction (XRD) crystallography data for solutions containing 5 mg/mL of Compound 10, Compound 12, Compound 8, Compound 13, Compound 11, and Compound 58, compared to a ethylene glycol (EG) control. Each solution also contained 300 mM NaCl, 100 mM HEPES, 15% (v/v) ethylene glycol, and pH was adjusted to 7.2.
Figure 4A:
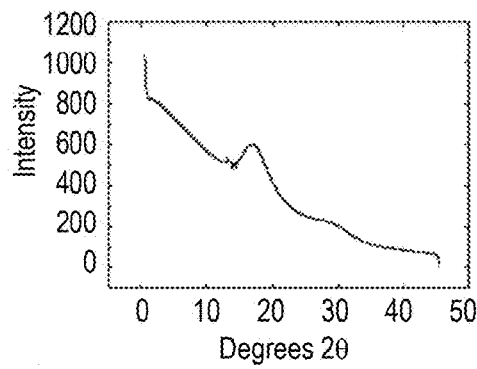
Figure 4B:
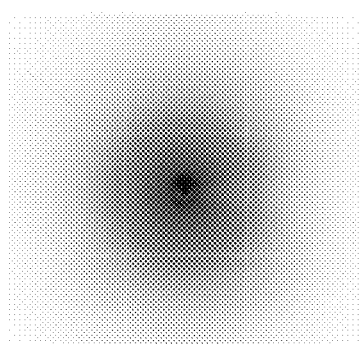
Figure 4B:
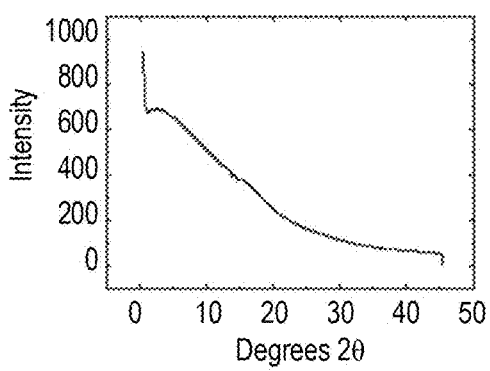
Figure 4C:
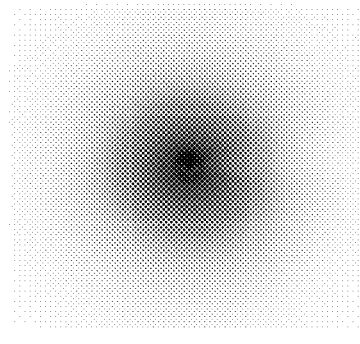
Figure 4C:
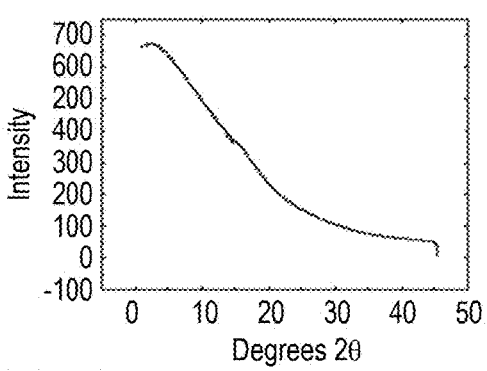
Figure 4D:
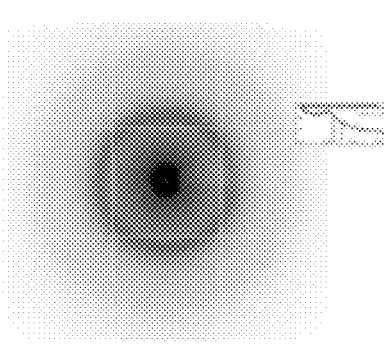
Figure 4D:
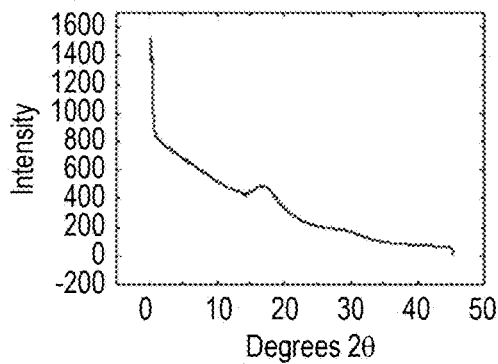
Figure 4E:
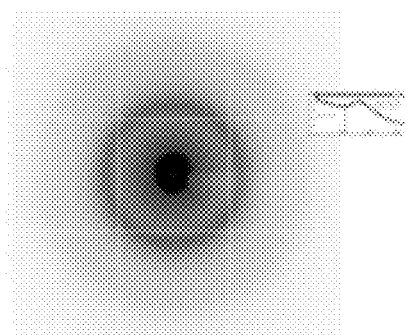
Figure 4E:
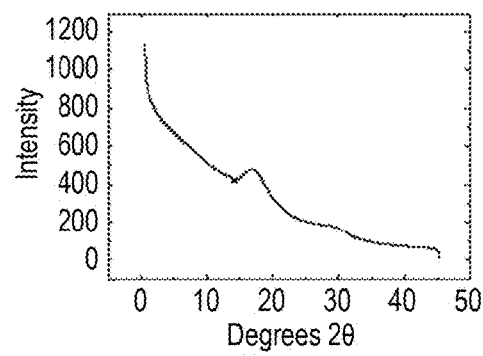
Figure 4F:
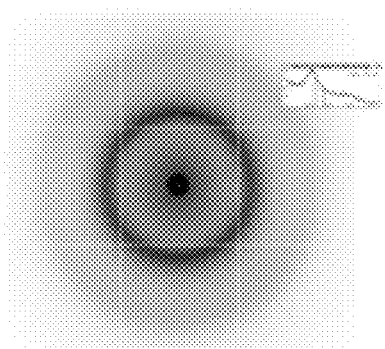
Figure 4F:
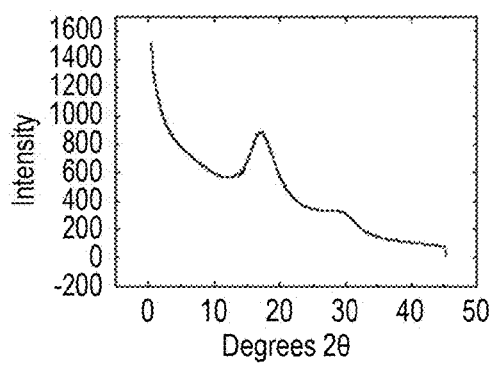
Figure 4G:
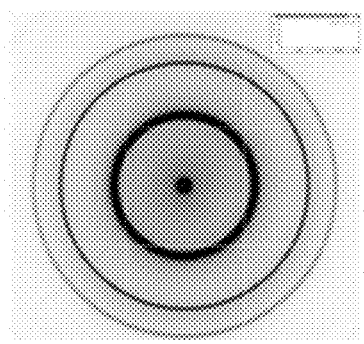
Figure 4G:
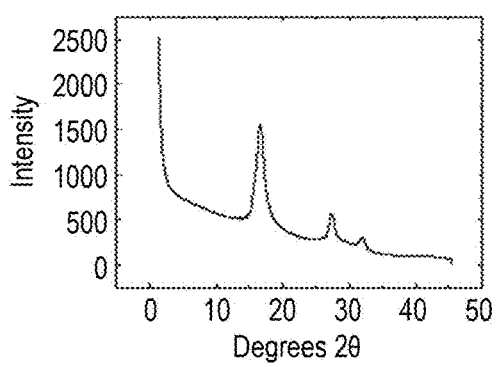
Figure 5A:
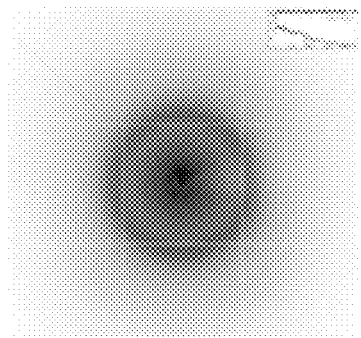
FIGS. 5A-5G show x-ray diffraction (XRD) crystallography data for solutions containing 1 mg/mL of Compound 10, Compound 12, Compound 8, Compound 13, Compound 11, and Compound 58, compared to a ethylene glycol (EG) control. Each solution also contained 300 mM NaCl, 100 mM HEPES, 17.5% (v/v) ethylene glycol, and pH was adjusted to 7.2.
Figure 5A:
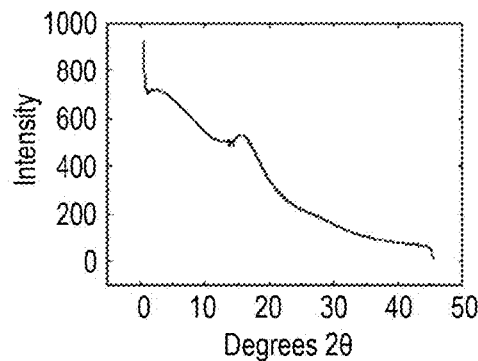
Figure 5B:
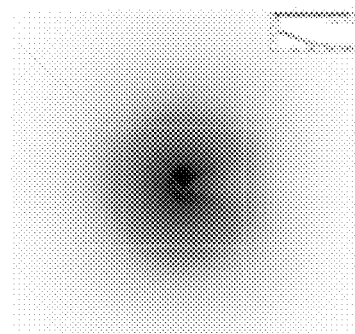
Figure 5B:
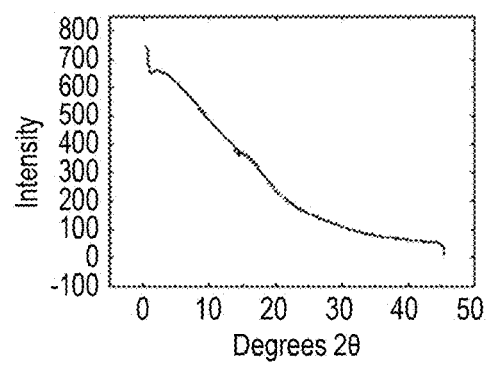
Figure 5C:
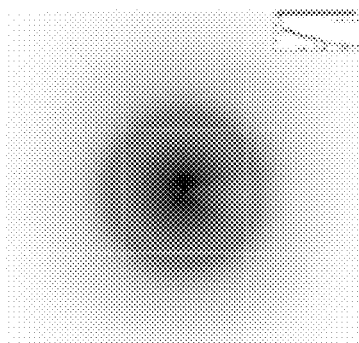
Figure 5C:
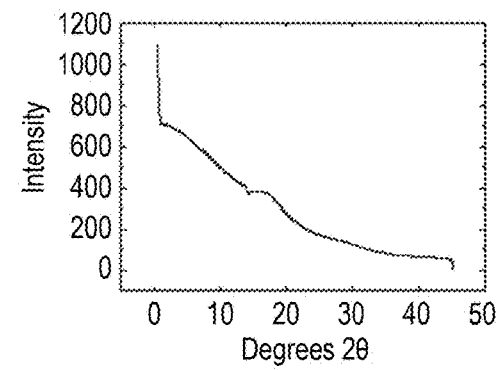
Figure 5D:
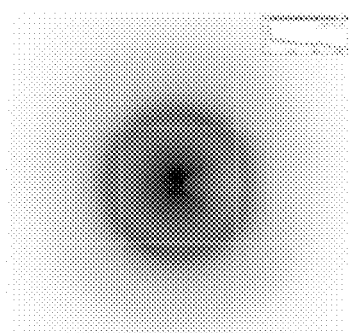
Figure 5D:
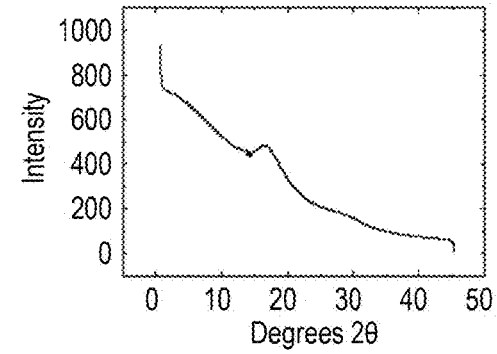
Figure 5E:
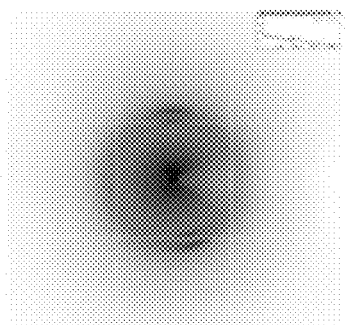
Figure 5E:
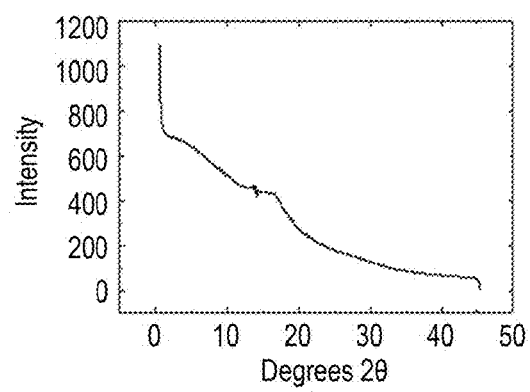
Figure 5F:
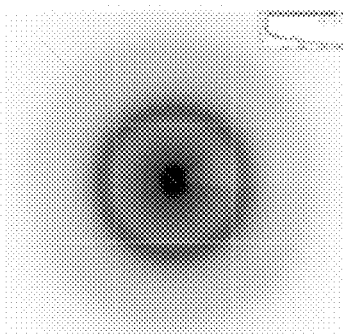
Figure 5F:
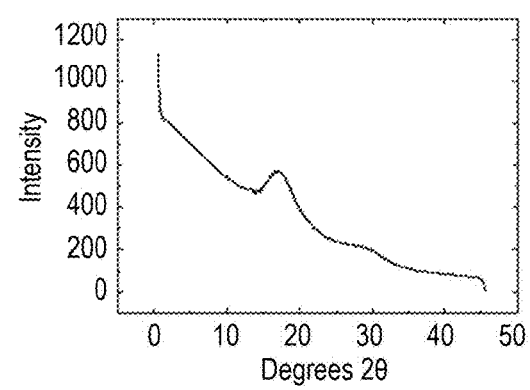
Figure 5G:
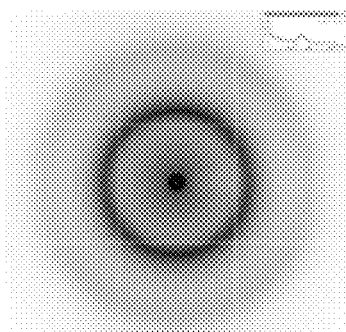
Figure 5G:
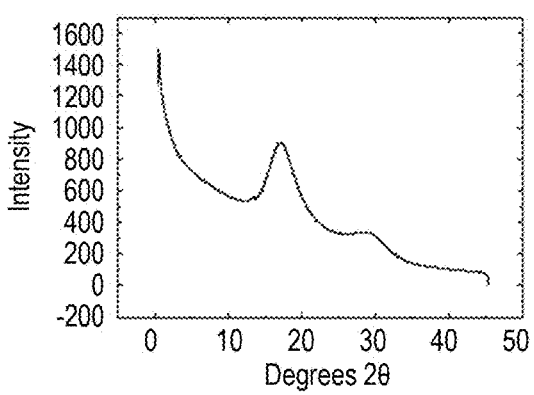

After sample preparation, all samples were slow cooled and incubated at −20° C. on a Peltier cooled plate. After one hour, samples were removed and immediately photographed using a digital camera attached to a 180× Stereo Zoom microscope (FIG. 2A). The water and EG samples showed significant ice crystal formation, although the EG sample showed less ice formation than the water-only sample. In contrast, neither of the samples containing the peptoid polymer compounds exhibited significant ice crystal formation. Normalized data is presented in FIG. 2B. Of note, the EG sample, containing a CPA concentration that was about 18 times higher than the peptoid sample concentrations, still exhibited significant ice formation whereas the peptoid samples did not.

Crystallographic X-Ray Diffraction Assays

In order to increase the throughput of library analysis, a crystallographic x-ray diffraction (XRD) technique was used to evaluate ice crystal formation. For these experiments, the compounds named "Compound 2," "Compound 8," "Compound 10," "Compound 11," "Compound 12," "Compound 13," and "Compound 58" were tested. Compounds 2, 8, 10, 11, 12, and 13 are peptoid polymers, the structures of which are provided in Table 2. Compound 58 is a peptoid-peptide hybrid, the structure of which is provided in Table 10. Compound 58 is similar to Compound 12, except that an arginine amino acid has been appended to the N-terminal end.

For these experiments, EG concentrations between 15% and 30% (v/v) were used. Typically, EG, DMSO, and other cryoprotectants are used during XRD sample analysis at concentrations of 35-40% (v/v) to vitrify solutions and avoid diffraction interference from ice crystals. Concentrations of 1 and 5 mg/mL of the peptoid and peptoid-peptide compounds were used. FIGS. 3A, 3B, and 3C illustrate exemplary XRD data under conditions of complete vitrification, partial vitrification with the presence of cubic ice, and freezing (cubic ice crystals), respectively. XRD data for Compounds 8, 10, 11, 12, 13, and 58 is provided in FIGS. 4A-4G and FIGS. 5A-5G. FIG. 3D provides ice rings scores for a variety of EG concentrations and two concentrations of Compounds 2, 8, and 12.

Several mixtures of the testing solution sample sets showed a strong anti-icing effect. FIG. 3D shows the experimental results of some peptoid polymer solutions compared to EG. "IceRing1" and "IceRing2" refer to ice formation scores, which range between 0 (no ice formation) and 15 (large ice formation). Compounds 2, 12, and 8 and others significantly reduced necessary EG concentrations while preventing ice formation.

The sample containing Compound 12 at a concentration of 5 mg/mL (0.5% (w/v)) and EG at a concentration of 17.5% (v/v) in water was ice-free after flash freezing. This particular mixture was found to completely eliminate all ice formation over multiple trials of flash freezing in a stream of liquid nitrogen vapor (FIG. 3A), and vastly outperformed a standard solution of 30% EG (FIG. 3B). In the figures, black spots and rings represent ice crystals. In comparison to EG at the same molar concentration, this anti-icing effect is 500 times stronger and, without being bound by any particular theory, suggests a non-colligative mechanism for anti-icing, which is the mechanism used by natural antifreeze proteins.

Larger Volume Assays

Figure 6A:
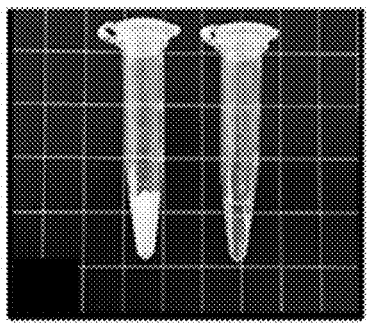
FIGS. 6A-6C show two solutions that were flash frozen, rewarmed, and subsequently refrozen. The control solution contained 22.5% (v/v) ethylene glycol (EG), while the test solution contained 22.5% EG and 5 mg/mL (0.5% (w/v)) Compound 12.
Figure 6B:
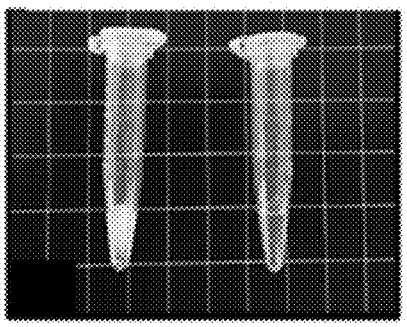

In order to test the usefulness of compositions of the present invention at larger scales, experiments were performed using solution volumes that are similar to volumes used for standard egg and stem cell preservation. For these experiments, two samples, one containing 22.5% EG and buffer only, and another containing 22.5% EG and 5 mg/ml (0.5% w/v) of Compound 12 and buffer, were flash frozen in liquid nitrogen. As shown in FIG. 6A, the Compound 12 solution showed complete vitrification with no ice formation immediately after removal from liquid nitrogen, while the control solution had clearly been frozen, yielding a mass of white ice crystals. The rewarming of the solutions in a 37° C. water bath led to an unexpected and beneficial result. The Compound 12 solution bypassed devitrification in less than 2 seconds upon rewarming (FIG. 6B, right), whereas chunks of ice were seen floating in the control sample (FIG. 6B, left) after 20 seconds. Condensation was seen on each of the tubes because the tubes were actually still much below room temperature. This result shows that Compound 12 acts as an active de-icer during thawing.

Figure 6C:
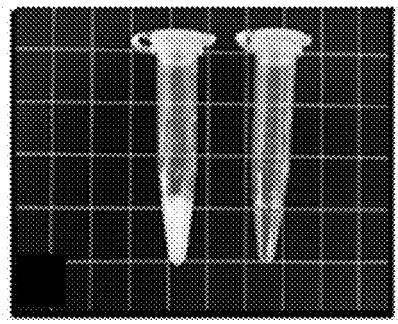

Furthermore, after leaving the 100 µL samples in a −20° C. freezer overnight, the Compound 12 solution was found to be unfrozen (FIG. 6C, right). This result shows that compositions of the present invention provide the ability to preserve samples at below 0° C. temperatures for long periods of time without any ice formation. Furthermore, these experiments show that ice-free conditions can be reached with hypothermic cryopreservation, or by the supercooling method, at −20° C. as well as near vitrification to −80° C. by incorporating compounds of the present invention to significantly reduce the critical concentration of penetrating CPAs and mitigate cryopreservation toxicity.

As shown here, a formulation of Compound 12 was found to prevent ice formation during vitrification in sub-milliliter volumes. In fact, the solutions were able to remain completely unfrozen at −20° C. and were also able to vitrify when flash frozen at −196° C. Currently, standard human egg cell preservation techniques for in vitro fertilization are limited to solution volumes of less than 5 µL (often 0.5 to 2.5 µL) while using 50% or greater cryoprotectant concentrations. Thus, Compound 12 was able to prevent ice formation in a practical volume, with exceedingly less cryoprotectant, which makes it useful, for example, for preserving human oocytes for in vitro fertilization.

Example 2. Cytotoxicity and Cryopreservation Screening

This example shows that compositions of the present invention have little to no cell toxicity and can achieve superior cryopreservation when compared to existing compounds, while reducing the necessary amount of CPAs and thus reducing CPA-associated toxicity.

Cytotoxicity Assays

In order to demonstrate the safety of cryoprotectant compositions of the present invention, a high-throughput cell-based cytotoxicity assay was developed utilizing the HEK 293 cell line, which is a sturdy and robust stem cell line grown from human embryonic kidney cells in tissue culture.

A Tecan Genesis Robotic Workstation was used to prepare solutions in 96- and 384-well plates. Solutions contained culture media, buffers, a cryoprotectant composition of the present invention (Compound 12) or DMSO. Solutions were adjusted to the desired pH. Serial dilutions were performed to obtain solutions containing various concentrations of Compound 12 and DMSO. Control experiments were performed using only culture media.

For these experiments, cells were seeded at low density (i.e., 10% confluence), exposed to solutions containing Compound 12 or DMSO, and placed in a 37° C. incubator. The cells were allowed to grow until control cells that were treated only with empty vehicle approached 70% confluence (typically about 3 to 5 days). Assessment for compound cytotoxicity was via MTT assay.

Figure 7:
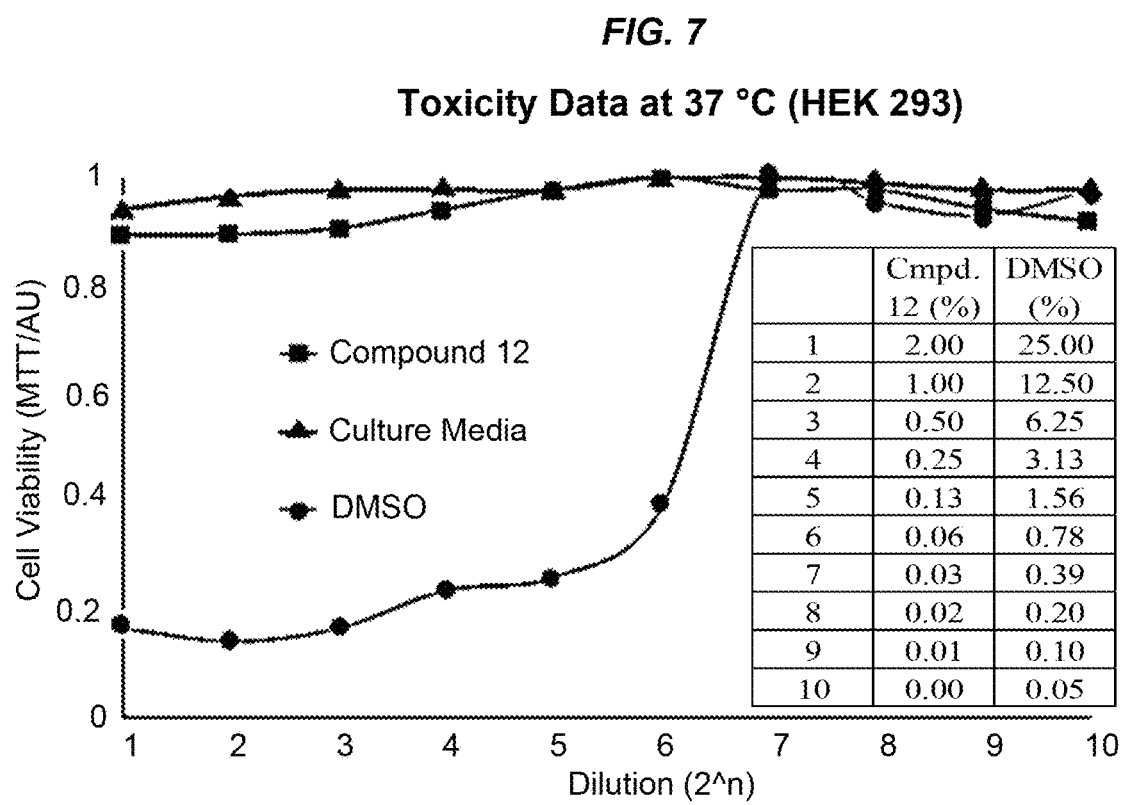
FIG. 7 shows the results of a cell toxicity study performed on HEK 293 cells in which Compound 12 (squares) or DMSO (circles) was added to cell culture media. A sample in which no Compound 12 or DMSO was added ("Culture Media" (triangles)) served as a control. Serial dilutions were performed in order to test different concentrations of Compound 12 and DMSO.

As can be seen in FIG. 7, the toxicity of Compound 12 did not significantly deviate from the that of culture media alone when analyzed by MTT assay. On the other hand, DMSO did not allow for warm survival for an extended period of time at any concentration above 0.5% (v/v). Notably, Compound 12 did not show toxicity at the concentrations in which it can prevent ice formation in a non-biological sample (0.5% w/v) and did not show significant toxicity at concentrations four times greater than this concentration, either.

These results show that compositions of the present invention were effective at ice-prevention even at concentrations where DMSO toxicity significantly reduced cell survival.

Cryopreservation Assays

Initial cryopreservation assays were performed using very simple solutions, with and without the addition of Compound 12, in order to minimize confounding outside factors. For this first set of experiments, two sample solutions were prepared. The first sample solution contained simple buffer and ethylene glycol (EG) at a concentration of 22.5% (v/v), and the second sample solution contained simple buffer, EG (22.5% (v/v)), and 5 mg/mL (0.5% (w/v)) of Compound 12.

HEK 293 cells were grown until 70% confluent, then treated with trypsin to remove adhesion proteins and yield free floating cells. Cells were counted using a hemocytometer and sample cell concentrations were adjusted to final concentrations of 10,000 cells per microliter. Cells were then compressed into tight pellets by centrifugation, and each sample was subsequently mixed with 20 μL of one of the sample solutions. Samples were then flash frozen by immersion in liquid nitrogen, followed by rewarming in a 37° C. water bath. After the freeze-thaw process, cells were suspended in a 400x volume of culture media for recovery. The positive control sample was treated with culture media at 37° C. and not subjected to the freeze-thaw process. The negative control sample was treated with culture media only during the freeze-thaw process. After recovery, cells were stained with Calcein AM for 30 minutes and cell viability was measured using a fluorescence plate reader.

Figure 8:
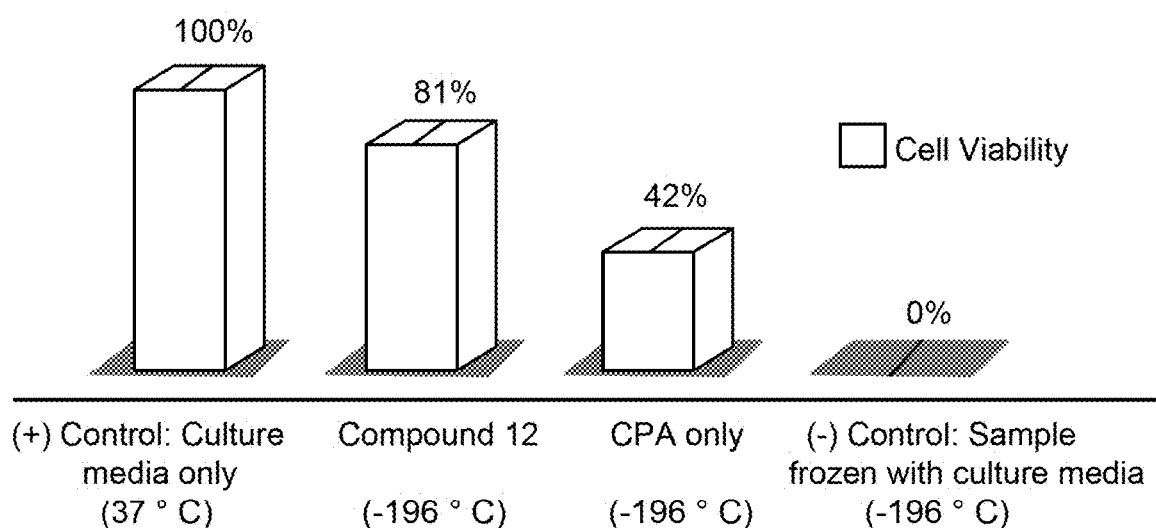
FIG. 8 shows the results of a cryopreservation assay performed on HEK 293 cells, comparing a solution containing ethylene glycol (EG) to a solution containing EG and Compound 12. Cell viability was measured 12 hours post-thaw.

As shown in FIG. 8, the addition of Compound 12 greatly improved cell survival and demonstrated the ability of this compound to cryopreserve cells. It was observed that the sample containing Compound 12 achieved complete vitrification without ice formation during the freezing process. In addition, the process of devitrification was bypassed much more rapidly compared to the sample lacking Compound 12.

Figure 9:
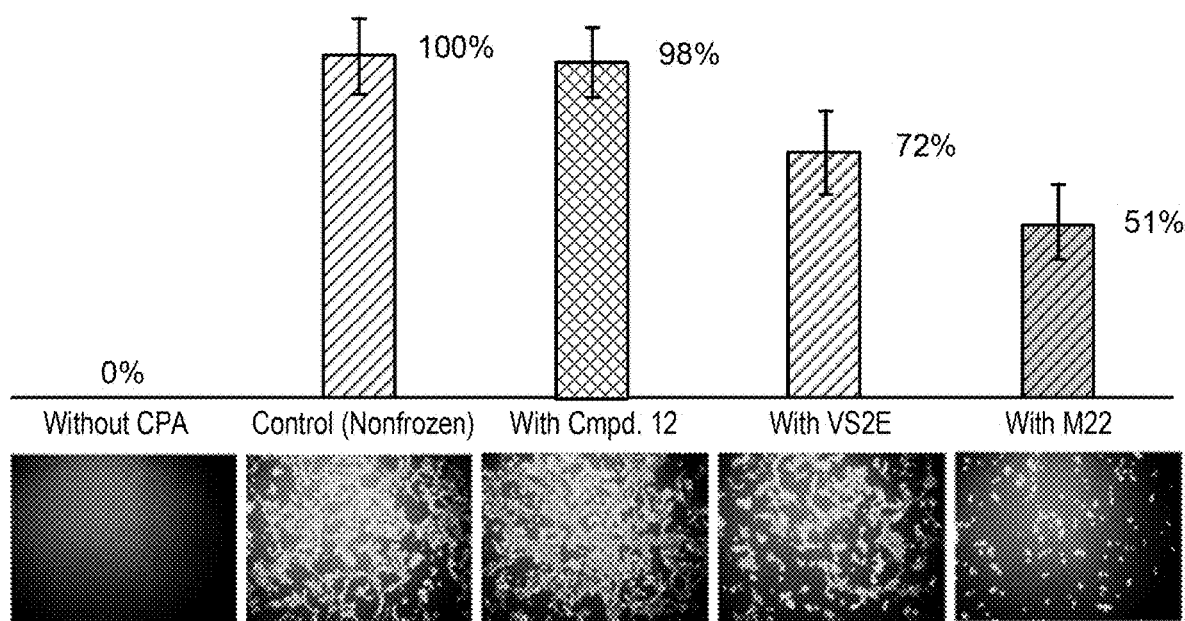
FIG. 9 shows the results of a cryopreservation assay performed on HEK 293 cells, comparing a solution containing 5 mg/mL of Compound 12 plus a mixture of glycols, disaccharides, and a general buffer to solutions containing VS2E or M22. Cell viability was measured 16 hours post-thaw. Cell were vitrified with liquid nitrogen (LN2).

A second set of experiments was performed to evaluate the cryopreservation potential of a formulation that contained 5 mg/mL of Compound 12 plus a mixture of glycols, disaccharides, and a general buffer. Post-thaw survival following vitrification in liquid nitrogen was evaluated as described above. As can be seen in FIG. 9, the formulation achieved near 100% (i.e., 98%) post-thaw survival of the cells, which was similar to the control sample that was not exposed to freezing treatment. The cell morphologies and florescence signals looked identical to the non-frozen controls, which indicated that little damage occurred to the cells during the experiment.

As part of the second set of experiments, the cryopreservation potential of the formulation was compared to two known cryopreservation reagents. VS2E is a DMSO-free and serum-free solution containing non-chemically defined polymers (see, e.g., Nishigaki et al. *Int. J. Dev. Biol.* 55:3015-311 (2011)), and M22 is an organ vitrification solution available from 21$^{st}$ Century Medicine. FIG. 9 shows that the formulation containing Compound 12 achieved superior cryopreservation, as cell survival was 72% and 51% for VS2E and M22, respectively. It should be noted that for the M22 sample, background fluorescence may have skewed this result, as a count of live cells in the image suggested that far fewer than 51% of the cells had survived.

The compositions of the present invention were highly effective at preventing ice formation in solutions containing significantly reduced ethylene glycol. In particular, low concentrations of the compositions (e.g., 0.5% (w/v)) were sufficient to block ice growth during vitrification and to keep solutions in a liquid, ice-free state on the 20 μL scale, which is a scale that is useful for the preservation of various types of cells.

In summary, these results show that compositions of the present invention can achieve superior cryopreservation and reduce the necessary amount of CPAs, thus reducing cell toxicity that is associated with CPAs. The superior properties of the compositions of the present invention are especially useful for the treatment of particularly sensitive cell lines and/or when cells need to be cultured for longer time periods.

V. Exemplary Embodiments

Exemplary embodiments provided in accordance with the presently disclosed subject matter include, but are not limited to, the claims and the following embodiments:

1. A peptoid polymer according to formula (I):

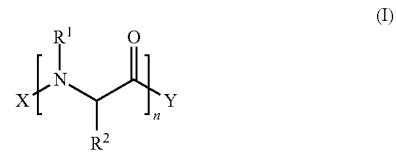

(I)

a tautomer thereof or stereoisomer thereof, wherein:

each R1 is independently selected from the group consisting of H, optionally substituted C1-18 alkyl, optionally substituted C2-18 alkenyl, optionally substituted C2-18 alkynyl, optionally substituted C1-18 hydroxyalkyl, optionally substituted alkoxy, optionally substituted C1-18 alkylamino, optionally substituted C1-18 alkylthio, optionally substituted carboxyalkyl, C3-10 cycloalkyl, heterocycloalkyl, aryl, heteroaryl, (C3-10 cycloalkyl)alkyl, (heterocycloalkyl)alkyl, arylalkyl, and heteroarylalkyl, wherein at least one instance of R1 is C1-18 hydroxyalkyl, and wherein any of the cycloalkyl, heterocycloalkyl, aryl, and heteroaryl groups is optionally and independently substituted with one or more R3 groups;

each R2 is independently selected from the group consisting of H, optionally substituted C1-18 alkyl, optionally substituted C2-18 alkenyl, optionally substituted C2-18 alkynyl, optionally substituted C1-18 hydroxyalkyl, optionally substituted C1-18 alkylamino, optionally substituted C1-18 alkylthio, and optionally substituted carboxyalkyl;

each R3 is independently selected from the group consisting of halogen, oxo, thioxo, OH, SH, amino, C1-8 alkyl, C1-8 hydroxyalkyl, C1-8 alkylamino, and C1-8 alkylthio;

X and Y are independently selected from the group consisting of H, optionally substituted C1-8 alkyl, optionally substituted C1-8 acyl, optionally substituted C1-8 alkylamino, OH, SH, NH2, carboxy, optionally substituted C1-8 hydroxyalkyl, optionally substituted C1-8 alkylamino, optionally substituted C2-8 alkylthio, optionally substituted C1-8 carboxyalkyl, and halogen, or alternatively X and Y are taken together to form a covalent bond; and the subscript n, representing the number of monomers in the polymer, is between 2 and 50;

provided that all instances of R1 are not hydroxyethyl when n is between 3 and 7.

2. The peptoid polymer of embodiment 1, wherein each R1 is independently selected from the group consisting of

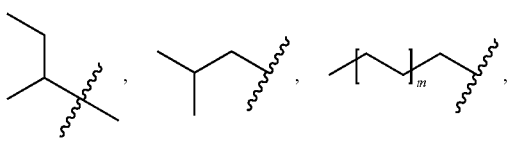

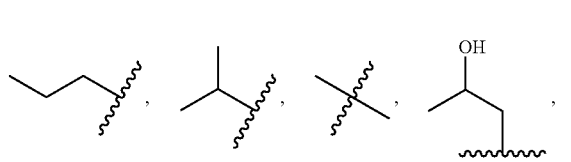

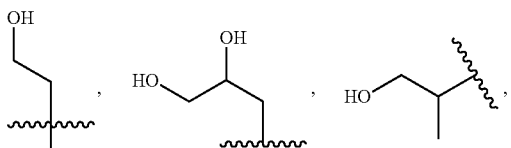

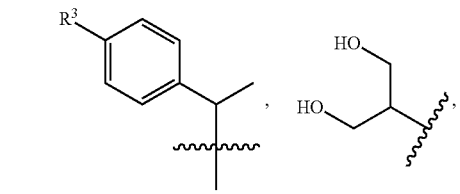

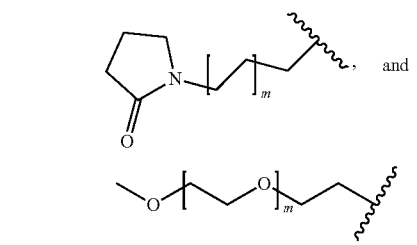

wherein:

m is between 1 and 8; and

R3 is selected from the group consisting of H, C1-8 alkyl, halogen, hydroxyl, thiol, nitro, amine, oxo, and thioxo.

3. The peptoid polymer of embodiment 2, wherein one or more R1 has a structure according to R1a:

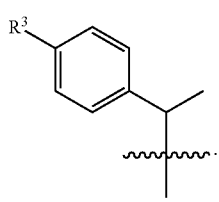

R1a

4. The peptoid polymer of embodiment 3, wherein each R1a group is independently selected from:

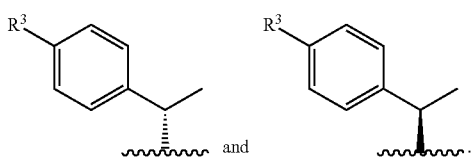

5. The peptoid polymer of embodiment 3, wherein each R1a group is:

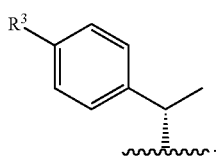

6. The peptoid polymer of embodiment 3, wherein each R1a group is:

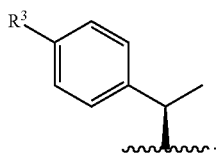

7. The peptoid polymer of embodiment 2, wherein one or more R1 has a structure according to R1b:

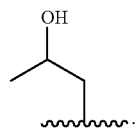

R1b

8. The peptoid polymer of embodiment 7, wherein each R1b group is independently selected from:

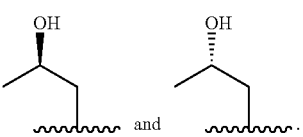

9. The peptoid polymer of embodiment 7, wherein each R1b group is:

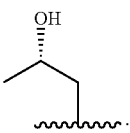

10. The peptoid polymer of embodiment 7, wherein each R1b group is:

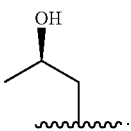

11. The peptoid polymer of embodiment 1, wherein each R1 is independently selected from the group consisting of

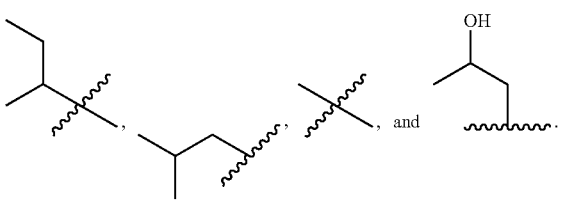

12. The peptoid polymer of embodiment 1, wherein each instance of R1 is an independently selected C1-18 hydroxyalkyl group.
13. The peptoid polymer of embodiment 12, wherein each instance of R1 is an independently selected C1-6 hydroxyalkyl group.
14. The peptoid polymer of embodiment 13, wherein each instance of R1 is an the same C1-6 hydroxyalkyl group.
15. The peptoid polymer of embodiment 14, wherein each instance of R1 is

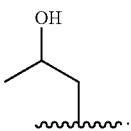

16. The peptoid polymer of any one of embodiments 1 to 15, wherein each instance of R2 is H.
17. The peptoid polymer of any one of embodiments 1 to 16, wherein n is between 3 and 25.
18. The peptoid polymer of any one of embodiments 1 to 16, wherein n is between 8 and 50.
19. The peptoid polymer of any one of embodiments 1 to 16, wherein n is between 8 and 20.
20. The peptoid polymer of any one of embodiments 1 to 19, wherein X is selected from the group consisting of H, C1-8 alkyl, and C1-8 acyl; and Y is selected from the group consisting of —OH and amino.
21. The peptoid polymer of any one of embodiments 1 to 19, wherein X and Y are taken together to form a covalent bond.
22. The peptoid polymer of embodiment 1, wherein n is 10 and the peptoid polymer comprises:
3 Nhp (2-((2-hydroxypropyl)amino)acetic acid) monomers and 7 Nsb (2-(sec-butylamino)acetic acid) monomers; or
4 Nhp monomers and 6 Nsb monomers; or
5 Nhp monomers and 5 Nsb monomers; or
6 Nhp monomers and 4 Nsb monomers; or
7 Nhp monomers and 3 Nsb monomers; or
8 Nhp monomers and 2 Nsb monomers; or
10 Nhp monomers.
23. The peptoid polymer of embodiment 22, wherein the peptoid polymer has the sequence Nhp-Nhp-Nhp-Nhp-Nhp-Nhp-Nhp-Nhp-Nhp-Nhp; X is H or C1-8 acyl; and Y is —OH or —NH2 or C1-8 alkyl.
24. The peptoid polymer of embodiment 22, wherein the peptoid polymer has the sequence Nsb-Nsb-Nhp-Nsb-Nsb-Nhp-Nsb-Nsb-Nhp-Nsb; X is H or C1-8 acyl; and Y is —OH or —NH2 or C1-8 alkyl.
25. The peptoid polymer of embodiment 22, wherein the peptoid polymer has the sequence Nsb-Nhp-Nhp-Nhp-Nsb-Nhp-Nhp-Nhp-Nsb-Nhp; X is H or C1-8 acyl; and Y is —OH or —NH2 or C1-8 alkyl.
26. The peptoid polymer of embodiment 22, wherein the peptoid polymer has the sequence Nsb-Nsb-Nhp-Nhp-Nsb-Nsb-Nhp-Nhp-Nsb-Nsb; X is H or C1-8 acyl; and Y is —OH or —NH2 or C1-8 alkyl.
27. The peptoid polymer of embodiment 22, wherein the peptoid polymer has the sequence Nsb-Nhp-Nhp-Nhp-Nhp-Nhp-Nsb-Nhp-Nhp-Nhp; X is H or C1-8 acyl; and Y is —OH or —NH2 or C1-8 alkyl.
28. The peptoid polymer of embodiment 22, wherein the peptoid polymer has a sequence set forth in Table 2.
29. The peptoid polymer of embodiment 1, wherein n is 10 and the peptoid polymer comprises:
3 Nhp (2-((2-hydroxypropyl)amino)acetic acid) monomers and 7 Nine (2-(methylamino)acetic acid) monomers; or
4 Nhp monomers and 6 Nine monomers; or
5 Nhp monomers and 5 Nine monomers; or
6 Nhp monomers and 4 Nine monomers; or
7 Nhp monomers and 3 Nine monomers; or
8 Nhp monomers and 2 Nine monomers.
30. The peptoid polymer of embodiment 29, wherein the peptoid polymer has a sequence set forth in Table 3.
31. The peptoid polymer of embodiment 1, wherein n is 10 and the peptoid polymer comprises:
5 Nhe (2-((2-hydroxyethyl)amino)acetic acid) monomers and 5 Nsb (2-(sec-butylamino)acetic acid) monomers; or
5 Nhp (2-((2-hydroxypropyl)amino)acetic acid) monomers and 5 Nbu (2-butylamino)acetic acid) monomers.
32. The peptoid polymer of embodiment 31, wherein the peptoid polymer has a sequence set forth in Table 4.
33. The peptoid polymer of embodiment 1, wherein n is 10 and the peptoid polymer comprises:
4 Nhp (2-((2-hydroxypropyl)amino)acetic acid) monomers and 6 Nib (2-(isobutylamino)acetic acid) monomers; or
4 Nhp monomers and 6 Nbu (2-butylamino)acetic acid) monomers; or
4 Nhp monomers and 6 Npr (2-propylamino)acetic acid) monomers; or
4 Nhp monomers and 6 Nip (2-(isopropylamino)acetic acid) monomers.
34. The peptoid polymer of embodiment 33, wherein the peptoid polymer has a sequence set forth in Table 5.
35. The peptoid polymer of embodiment 1, wherein n is 14 and the peptoid polymer comprises:
6 Nhp (2-((2-hydroxypropyl)amino)acetic acid) monomers and 8 Nsb (2-(sec-butylamino)acetic acid) monomers; or
7 Nhp monomers and 7 Nsb monomers; or
8 Nhp monomers and 6 Nsb monomers; or
10 Nhp monomers and 4 Nsb monomers; or
14 Nhp monomers.

36. The peptoid polymer of embodiment 35, wherein the peptoid polymer has a sequence set forth in Table 6.

37. The peptoid polymer of embodiment 1, wherein n is 14 and the peptoid polymer comprises:
6 Nhp (2-((2-hydroxypropyl)amino)acetic acid) monomers and 8 Nib (2-(isobutylamino)acetic acid) monomers; or
7 Nhp monomers and 7 Nib monomers; or
8 Nhp monomers and 6 Nib monomers; or
10 Nhp monomers and 4 Nib monomers; or
14 Nhp monomers.

38. The peptoid polymer of embodiment 37, wherein the peptoid polymer has a sequence set forth in Table 7.

39. The peptoid polymer of embodiment 1, wherein n is 16 and the peptoid polymer comprises:
5 Nhp (2-((2-hydroxypropyl)amino)acetic acid) monomers and 11 Nsb (2-(sec-butylamino)acetic acid) monomers; or
7 Nhp monomers and 9 Nsb monomers; or
8 Nhp monomers and 8 Nsb monomers; or
10 Nhp monomers and 6 Nsb monomers; or
12 Nhp monomers and 4 Nsb monomers; or
16 Nhp monomers.

40. The peptoid polymer of embodiment 39, wherein the peptoid polymer has a sequence set forth in Table 8.

41. The peptoid polymer of embodiment 1, wherein n is 22 and the peptoid polymer comprises:
7 Nhp (2-((2-hydroxypropyl)amino)acetic acid) monomers and 15 Nsb (2-(sec-butylamino)acetic acid) monomers; or
10 Nhp monomers and 12 Nsb monomers; or
11 Nhp monomers and 11 Nsb monomers; or
14 Nhp monomers and 8 Nsb monomers; or
17 Nhp monomers and 5 Nsb monomers; or
22 Nhp monomers.

42. The peptoid polymer of embodiment 41, wherein the peptoid polymer has a sequence set forth in Table 9.

43. The peptoid polymer of any one of embodiments 1 to 42, wherein the peptoid polymer forms a helical structure.

44. The peptoid polymer of any one of embodiments 1 to 43, wherein the peptoid polymer reduces or inhibits ice crystal formation at a temperature within about 0° C. to about −20° C.

45. The peptoid polymer of any one of embodiments 1 to 43, wherein the peptoid polymer reduces or inhibits ice crystal formation at a temperature within about −20° C. to about −40° C.

46. The peptoid polymer of any one of embodiments 1 to 43, wherein the peptoid polymer reduces or inhibits ice crystal formation at about −20° C.

47. The peptoid polymer of any one of embodiments 1 to 43, wherein the peptoid polymer reduces or inhibits ice crystal formation at a temperature within about −40° C. to about −200° C.

48. A peptoid-peptide hybrid comprising a peptoid polymer of any one of embodiments 1 to 47 and one or more amino acids, wherein the one or more amino acids are located at one or both ends of the peptoid polymer and/or between one or more peptoid monomers.

49. The peptoid-peptide hybrid of embodiment 48, wherein the one or more amino acids are selected from the group consisting of alanine, cysteine, aspartic acid, glutamic acid, phenylalanine, glycine, histidine, isoleucine, arginine, lysine, leucine, methionine, asparagine, proline, glutamine, serine, threonine, valine, tryptophan, tyrosine, and a combination thereof.

50. The peptoid-peptide hybrid of embodiment 48, wherein the one or more amino acids are selected from the group consisting of isoleucine, leucine, serine, threonine, alanine, valine, arginine, and a combination thereof.

51. A cryoprotectant solution comprising a peptoid polymer of any one of embodiments 1 to 47, a peptoid-peptide hybrid of any one of embodiments 48 to 50, or a combination thereof.

52. The cryoprotectant solution of embodiment 51, further comprising a compound selected from the group consisting of an ionic species, a penetrating cryoprotectant, a non-penetrating cryoprotectant, an antioxidant, a cell membrane stabilizing compound, an aquaporin or other channel forming compound, an alcohol, a sugar, a sugar derivative, a nonionic surfactant, a protein, dimethyl sulfoxide (DMSO), polyethylene glycol (PEG), Ficoll®, polyvinylpyrrolidone, polyvinyl alcohol, hyaluronan, formamide, a natural or synthetic hydrogel, and a combination thereof.

53. The cryoprotectant solution of embodiment 52, wherein the alcohol is selected from the group consisting of propylene glycol, ethylene glycol, glycerol, methanol, butylene glycol, adonitol, ethanol, trimethylene glycol, diethylene glycol, polyethylene oxide, erythritol, sorbitol, xythyritol, polypropylene glycol, 2-methyl-2,4-pentanediol (MPD), mannitol, inositol, dithioritol, 1,2-propanediol, and a combination thereof.

54. The cryoprotectant solution of embodiment 52, wherein the sugar is a monosaccharide.

55. The cryoprotectant solution of embodiment 54, wherein the monosaccharide is selected from the group consisting of glucose, 3-O-Methyl-D-glucopyranose, galactose, arabinose, fructose, xylose, mannose, and a combination thereof.

56. The cryoprotectant solution of embodiment 52, wherein the sugar is a disaccharide.

57. The cryoprotectant solution of embodiment 56, wherein the disaccharide is selected from the group consisting of sucrose, trehalose, lactose, maltose, and a combination thereof.

58. The cryoprotectant solution of embodiment 52, wherein the sugar is a polysaccharide.

59. The cryoprotectant solution of embodiment 58, wherein the polysaccharide is selected from the group consisting of raffinose, dextran, and a combination thereof.

60. The cryoprotectant solution of embodiment 52, wherein the PEG has an average molecular weight less than about 1,000 g/mol.

61. The cryoprotectant solution of embodiment 52, wherein the PEG has an average molecular weight between about 200-400 g/mol.

62. The cryoprotectant solution of embodiment 52, wherein the protein is selected from the group consisting of egg albumin, bovine serum albumin, human serum albumin, gelatin, and a combination thereof.

63. The cryoprotectant solution of embodiment 52, wherein the natural or synthetic hydrogel comprises chitosan, hyaluronic acid, or a combination thereof.

64. The cryoprotectant solution of embodiment 52, wherein the nonionic surfactant is selected from the group consisting of polyoxyethylene lauryl ether, polysorbate 80, and a combination thereof.

65. A method for preserving a tissue, organ, or cell, the method comprising contacting the tissue, organ, or cell with a peptoid polymer of any one of embodiments 1 to 47, a peptoid-peptide hybrid of any one of embodiments 48 to 50, a cryoprotectant solution of any one of embodiments 51 to 64, or a combination thereof.
66. The method of embodiment 65, wherein the peptoid polymer, peptoid-peptide hybrid, cryoprotectant solution, or combination thereof is present in an amount sufficient to reduce or inhibit ice crystal formation at a temperature within about 0° C. to about −20° C.
67. The method of embodiment 65, wherein the peptoid polymer, peptoid-peptide hybrid, cryoprotectant solution, or combination thereof is present in an amount sufficient to reduce or inhibit ice crystal formation at a temperature within about −20° C. to about −40° C.
68. The method of embodiment 65, wherein the peptoid polymer, peptoid-peptide hybrid, cryoprotectant solution, or combination thereof is present in an amount sufficient to reduce or inhibit ice crystal formation at about −20° C.
69. The method of embodiment 65, wherein the peptoid polymer, peptoid-peptide hybrid, cryoprotectant solution, or combination thereof is present in an amount sufficient to reduce or inhibit ice crystal formation at a temperature within about −40° C. to about −200° C.
70. The method of any one of embodiments 65 to 69, wherein the tissue is a bioengineered tissue.
71. The method of any one of embodiments 65 to 70, wherein the peptoid polymer, the peptoid-peptide hybrid, or a combination thereof is present in amount between about 100 nM and about 100 mM.
72. The method of any one of embodiments 65 to 71, wherein the tissue, organ, or cell is selected from the group consisting of heart, liver, lung, kidney, pancreas, intestine, thymus, cornea, nerve cells, blood platelets, sperm cells, oocytes, embryonic cells, stem cells, human pluripotent stem cells, hematopoietic stem cells, lymphocytes, granulocytes, immune system cells, bone cells, organoids, and a combination thereof.
73. A method for preserving a biological macromolecule, the method comprising contacting the biological macromolecule with a peptoid polymer of any one of embodiments 1 to 47, a peptoid-peptide hybrid of any one of embodiments 48 to 50, a cryoprotectant solution of any one of embodiments 51 to 64, or a combination thereof.
74. The method of embodiment 73, wherein the biological macromolecule is selected from the group consisting of a nucleic acid, an amino acid, a protein, an isolated protein, a peptide, a lipid, a composite structure, and a combination thereof.
75. A cosmetic care product comprising a peptoid polymer of any one of embodiments 1 to 47, a peptoid-peptide hybrid of any one of embodiments 48 to 50, a cryoprotectant solution of any one of embodiments 51 to 64, or a combination thereof.
76. An antifreeze product comprising a peptoid polymer of any one of embodiments 1 to 47, a peptoid-peptide hybrid of any one of embodiments 48 to 50, a cryoprotectant solution of any one of embodiments 51 to 64, or a combination thereof.
77. The antifreeze product of embodiment 76, wherein the antifreeze product is a deicing or ice-inhibiting product used to prevent, inhibit, or delay the formation of ice on an object.
78. The antifreeze product of embodiment 77, wherein the object is selected from the group consisting of an aircraft or a part thereof, a gas pipeline, a window, electrical equipment, a drone, a cable, a power line, mechanical equipment, a car engine, a gear system, and a brake system.
79. A frozen food product comprising a peptoid polymer of any one of embodiments 1 to 47, a peptoid-peptide hybrid of any one of embodiments 48 to 50, a cryoprotectant solution of any one of embodiments 51 to 64, or a combination thereof.
80. The frozen food product of embodiment 79, wherein the frozen food product is selected from the group consisting of ice cream, yogurt, seafood, fruit, and meat products.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described. All publications, patents, and patent applications cited in this specification are herein incorporated by reference as if each individual publication, patent, or patent application were specifically and individually indicated to be incorporated by reference.

VI. Informal Sequence Listing

| SEQ ID NO: | Sequence | Notes |
| --- | --- | --- |
| 1 | Nsb-Nsb-Nhp-Nsb-Nsb-Nhp-Nsb-Nsb-Nhp-Nsb | Compound 1 |
| 2 | Nhp-Nhp-Nhp-Nhp-Nhp-Nhp-Nhp-Nhp-Nhp-Nhp | Compound 10 |
| 3 | Nep-Nep-Xaa-Xaa-Xaa-Xaa-Nep-Nep-Nep-Nep-Nme-Nme | Peptoid-Peptide Hybrid |
| 4 | Nme-Nme-Xaa-Nme-Nme-Nme-Nme-Nhp-Nhp-Nsb-Xaa-Nme-Nme-Xaa-Nme-Nme-Nme | Peptoid-Peptide Hybrid |
| 5 | Nme-Nme-Xaa-Nme-Nme-Nme-Nme-Nme-Nme-Nme-Xaa-Xaa | Peptoid-Peptide Hybrid |
| 6 | Arg-Nsb-Nsb-Nhp-Nhp-Nsb-Nsb-Nhp-Nhp-Nsb-Nsb | Peptoid-Peptide Hybrid (Compound 58) |

-continued

| SEQ ID NO: | Sequence | Notes |
|---|---|---|
| 7 | Nsb-Nhp-Nhp-Nhp-Nsb-Nhp-Nhp-Nhp-Nsb-Nhp | Compound 6 |
| 8 | Nsb-Nsb-Nhp-Nhp-Nsb-Nsb-Nhp-Nhp-Nsb-Nsb | Compound 12 |
| 9 | Nsb-Nhp-Nhp-Nhp-Nhp-Nhp-Nsb-Nhp-Nhp-Nhp | Compound 8 |
| 10 | Nsb-Nsb-Nsb-Nhp-Nhp-Nhp-Nsb-Nsb-Nsb-Nhp | Compound 2 |

What is claimed is:

1. A peptoid polymer having a length of from 8 to 50 monomers, wherein the peptoid polymer comprises at least two Nhp (2-((2-hydroxypropyl) amino) acetic acid) monomers.

2. The peptoid polymer of claim 1, wherein the peptoid polymer comprises at least three Nhp monomers.

3. The peptoid polymer of claim 1, wherein the peptoid polymer comprises at least four Nhp monomers.

4. The peptoid polymer of claim 1, wherein the peptoid polymer comprises at least two contiguous Nhp monomers.

5. The peptoid polymer of claim 4, wherein the peptoid polymer comprises two contiguous Nhp monomers.

6. The peptoid polymer of claim 1, wherein the peptoid polymer comprises at least three contiguous Nhp monomers.

7. The peptoid polymer of claim 6, wherein the peptoid polymer comprises three contiguous Nhp monomers.

8. The peptoid polymer of claim 1, wherein the peptoid polymer has a length of from 8 to 25 monomers.

9. The peptoid polymer of claim 1, wherein the peptoid polymer has a length of from 8 to 20 monomers.

10. The peptoid polymer of claim 1, wherein the peptoid polymer has a length of from 10 to 25 monomers.

11. The peptoid polymer of claim 1, wherein the peptoid polymer reduces or inhibits ice crystal formation at a temperature within about 0° C. to about −20° C.

12. The peptoid polymer of claim 1, wherein the peptoid polymer reduces or inhibits ice crystal formation at a temperature within about −20° C. to about −200° C.

13. A cryoprotectant solution comprising a peptoid polymer of claim 1.

* * * * *